United States Patent
Parks et al.

(10) Patent No.: US 11,571,458 B2
(45) Date of Patent: Feb. 7, 2023

(54) BACTERIOCINS TO IMPROVE VAGINAL COLONIZATION OF HYDROGEN PEROXIDE PRODUCING LACTOBACILLUS FOR FEMALE REPRODUCTIVE HEALTH

(71) Applicant: Osel, Inc., Mountain View, CA (US)

(72) Inventors: Thomas P. Parks, San Mateo, CA (US); Trine Nilsen, Foster City, CA (US)

(73) Assignee: Osel, Inc., Mountain View, CA (US)

( * ) Notice: Subject to any disclaimer, the term of this patent is extended or adjusted under 35 U.S.C. 154(b) by 0 days.

(21) Appl. No.: 17/187,535

(22) Filed: Feb. 26, 2021

(65) Prior Publication Data

US 2021/0275628 A1    Sep. 9, 2021

Related U.S. Application Data

(63) Continuation of application No. PCT/US2019/048732, filed on Aug. 29, 2019.

(60) Provisional application No. 62/724,797, filed on Aug. 30, 2018.

(51) Int. Cl.

| | |
|---|---|
| *A61K 38/12* | (2006.01) |
| *A61K 45/06* | (2006.01) |
| *A61K 38/16* | (2006.01) |
| *A61K 9/00* | (2006.01) |
| *A61K 9/06* | (2006.01) |
| *A61P 15/02* | (2006.01) |
| *A61K 31/4164* | (2006.01) |
| *A61K 31/7056* | (2006.01) |
| *A61K 35/747* | (2015.01) |

(52) U.S. Cl.
CPC .......... *A61K 38/164* (2013.01); *A61K 9/0034* (2013.01); *A61K 9/06* (2013.01); *A61K 31/4164* (2013.01); *A61K 31/7056* (2013.01); *A61K 35/747* (2013.01); *A61P 15/02* (2018.01)

(58) Field of Classification Search
CPC ............ A61K 31/4168; A61K 2300/00; A61K 31/4164; A61K 31/7056; A61K 35/747; A61K 38/12; A61K 38/164; A61K 45/06; A61K 9/0034; A61K 9/06; A61K 38/16; A61K 9/00; A61P 15/02; C07K 14/335
See application file for complete search history.

(56) References Cited

U.S. PATENT DOCUMENTS

| | | | | |
|---|---|---|---|---|
| 2006/0134745 A1* | 6/2006 | Klaenhammer | ..... | C07K 14/335 536/23.7 |
| 2015/0050253 A1* | 2/2015 | Gabant | ..... | C12N 1/20 435/254.2 |
| 2016/0213005 A1 | 7/2016 | Gabant | | |
| 2018/0186837 A1 | 7/2018 | Cho et al. | | |
| 2020/0123209 A1* | 4/2020 | Yount | ..... | G01N 33/50 |

FOREIGN PATENT DOCUMENTS

| | | |
|---|---|---|
| WO | 9846261 A1 | 10/1998 |
| WO | 2018013583 A2 | 1/2018 |
| WO | 2020047203 A2 | 3/2020 |

OTHER PUBLICATIONS

Ahmad et al., "Antimicrobial Potential of Bacteriocins: In Therapy, Agriculture and Food Preservation", International Journal of Antimicrobial Agents, vol. 49, No. 1, Sep. 29, 2016, pp. 1-11.

Dover et al., "Safety Study of an Antimicrobial Peptide Lactocin 160, Produced by the Vaginal Lactobacillus Rhamnosus", Infectious Diseases In Obstetrics And Gynecology, vol. 2007, No. 6, Dec. 9, 2007, pp. 1-6.

Application No. EP19855845.4, Extended European Search Report, dated May 11, 2022, 8 pages.

Maldonado-Barragan et al., "Purification and Genetic Characterization Of Gassericin E, A Novel Co-culture Inducible Bacteriocin From Lactobacillus Gasseri Ev1461 Isolated From the Vagina of A Healthy Woman", BMC Microbiology, vol. 16, No. 37, Mar. 12, 2016, 14 pages.

Mavric et al., "Bacteriocins of Lactobacillus Gassed K7—Monitoring of Gassericin K7 A and B Genes' Expression and Isolation of An Active C", Process Biochemistry, vol. 49, No. 8, May 20, 2014, pp. 1251-1259.

Moncla et al., "In Vitro Activity of Cationic Peptides Against *Neisseria gonorrhoeae* and Vaginal *Lactobacillus* Species: The Effect of Divalent Cations", Advances in Bioscience and Biotechnology, vol. 3, 2012, pp. 249-255.

PCT/US2019/048732, "International Search Report and Written Opinion", dated Feb. 19, 2020, 13 pages.

PCT/US2019/048732, "Invitation to Pay Additional Fees and, Where Applicable, Protest Fee", Dec. 30, 2019, 3 pages.

* cited by examiner

*Primary Examiner* — Julie Ha
(74) *Attorney, Agent, or Firm* — Kilpatrick Townsend and Stockton LLP

(57) ABSTRACT

Methods are described for increasing levels of healthy vaginal bacteria by treating the vaginal mucosa with bacteriocins derived from *Lactobacillus* paragasseri, *Lactobacillus* gasseri, and other bacterial strains. The bacteriocins are surprisingly advantageous as being selectively active against *Lactobacillus iners* but relatively inactive against $H_2O_2$-producing *Lactobacillus* species. Because *L. iners* is involved in the onset and maintenance of vaginal dysbiosis, selective removal of this bacterium from the vaginal microbiome treats or prevents conditions associated with vaginal dysbiosis, such as bacterial vaginosis and its sequelae.

20 Claims, 10 Drawing Sheets
Specification includes a Sequence Listing.

SEQUENCE LISTING

```
<160> NUMBER OF SEQ ID NOS: 19

<210> SEQ ID NO 1
<211> LENGTH: 57
<212> TYPE: PRT
<213> ORGANISM: Lactobacillus paragasseri

<400> SEQUENCE: 1

Arg Asn Asn Trp Ala Ala Asn Ile Gly Gly Ala Gly Gly Ala Thr Val
1               5                   10                  15

Ala Gly Trp Ala Leu Gly Asn Ala Val Cys Gly Pro Ala Cys Gly Phe
            20                  25                  30

Val Gly Ala His Tyr Val Pro Ile Ala Trp Ala Gly Val Thr Ala Ala
        35                  40                  45

Thr Gly Gly Phe Gly Lys Ile Arg Lys
    50                  55

<210> SEQ ID NO 2
<211> LENGTH: 48
<212> TYPE: PRT
<213> ORGANISM: Lactobacillus paragasseri

<400> SEQUENCE: 2

Asn Lys Trp Gly Asn Ala Val Ile Gly Ala Ala Thr Gly Ala Thr Arg
1               5                   10                  15

Gly Val Ser Trp Cys Arg Gly Phe Gly Pro Trp Gly Met Thr Ala Cys
            20                  25                  30

Gly Leu Gly Gly Ala Ala Ile Gly Gly Tyr Leu Gly Tyr Lys Ser Asn
        35                  40                  45

<210> SEQ ID NO 3
<211> LENGTH: 64
<212> TYPE: PRT
<213> ORGANISM: Lactobacillus paragasseri

<400> SEQUENCE: 3

Lys Asn Trp Ser Val Ala Lys Cys Gly Gly Thr Ile Gly Thr Asn Ile
1               5                   10                  15

Ala Ile Gly Ala Trp Arg Gly Ala Arg Ala Gly Ser Phe Phe Gly Gln
            20                  25                  30

Pro Val Ser Val Gly Thr Gly Ala Leu Ile Gly Ala Ser Ala Gly Ala
        35                  40                  45

Ile Gly Gly Ser Val Gln Cys Val Gly Trp Leu Ala Gly Gly Gly Arg
    50                  55                  60
```

<210> SEQ ID NO 4
<211> LENGTH: 53
<212> TYPE: PRT
<213> ORGANISM: Lactobacillus paragasseri

<400> SEQUENCE: 4

Asn Asn Val Asn Trp Gly Ser Val Ala Gly Ser Cys Gly Lys Gly Ala
1               5                   10                  15

Val Met Glu Ile Tyr Phe Gly Asn Pro Ile Leu Gly Cys Ala Asn Gly
            20                  25                  30

Ala Ala Thr Ser Leu Val Leu Gln Thr Ala Ser Gly Ile Tyr Lys Asn
        35                  40                  45

Tyr Gln Lys Lys Arg
    50

<210> SEQ ID NO 5
<211> LENGTH: 64
<212> TYPE: PRT
<213> ORGANISM: Lactobacillus paragasseri

<400> SEQUENCE: 5

Lys Asn Trp Ser Val Ala Lys Cys Gly Gly Thr Ile Gly Thr Asn Ile
1               5                   10                  15

Ala Ile Gly Ala Trp Arg Gly Ala Arg Ala Gly Ser Phe Phe Gly Gln
            20                  25                  30

Pro Val Ser Val Gly Ala Gly Ala Leu Ile Gly Ala Ser Ala Gly Ala
        35                  40                  45

Ile Gly Gly Ser Val Gln Cys Val Gly Trp Leu Ala Gly Gly Gly Arg
    50                  55                  60

<210> SEQ ID NO 6
<211> LENGTH: 64
<212> TYPE: PRT
<213> ORGANISM: Lactobacillus paragasseri

<400> SEQUENCE: 6

Glu Asn Trp Ser Val Ala Lys Cys Gly Gly Thr Ile Gly Thr Asn Ile
1               5                   10                  15

Ala Ile Gly Ala Trp Arg Gly Ala Arg Ala Gly Ser Phe Phe Gly Gln
            20                  25                  30

Pro Val Ser Val Gly Ala Gly Ala Leu Ile Gly Ala Ser Ala Gly Ala
        35                  40                  45

Ile Gly Gly Ser Val Gln Cys Val Gly Trp Leu Ala Gly Gly Gly Arg
    50                  55                  60

<210> SEQ ID NO 7
<211> LENGTH: 37
<212> TYPE: PRT
<213> ORGANISM: Lactobacillus paragasseri

<400> SEQUENCE: 7

Ser Phe Phe Gly Gln Pro Val Ser Val Gly Thr Gly Ala Leu Ile Gly
1               5                   10                  15

Ala Ser Ala Gly Ala Ile Gly Gly Ser Val Gln Cys Val Gly Trp Leu
            20                  25                  30

Ala Gly Gly Gly Arg
        35

<210> SEQ ID NO 8
<211> LENGTH: 44

```
<212> TYPE: PRT
<213> ORGANISM: Lactobacillus paragasseri

<400> SEQUENCE: 8

Lys Asn Trp Ser Val Ala Lys Cys Gly Gly Thr Ile Gly Thr Asn Ile
1               5                   10                  15

Ala Ile Gly Ala Trp Arg Gly Ala Arg Ala Gly Ala Ile Gly Gly Ser
            20                  25                  30

Val Gln Cys Val Gly Trp Leu Ala Gly Gly Arg
        35                  40

<210> SEQ ID NO 9
<211> LENGTH: 53
<212> TYPE: PRT
<213> ORGANISM: Lactobacillus paragasseri

<400> SEQUENCE: 9

Asn Asn Val Asn Trp Gly Ser Val Ala Gly Ser Cys Gly Lys Gly Ala
1               5                   10                  15

Val Met Gly Ile Tyr Phe Gly Asn Pro Ile Leu Gly Cys Ala Asn Gly
            20                  25                  30

Ala Ala Thr Ser Leu Val Leu Gln Thr Ala Ser Gly Ile Tyr Lys Asn
        35                  40                  45

Tyr Gln Lys Lys Arg
    50

<210> SEQ ID NO 10
<211> LENGTH: 53
<212> TYPE: PRT
<213> ORGANISM: Lactobacillus paragasseri

<400> SEQUENCE: 10

Asn Asn Val Asn Trp Gly Ser Val Ala Gly Ser Cys Gly Lys Gly Ala
1               5                   10                  15

Val Met Gly Ile Tyr Phe Gly Asn Pro Ile Leu Gly Cys Ala Asn Gly
            20                  25                  30

Ala Ala Thr Ser Leu Val Leu Gln Thr Thr Ser Gly Ile Tyr Lys Asn
        35                  40                  45

Tyr Gln Lys Lys Arg
    50

<210> SEQ ID NO 11
<211> LENGTH: 57
<212> TYPE: PRT
<213> ORGANISM: Lactobacillus paragasseri

<400> SEQUENCE: 11

Arg Asn Asn Trp Ala Ala Asn Ile Gly Gly Val Gly Gly Ala Thr Val
1               5                   10                  15

Ala Gly Trp Ala Leu Gly Asn Ala Val Cys Gly Pro Ala Cys Gly Phe
            20                  25                  30

Val Gly Ala His Tyr Val Pro Ile Ala Trp Ala Gly Val Thr Ala Ala
        35                  40                  45

Thr Gly Gly Phe Gly Lys Ile Arg Lys
    50                  55

<210> SEQ ID NO 12
<211> LENGTH: 57
<212> TYPE: PRT
<213> ORGANISM: Lactobacillus paragasseri
```

<400> SEQUENCE: 12

Arg Asn Asn Trp Ala Ala Asn Ile Gly Gly Val Gly Gly Ala Thr Val
1               5                   10                  15

Ala Gly Trp Ala Leu Gly Asn Ala Val Cys Gly Pro Ala Cys Gly Phe
            20                  25                  30

Val Gly Glu His Tyr Val Pro Ile Ala Trp Ala Gly Val Thr Ala Ala
        35                  40                  45

Thr Gly Gly Phe Gly Lys Ile Arg Lys
    50                  55

<210> SEQ ID NO 13
<211> LENGTH: 57
<212> TYPE: PRT
<213> ORGANISM: Lactobacillus paragasseri

<400> SEQUENCE: 13

Arg Asn Asn Leu Ala Ala Asn Ile Gly Gly Val Gly Gly Ala Thr Val
1               5                   10                  15

Ala Gly Trp Ala Leu Gly Asn Ala Val Cys Gly Pro Ala Cys Gly Phe
            20                  25                  30

Val Gly Ala His Tyr Val Pro Ile Ala Trp Ala Gly Val Thr Ala Ala
        35                  40                  45

Thr Gly Gly Phe Gly Lys Ile Arg Lys
    50                  55

<210> SEQ ID NO 14
<211> LENGTH: 34
<212> TYPE: PRT
<213> ORGANISM: Lactobacillus paragasseri

<400> SEQUENCE: 14

Ala Val Cys Gly Pro Ala Cys Gly Phe Val Gly Ala His Tyr Val Pro
1               5                   10                  15

Ile Ala Trp Ala Gly Val Thr Ala Ala Thr Gly Gly Phe Gly Lys Ile
            20                  25                  30

Arg Lys

<210> SEQ ID NO 15
<211> LENGTH: 48
<212> TYPE: PRT
<213> ORGANISM: Lactobacillus paragasseri

<400> SEQUENCE: 15

Asn Lys Trp Gly Asn Ala Val Ile Gly Ala Ala Thr Gly Ala Thr Arg
1               5                   10                  15

Gly Val Ser Trp Cys Arg Gly Phe Gly Pro Trp Gly Met Thr Ala Cys
            20                  25                  30

Ala Leu Gly Gly Ala Ala Ile Gly Gly Tyr Leu Gly Tyr Lys Ser Asn
        35                  40                  45

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
agaaataatt gggctgctaa tata                                              24

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tttttaaagc ctgcaggatt ccctactttc t                                      31

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aacaacgtaa attggggtag                                                   20

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttactatcca tattccctgc aggtactatc tcttt                                  35
```

BACTERIOCINS TO IMPROVE VAGINAL COLONIZATION OF HYDROGEN PEROXIDE PRODUCING LACTOBACILLUS FOR FEMALE REPRODUCTIVE HEALTH

CROSS-REFERENCES TO RELATED APPLICATIONS

The present application is a Continuation of PCT Application No. PCT/US2019/048732, filed Aug. 29, 2019, which claims the benefit of priority to U.S. Provisional Application No. 62/724,797, filed Aug. 30, 2018, the full disclosures of which are incorporated herein by reference in its entireties for all purposes.

SEQUENCE LISTING

The instant application contains a Sequence Listing which has been submitted electronically in ASCII format and is hereby incorporated by reference in its entirety. Said ASCII copy, created on Feb. 23, 2021, is named 081029-1238413-002810US.txt and is 9,223 bytes in size.

FIELD OF THE INVENTION

This invention provides for methods of increasing levels of healthy vaginal bacteria by treating the vaginal mucosa with bacteriocins derived from Lactobacillus gasseri, Lactobacillus paragasseri, and other bacterial species. The bacteriocins are surprisingly advantageous as being selectively active against Lactobacillus iners but relatively inactive against hydrogen peroxide ($H_2O_2$) producing Lactobacillus species. Lactobacillus iners is often associated with dysbiosis of the vaginal microbiome and may contribute to recurrence of vaginal infections, such as bacterial vaginosis (BV).

BACKGROUND OF THE INVENTION

Generally, healthy vaginal microbiota exhibits low species diversity, and contain bacterial communities dominated by only a few Lactobacillus spp., which are gram-positive rods that play an important role in resisting infection via production of lactic acid and acidification of the vagina, by production of other antimicrobial products, such as $H_2O_2$ and antimicrobial peptides, or by competing for binding sites with vaginal pathogens (See, Osset et al., 2001. Assessment of the capacity of Lactobacillus to inhibit the growth of uropathogens and block their adhesion to vaginal epithelial cells. J. Infect. Dis. 183:485-91). The species of Lactobacillus most commonly isolated from the reproductive tracts of healthy women worldwide include L. crispatus, L. iners, L. jensenii, and L. gasseri. See, e.g., Srinivasan et al., 2012. Bacterial Communities in Women with Bacterial Vaginosis: High Resolution Phylogenetic Analyses Reveal Relationships of Microbiota to Clinical Criteria PLoS One 7(6), Article No.: e37818; Antonio et al., (1999) J Infect. Dis. 180:1950-1956; Vasquez et al., (2002) J Clin. Microbiol. 40:2746-2749; Vallor, A. C., et al. J Infect Dis. 2001 Dec. 1, 184(11):1431-6; Ravel, J., et al. Proc Natl Acad Sci, USA. 2011 Mar. 15, 108 Suppl 1:4680-7. These species are phylogenetically and functionally different from food and/or environmental Lactobacillus species. They metabolize glucose to lactic acid, contributing to the maintenance of a low vaginal pH (≤4.5) that accounts for a major part of the non-specific host defense of the vagina. Indeed, it has been demonstrated that women who have a vaginal microbiota with low species diversity, dominated by L. crispatus, L. gasseri, L. iners, and L. jensenii (i.e., Lactobacillus-dominated microbiota), experience a lower frequency of gonorrhea, chlamydial infections, trichomoniasis, BV, and HIV acquisition. L. crispatus and L. jensenii strains typically produce $H_2O_2$, a bactericidal agent, whereas about half of L. gasseri strains produce $H_2O_2$, and L. iners strains are generally not capable of producing $H_2O_2$ (Antonio, M. A. et al., (1999) J Infect. Dis. 180:1950-1956; France, M. T. et al., (2016) Appl Environ Microbiol. 82:7063-7073). $H_2O_2$-producing Lactobacillus are considered to be protective vaginal Lactobacillus, generally associated with vaginal health. Conversely, L. iners, a non-$H_2O_2$-producing Lactobacillus, is not considered a protective Lactobacillus because it coexists with BV organisms and is often present during BV.

In most healthy women of child-bearing age, the vaginal microbiota is dominated by $10^7$-$10^9$ colony forming units (CFU) of Lactobacillus per gram of fluid. Some women of childbearing age lack or have low levels of protective vaginal Lactobacillus, which can be due to the fact that the vaginal ecosystem is dynamically affected by the menstrual cycle, medications, general health status, sexual and hygiene practices, and contraception. When the normal acidic environment of a healthy vagina dominated by protective $H_2O_2$-producing Lactobacillus spp. is lost, it is generally replaced with a more diverse microbiota populated with non-Lactobacillus spp., such as Gardnerella vaginalis, Atopobium vaginae, Leptotrichia amnionii, Eggerthella, and organisms within the Clostridiales order. This increase in the number and diversity of such anaerobic bacteria and the loss of protective $H_2O_2$-producing Lactobacillus spp. are hallmarks of dysbiosis and BV. BV is associated with increased risk acquiring of multiple sexually transmitted infections (STIs), including chlamydia, gonorrhea, genital herpes, trichomoniasis, HIV, and HPV infection and progression to cervical intraepithelial neoplasia (CIN). BV is also implicated in numerous gynecologic and obstetric complications, including pelvic inflammatory disease (PID), endometritis, and post-operative infections, such as post-cesarean endometritis and post-hysterectomy vaginal cuff cellulitis. Strong associations have also been reported between BV and pre-term delivery, miscarriage, amniotic fluid infections, and poor in vitro fertilization outcomes. The presence of lactobacilli decreases the odds for fetal inflammatory responses to placental colonization with pathogens.

While L. iners can acidify the vagina like the other $H_2O_2$-producing Lactobacillus spp., L. iners produces less lactic acid, no D-lactic acid, and no $H_2O_2$, thereby offering comparatively less overall protection against vaginal colonization by pathogenic species. Furthermore, L. iners is the only vaginal Lactobacillus spp. to be recovered in high numbers in diverse microbiota and during BV. See, e.g., Vaneechoutte, M. et al. (2017) Research in Microbiology, 168(9-10):826-36. Thus, the role for L. iners is ambiguous, as it exists in the vaginal microbiota of asymptomatic women while also being the only vaginal Lactobacillus species that can coexist with BV-associated bacteria. See, e.g., Petrova, M. I. et al (2017) Trends Microbiol. 25(3): 182-91; Beamer, M. A. et al. (2017) Anaerobe, 45:40-3. L. iners is the only Lactobacillus species known to produce a cytotoxin (inerolysin), which is similar to vaginolysin produced by G. vaginalis (Rampersaud R. et al. (2011) J Bacteriol 193:1034-41). Expression of the L. iners cytotoxin is highly up regulated during BV (Macklaim J. M. et al. (2013) Microbiome 1:12). L. iners has an unusually small genome with reduced metabolic capabilities and has a greater dependency on exogenous nutrients than other vaginal lactobacilli (Macklaim J. M. et al. (2011) Proc Natl Acad Sci USA 108 Suppl 1:4688-95; France, M. T. et al., (2016) *Appl Environ Microbiol*. 82:7063-7073). Vaginal mucosa that is populated with significant amounts of *L. iners* can predispose women to developing a more diverse microbiota containing BV-associated bacteria because the *L. iners*-dominated bacterial community is the least stable, and *L. iners* is usually the major *Lactobacillus* species present during the transition to BV. See, e.g., Gajer, P. et al. (2012) *Sci. Transl. Med.* 4(132):132ra52; Macklaim, J. M. et al. (2011) *Proc. Natl. Acad. Sci. USA*, 108 Suppl. 1:4688-95; Santiago, G. L. et al. (2012) *PLoS One*, 7(9):e45281. For example, women colonized with *L. crispatus*, a protective vaginal species, have a 5-fold decreased risk for developing BV, while women with *L. iners* have a significantly greater risk of developing BV. See, Verstraelen, H. et al. (2009) *BMC Microbiol.*, 9:116, doi: 10.1186/1471-2180-9-116. Since *L. iners* is resistant to metronidazole, typically the only *Lactobacillus* present during BV, and competes for the same ecological niche as the other vaginal lactobacilli, it is usually the first *Lactobacillus* species to emerge and recolonize the vagina following treatment of BV with metronidazole. See, e.g., Jakobsson, T. et al. (2007) *J Clin. Microbiol.* 45(9):3145; Srinivasan, S. et al. (2012) *PLoS One*, 7(6): e37818; Ferris, M. J. et al. (2007) *J Clin. Microbiol.* 45(3): 1016-8.

Thus, women with low levels of $H_2O_2$-producing vaginal *Lactobacillus* can have a higher susceptibility to BV and associated gynecologic and obstetric complications, such as PID, pathogen transmission, higher miscarriage rates, preterm birth, and lower success rates when undergoing in vitro fertilization treatment, compared to women with relatively high population levels of *Lactobacillus* spp. that produce $H_2O_2$. Methods of increasing population levels of *Lactobacillus* spp. that produce $H_2O_2$ in the vaginal mucosa have been described as far back as the early 1990's. More recently, a method of combining products containing *Lactobacillus* spp. that produce $H_2O_2$ with the use of antibiotics have been described. However, without removing the large populations of *L. iners* from the vaginal mucosa to create a niche for $H_2O_2$-producing *Lactobacillus* spp. to grow and recolonize the microbiome, the non-*Lactobacillus* spp. associated with BV will recolonize and lead to more instances of BV. Therefore, a bactericidal product is needed for the treatment of vaginal infections, which selectively inhibits *L. iners*, creating a vaginal niche for protective $H_2O_2$-producing *Lactobacillus* spp. to grow and thrive. The present invention addresses these and other needs.

BRIEF SUMMARY OF THE INVENTION

In one aspect, the present invention provides for a bacteriocin composition of at least one pharmaceutically acceptable excipient; and at least one isolated peptide, or a combination of isolated peptides, wherein: the at least one isolated peptide, or combination of isolated peptides, has selective bactericidal activity against *L. iners*; the at least one isolated peptide is selected from the group consisting of SEQ ID NO:1, SEQ ID NO:2, SEQ ID NO:3, SEQ ID NO:4, and an isolated peptide having 90% sequence identity to one of SEQ ID NOs:1, 2, 3, or 4; and the bacteriocin composition is a formulation suitable for intravaginal applications. The at least one isolated peptide, or combination of isolated peptides, is present in an amount sufficient to exhibit bactericidal properties of the bacteriocin composition. In some embodiments, the bacteriocin composition of the invention further includes at least one antibiotic active against BV-associated organisms.

In another aspect, the present invention provides for a method of treating a patient having low levels of $H_2O_2$-producing vaginal *Lactobacillus* and a Nugent score of at least 4. The method involves intravaginally administering to the patient a bacteriocin composition of least one pharmaceutically acceptable excipient; and at least one isolated peptide, or a combination of isolated peptides, wherein: the at least one isolated peptide, or combination of isolated peptides, has selective bactericidal activity against *L. iners*; and the at least one isolated peptide is selected from the group consisting of SEQ ID NO:1, SEQ ID NO:2, SEQ ID NO:3, SEQ ID NO:4, and an isolated peptide having 90% sequence identity to one of SEQ ID NOs:1, 2, 3, or 4. The at least one isolated peptide, or a combination of isolated peptides, is administered in an amount sufficient to decrease levels of *L. iners* and to promote growth of endogenous $H_2O_2$-producing vaginal *Lactobacillus*.

In some embodiments, the method of treating a patient having low levels of $H_2O_2$-producing vaginal *Lactobacillus* and a Nugent score of at least 4 further involves optionally administering to the patient at least one antibiotic active against BV-associated organisms, in which the antibiotic is administered in an amount sufficient to decrease levels of BV-associated organisms. In some embodiments, the method involves administering the antibiotic in an amount that is between about 30 mg to about 2000 mg per daily dose and is administered to the patient once or twice daily for up to 7 days. In some embodiments, the method involves administering the antibiotic concurrently with the amount of peptide, or combination of peptides.

In some embodiments, the method of treating a patient having low levels of $H_2O_2$-producing vaginal *Lactobacillus* and a Nugent score of at least 4 further involves optionally administering a live bacterial composition comprising $H_2O_2$-producing vaginal *Lactobacillus*, in which the live bacterial composition is administered in an amount sufficient to promote growth of administered $H_2O_2$-producing vaginal *Lactobacillus*. In some embodiments, the $H_2O_2$-producing vaginal *Lactobacillus* is selected from the group consisting of *L. crispatus, L. jensenii, L. gasseri*, and combinations thereof. In some embodiments, the $H_2O_2$-producing vaginal *Lactobacillus* is *L. crispatus* CTV-05.

The following embodiments can be combined with any of the above aspects of the invention. For example, in some embodiments, the isolated peptide of the bacteriocin composition is SEQ ID NO:1 or SEQ ID NO:2 or SEQ ID NO:3 or SEQ ID NO:4. In some embodiments, the bacteriocin composition includes a combination of the isolated peptides SEQ ID NO:1 and SEQ ID NO:2. In some embodiments, the bacteriocin composition includes a combination of the isolated peptides SEQ ID NO:3 and SEQ ID NO:4. In some embodiments, the bacteriocin composition includes a combination of the isolated peptides SEQ ID NO:1, SEQ ID NO:2, SEQ ID NO:3, and SEQ ID NO:4.

In some embodiments, the formulation of the at least one pharmaceutically acceptable excipient and the at least one isolated peptide, or combination of isolated peptides, is a gel, cream, ointment, foam, film, capsule, tablet, powder, pessary, insert, or suppository suitable for topical intravaginal applications. In some embodiments, the amount of peptide, or combination of peptides, included in the bacteriocin composition is between 0.001% (w/w) and 3% (w/w). In some embodiments, the antibiotic is selected from the group consisting of clindamycin, metronidazole, secnidazole, tinidazole, and astodrimer sodium.

DETAILED DESCRIPTION OF THE INVENTION

I. Introduction

Figure 1:
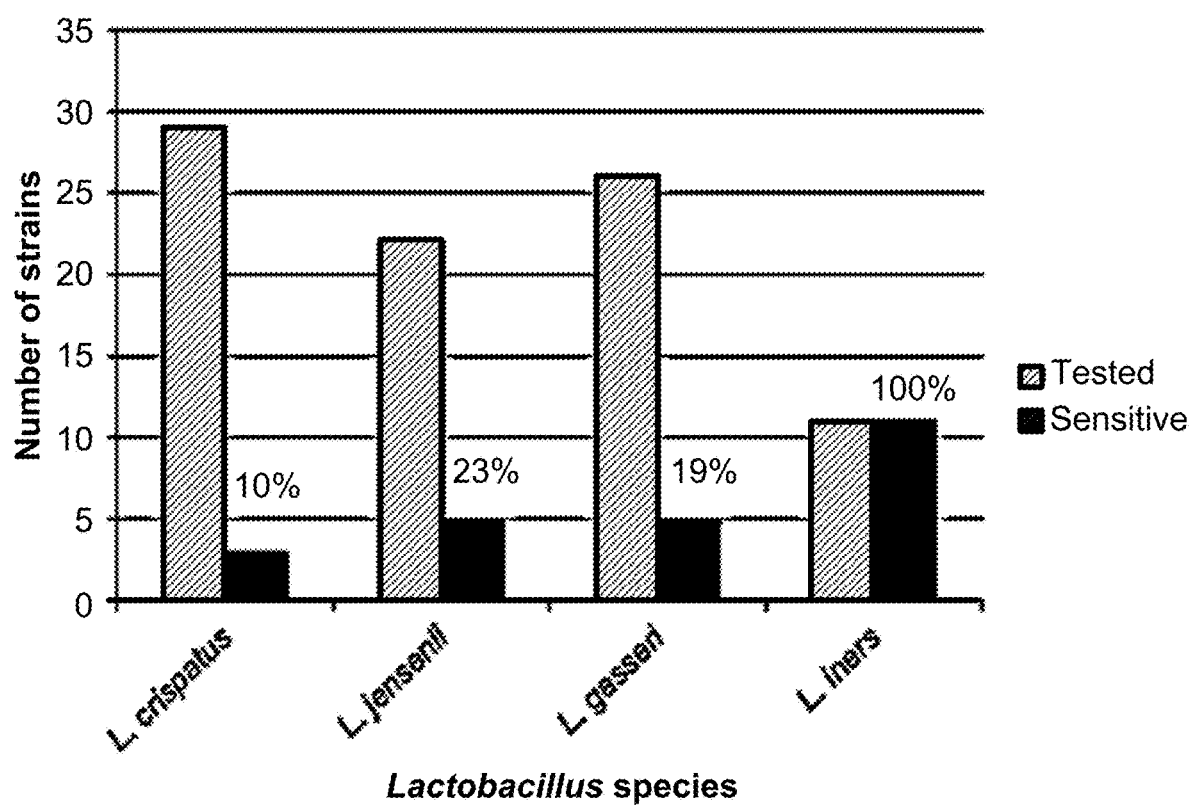
FIG. 1 shows sensitivity of strains of the major vaginal *Lactobacillus* species (*L. crispatus, L. jensenii, L. gasseri,* and *L. iners*) to inhibition by *L. paragasseri* K7 cell free culture supernatant.

This invention provides for a bacteriocin composition suitable for intravaginal administration where the composition selectively inhibits *L. iners*. Specifically, as disclosed herein, the present invention provides methods and compositions for treating women having low levels of $H_2O_2$-producing vaginal *Lactobacillus* and diverse microbiota associated with BV to selectively reduce the population of *L. iners* as a means to create an ecological niche for the colonization of vaginal mucosa by a *Lactobacillus* population that produces $H_2O_2$.

In other words, the invention described herein involves a replacement therapy for women diagnosed with having diverse microbiota associated with BV and low levels of $H_2O_2$-producing vaginal *Lactobacillus*, in which *L. iners*, which offers little resistance to BV-associated bacteria growth, is selectively reduced and replaced with protective $H_2O_2$-producing *Lactobacillus* that do offer resistance to BV-associated bacteria growth. As described in more detail below, the present invention teaches methods, compositions, and reagents for the preparation and use of bacteriocin formulations.

II. Definitions

As used herein, the term "bacteriocin composition" refers to a composition that functions to inhibit survival and/or growth of specific microorganisms. In particular, the bacteriocin composition will contain at least one isolated peptide of a bacteriocin, which has antibacterial activity against *L. iners*. Further, the bacteriocin composition will contain at least one pharmaceutically acceptable excipient. The bacteriocin composition of the present invention may be used for the prevention or treatment of various symptoms associated with BV. For the purposes of this invention, the bacteriocin compositions described herein are not suitable for oral administration.

As used herein, the term "bacteriocin" refers to peptides, complexed peptides, or proteins produced by particular strains of bacteria that are biologically active with bactericidal (i.e., antibacterial) action against other bacterial species. For example, bacteriocins GasK7A and GasK7B, are produced by bacterial strain *Lactobacillus* paragasseri K7, are biologically active with selective bactericidal activity against vaginal *L. iners*. Both K7A and K7B are two-component bacteriocins, meaning each bacteriocin has two peptides that confer maximal activity. The GasK7A bacteriocin is composed of the GasK7A α peptide (SEQ ID NO:3) and the GasK7A β peptide (SEQ ID NO:4); and the GasK7B bacteriocin is composed of the GasK7B α peptide (SEQ ID NO:1) and the GasK7B β peptide (SEQ ID NO:2). Bacterial species, and/or bacterial strains thereof, which are capable of producing bacteriocins are referred to as "bacteriocinogenic." Non-limiting examples of bacteriocinogenic species include particular strains of *Lactobacillus* paragasseri, *Lactobacillus gasseri*, and other species, the details of which are described herein. As such, in the context of the present disclosure, the term "bacteriocinogenic strains" is used to refer to the particular strains of bacterial species which are capable of producing bacteriocins. The term "*L. (para) gasseri*" is used herein to collectively refer to both *L. paragasseri* and *L. gasseri* species.

As used herein, the terms "isolated bacteriocin" or "isolated peptide" refers to a peptide that has been identified and separated, recovered, and/or purified from a component of its natural environment. In other words, an isolated bacteriocin or isolated peptide, in the context of the instant invention, is substantially free from the materials or contaminants with which the peptide or bacteriocin is normally associated in nature, in culture, or otherwise (e.g., synthetic). It is understood that the bacteriocin compositions described herein will contain at least one isolated peptide of a bacteriocin. As such, when referring to at the least one peptide, or a combination of peptides, in the context of the compositions and methods of the instant invention, it is understood that said peptide, or combination of said peptides, is an isolated peptide (e.g., an isolated peptide selected from the group consisting of SEQ ID NO:1, SEQ ID NO:2, SEQ ID NO:3, SEQ ID NO:4, and homologs thereof). For the purposes of this invention, the peptides of the bacteriocin compositions described herein are isolated peptides (e.g., purified).

As used herein, the term "pharmaceutically acceptable excipient" refers to any substance, or mixture of substances, used in the formulation of the bacteriocin compositions, which gives desirable physical characteristics to the bacteriocin composition formulations. The pharmaceutically acceptable excipients are, within the scope of sound medical judgment, suitable for contact with the mucosal tissues of human beings and aminals without excessive toxicity, irritation, allergic response, or other problem complications commensurate with a reasonable benefit/risk ratio. In some embodiments, the term "pharmaceutically acceptable" means approved by a regulatory agency of the Federal or a state government or listed in the U.S. Pharmacopeia or other generally recognized international pharmacopeia for use in animals, and more particularly in humans. Various pharmaceutically acceptable excipients can be used and are described in detail below.

As used herein, the phrase "selective bactericidal activity against *L. iners*" refers to the bactericidal activity exhibited by the bacteriocins (or peptides) that have been incorporated into the bacteriocin composition of the invention, in which at least one isolated peptide, or a combination of isolated peptides, selected from the group consisting of SEQ ID NO:1, SEQ ID NO:2, SEQ ID NO:3, SEQ ID NO:4, and homologs thereof, have a minimum inhibitory concentration (MIC) for *L. iners* that is at least 2 times less than the MIC for *L. crispatus* (SJ-3C), or at least 3 times less than, at least 4, 5, 6, 7, 8, 9, or at least 10 times less than the MIC for *L. crispatus* (SJ-3C).

As used herein, the terms "minimum inhibitory concentration" or "MIC" refer to the lowest concentration of the bacteriocin (i.e., the peptide or combination of peptides having bactericidal activity) that inhibits bacterial growth. In other words, the MIC is the amount of peptide or combination of peptides that is sufficient to exhibit antibacterial activity. The MIC of at least one peptide, or combination of peptides, selected from the group consisting of SEQ ID NO: 1, SEQ ID NO:2, SEQ ID NO:3, SEQ ID NO:4, and homologs thereof, is determined using methods described in detail below.

As used herein, the phrase "an amount sufficient to exhibit bactericidal properties" refers to the amount of the peptide or combination of peptides present in the bacteriocin composition of the invention that provides the composition with the ability to selectively inhibit and/or kill *L. iners*. The amount of peptide or combination of peptides of the bacteriocin composition is expressed as percent weight.

As used herein, the terms "percent weight" or "weight percentage" are used interchangeably, and, unless otherwise defined, refer to the percentage of a component (e.g., peptide or combination of peptides) measured in weight per total weight of a bacteriocin composition as a whole. Percent weight is represented by "%" or "% w/w." Bacteriocin compositions containing an isolated peptide, or combination of isolated peptides, selected from SEQ ID NO:1, SEQ ID NO:2, SEQ ID NO:3, SEQ ID NO:4, and homologs thereof, having weight percent values sufficient to exhibit bactericidal properties are described in detail below.

As used herein, the terms "identical," "percent sequence identity," or "percent homology," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region, e.g., the full-length of the sequence. Alignment for purposes of determining percent amino acid sequence identity can be performed in various methods, including those using publicly available computer software such as BLAST, BLAST-2, ALIGN or Megalign (DNASTAR) software. Optimal alignment of sequences for comparison may be conducted by the local homology algorithm of Smith and Waterman Add. *APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (CLUSTAL, GAP, BESTFIT, BLAST, FASTA, and TFASTA), or by inspection. Examples of algorithms that are suitable for determining percent sequence identity and sequence similarity for two sequences are the BLAST 2.0 algorithms, which are described in Altschul et al., Nuc. Acids Res. 25:3389-3402 (1977) and Altschul et al., J. Mol. Biol. 215:403-410 (1990). Clustal can be used to align more than two sequences. For purposes of this invention, BLAST 2.0 are used with the default parameters to determine percent sequence identity between a reference sequence and comparison sequence.

The terms "corresponding to," "determined with reference to," or "numbered with reference to" when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a peptide "corresponds to" an amino acid in the peptide of SEQ ID NO:1 when the residue aligns with the amino acid in SEQ ID NO:1 when optimally aligned to SEQ ID NO:1. The polypeptide that is aligned to the reference sequence need not be the same length as the reference sequence.

As used herein, the phrase "formulation suitable for intravaginal applications" refers to the route of administration where a substance (i.e., the bacteriocin composition) is applied inside the vagina. Such formulations are for the local administration to the vagina, preferably topical administration, such as, any external or internal surface of the female genitalia, including mucosal surfaces in the vaginal cavity and non-mucosal surfaces of the vulva and immediately surrounding areas of skin. The formulations are typically sterile, or near sterile. In general, non-sterile vaginal formulations have microbial limits of ≤200 CFU/g for total aerobic microbial count and ≤20 CFU/g for total combined yeasts and molds count, and absence of *Pseudomonas aeruginosa, Staphylococcus aureus,* and *Candida albicans.* Formulations suitable for intravaginal applications include, for example, a vaginal suppository, a capsule, a tablet, an insert, a cream, a salve, a gel, an ointment, a foam, a powder, an impregnated pad, a pessary, a spray, a lotion, a suspension, a douche preparation, or an impregnated or coated vaginally-insertable material such as a tampon.

As used herein, the term "antibiotic" refers to any therapeutic agent (e.g., an agent produced by microorganisms and/or synthetically) that has the capacity to inhibit the growth of and/or to kill one or more microorganisms (e.g., bacteria, fungi, parasites and the like). As used herein, antibiotics are well-known to those of skill in the art. Classes of antibiotics include, but are not limited to, aminoglycosides, amphenicols (e.g., chloramphenicol, thiamphenicol, azidamfenicol and the like), ansamycins (e.g., rifampin and the like), carbacephems, carbapenems, cephalosporins, glycopeptides (e.g., teicoplanin, vancomycin and the like), lincosamides (e.g., clindamycin, lincomycin and the like), macrolides (e.g., azithromycin, clarithromycin, dirithromycin, erythromycin, roxithromycin, troleandomycin, telithromycin, spectinomycin, quinupristin/dalfopristin, and the like), monobatams, nitrofurans (e.g., furazolidone, nitrofurantoin, nifurtoinol and the like), nitroimidazoles (e.g., metronidazole, seenidazole, tinidazol, nimorazole, omidazole, azanidazole and the like), oxazolidinones (e.g., linezolid, tedizolid and the like), penicillins, polypeptides (e.g., bacitracin, colistin, polymyxin B and the like), quinolones (e.g., ciprofloxacin, enoxacin, gatifloxacin, levofloxacin, lomefloxacin, moxifloxacin, norfloxacin, ofloxacin, trovafloxacin and the like), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines, and others (e.g., arsphenamine, ethambutol, fosfomycin, fusidic acid, isoniazid, mupirocin, platensimycin, pyrazinamide and the like). See, e.g., Robert Berkow (ed.) *The Merck Manual of Medical Information—Home Edition.* Pocket (September 1999), ISBN 0-671-02727-1.

Clindamycin, metronidazole, secnidazole, tinidazol, and VivaGel® (SPL-7013, or astodrimer sodium) are examples of antibiotics that are particularly active against *Gardnerella vaginalis, Atopobium vaginae,* and organisms within the Clostridiales order. Clindamycin, metronidazole, secnidazole, and tinidazol are particularly active against anaerobes, such as those found in BV. Astodrimer sodium (brand name: VivaGel®) is a water-based vaginal product of 1% (w/w) SPL-7013 mixed in Carbopol® gel buffered to a pH physiologically compatible with the normal human vagina. SPL-7013, the active ingredient of the astodrimer gel, is built from a divalent core, the benzhydrylamine amide of L-lysine, from which four successive layers of L-lysine branching units are added, creating the SPL-7013 dendrimer with 32 amine groups on the surface. A sodium 1-(carboxymethoxy) naphthalene-3,6-disulfonate group is attached to each of the 32 amine surface groups via amide linkers. The chemical product is N2,N6-bis(N2,N6-bis(N2, N6-bis(N2,N6-bis(N2,N6-bis((3,6-disulfonaphthalen-1-yloxy)acetyl)-1-lysyl)-1-lysyl)-1-lysyl)-1-lysyl)-N1-(diphenylmethyl)-1-lysinamide with a molecular weight of 16,581 daltons. (See, Rupp et al., 2007. VivaGel™ (SPL7013 Gel): A candidate dendrimer—microbicide for the prevention of HIV and HSV infection. *International Journal of Nanomedicine* 2(4):561-566).

As used herein, the phrase "diverse microbiota associated with BV" refers to a condition in which the vaginal mucosa lacks a sufficient amount of protective *Lactobacillus* spp. and is colonized by significant numbers of the less protective *Lactobacillus* species, *L. iners,* and diverse non-*Lactobacillus* spp., also referred to as "BV-associated organisms." Examples of non-*Lactobacillus* spp. associated with BV (i.e., BV-associated organisms) include, but are not limited to, *Gardnerella vaginalis, Atopobium vaginae, Leptotrichia amnionii, Eggerthella, Megasphaera* sp. type 1, *Dialister micaerophilus, Dialister* sp. 2, *Parvimonas micra, Prevotella buccalis, Prevotella timonensis, Prevotella bivia, Prevotella disiens, Porphyromonas asaccharolytica, Mycoplasma hominis,* and organisms within the Clostridiales order (e.g., BV-associated bacterium-1 (BVAB-1, BVAB-2 and BVAB-3). (See, Srinivasan et al., 2012. Bacterial Communities in Women with Bacterial Vaginosis: High Resolution Phylogenetic Analyses Reveal Relationships of Microbiota to Clinical Criteria *PLoS One* 7(6), Article No.: e37818). The condition can be symptomatic or asymptomatic. The term "vaginal microbiota" refers to the microorganisms of an ecosystem (i.e., the microorganisms that colonize the vagina). The term "vaginal microbiome" refers either to the collective genomes of the microorganisms in the ecological niche of the vagina or the microorganisms themselves.

As used herein, the terms "treating" or "treat" a patient having low levels $H_2O_2$-producing vaginal *Lactobacillus* and a Nugent score of at least 4 (i.e., a Nugent score of greater than or equal to 4) refers to increasing the levels of $H_2O_2$-producing vaginal *Lactobacillus,* decreasing the Nugent score to 0-3, reducing the severity of symptoms, and/or reducing the frequency of symptoms associated with diverse microbiota associated with BV.

As used herein, the phrase "$H_2O_2$-producing vaginal *Lactobacillus*" refers to "protective *Lactobacillus* spp.," a species of bacteria that are Gram-positive facultative anaerobic bacteria that produce lactate (lactic acid) from carbohydrate sources such as glucose, specifically characterized by the ability to produce $H_2O_2$. These $H_2O_2$-producing vaginal *Lactobacillus* are considered commensal organisms that colonize the vaginal mucosa. *L. crispatus, L. gasseri,* and *L. jensenii* are vaginal species capable of producing $H_2O_2$, as described in Antonio et al. *The Journal of Infectious Diseases* 1999, 180:1950-6. "Endogenous $H_2O_2$-producing vaginal *Lactobacillus*" refers to colonies of the protective *Lactobacillus* spp. that have originated from a patient's vaginal mucosa. "Administered $H_2O_2$-producing vaginal *Lactobacillus*" refers to the protective *Lactobacillus* spp. that have originated from a live bacterial composition administered to a patient's vaginal mucosa.

As used herein, the term "Nugent score" refers to a standard laboratory method for diagnosing BV in research settings, as described by Nugent et al. The Nugent score ranges from 0 to 10 and is calculated by manual microscopic evaluation of Gram-stained vaginal specimens and assessing relative concentration of *Lactobacillus* spp., Gram-negative and Gram-variable rods and cocci, and curved Gram-negative rods, which is described in detail below. (See, Nugent, R. P., Krohn, M. A, Hillier, S. L., 1991. Reliability of diagnosing bacterial vaginosis is improved by a standardized method of gram stain interpretation. *J Clin. Microbiol.* 29(2):297-301).

As used herein, the term "live bacterial composition" refers to a composition that contains at least one strain of live $H_2O_2$-producing vaginal *Lactobacillus* such as, for example, *L. crispatus, L. gasseri,* or *L. jensenii.* As a non-limiting example, useful *L. crispatus* strains include *Lactobacillus* crispatus CTV-05 and *Lactobacillus* crispatus SJ-3C. For the purposes of the instant invention, CTV-05 and SJ-3C are considered equivalent *L. crispatus* strains.

As used herein, the terms "about" and "approximately equal" are used herein to modify a numerical value and indicate a defined range around that value. If "X" is the value, "about X" or "approximately equal to X" generally indicates a value from 0.90X to 1.10X. Any reference to "about X" indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to disclose, e.g., "0.98X." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

As used herein, the terms "comprising" or "comprises" are intended to mean that the compositions and methods include the recited elements, but do not exclude others. "Consisting essentially of" refers to those elements required for a given embodiment. The phrase permits the presence of additional elements that do not materially affect the basic and novel or functional characteristic(s) of the given embodiment (e.g., compositions and methods). "Consisting of" refers to compositions, methods, and respective components thereof, as described herein, which are exclusive of any element not recited in that description of the embodiment. Embodiments defined by each of these transition terms are within the scope of this disclosure.

III. Bacteriocin Compositions

Bacteriocins

A peptide, or a combination of peptides, suitable for use in a bacteriocin composition of the present invention can be any peptide, or combination of peptides, having bactericidal activity against *L. iners*. In some embodiments, the peptides are bacteriocins that are classified as non-lantibiotics, or Class IIb bacteriocins, and are produced by strains of Gram-positive bacteria, including, for example, *Lactobacillus paragasseri*, *Lactobacillus gasseri*, and other species. The non-lantibiotics are a class of bacteriocins with non-modified residues except for the formation of disulfide bridges and circular bacteriocins. In some embodiments, non-lantibiotic bacteriocins useful for the instant invention are two-peptide bacteriocins, which belong to the bacteriocin subgroup, Class IIb. Class IIb bacteriocins consist of two-peptides whose full activity is dependent on the complementary action of the two different peptides (See, Nissen-Meyer J, Oppegard, C, Rogne, P, Haugen, H S, and Kristiansen, P E. 2010. Structure and Mode-of-Action of the Two-Peptide (Class-IIb) Bacteriocins. *Probiotics Antimicrob Proteins* 2:52-60.).

For example, the Class IIb (two-peptide) bacteriocins useful for the instant invention are those which are produced by the *Lactobacillus* paragasseri strain K7. *L. paragasseri* K7 produces bacteriocin gassericin K7A (GasK7A) and bacteriocin gassericin K7B (GasK7B), each consisting of two peptides, α and β. The DNA sequences encoding the α and β peptides of the GasK7A bacteriocin are defined under GenBank accession number ASRG02000001, with Protein ID KDA99706 corresponding to the GasK7A α peptide and Protein ID KDB00192 corresponding to the GasK7A β peptide. The DNA sequences encoding the α and β peptides of the GasK7B bacteriocin are defined under GenBank accession number ASRG02000002, with Protein ID KDA99085 corresponding to the GasK7B α peptide and Protein ID KDA99086 corresponding to the GasK7B β peptide. Another example of a Class IIb bacteriocin-producing bacterial strain is *L. gasseri* LF221, which produces bacteriocins acidocin LF221A and acidocin LF221B. It was previously determined that the DNA sequences of GasK7A and GasK7B were similar to the DNA sequences of acidocin LF221A and LF221B, respectively. That is, the bacteriocin GasK7A α and β peptide sequences are identical to the LF221A α and β peptide sequences (GenBank accession number AY295874; Protein IDs AAP55752 for partial LF221A α peptide sequence and AAP55753 for complete LF221A β peptide sequence). The bacteriocin GasK7B α and β peptide sequences are almost identical to the LF221B α and β peptide sequences (GenBank AY297947), except for one amino acid difference in both the α and β peptide homologs (Protein IDs AAP56344 and AAP56345 for LF221B α and LF221B β, respectively). (See, Peternel et al. 2010. Wide-Inhibitory Spectra Bacteriocins Produced by *Lactobacillus gasseri* K7. *Probiotics & Antimicro. Prot.* 2(4):233-240).

As such, peptides suitable for use in a bacteriocin composition of the present invention can be any peptide, or combination of peptides, which have been isolated from the above-identified IIb bacteriocins of *L. paragasseri* K7, or IIb bacteriocins with similar DNA and amino acid sequences to *L. paragasseri* K7, which have been produced by other *L. paragasseri* strains, *L. gasseri* strains (e.g., *L. gasseri* LF221), or strains of other bacterial species. Table 1 below includes an exemplary list of bacterial strains of *L. paragasseri*, *L. gasseri*, and other bacterial species having similar DNA and amino acid sequences to *L. paragasseri* K7 which encode similar or identical peptide sequences (i.e., homologs) of the GasK7A and/or GasK7B bacteriocin α and β peptides.

TABLE 1

Exemplary bacterial strains that encode homologs to the GasK7 bacteriocin peptides, with corresponding DNA (top line of each entry, coding region) and protein (bottom line of each entry) accession numbers from the GenBank database

| Bacterial Strain | GasK7A α peptide | GasK7A β peptide | GasK7B α peptide | GasK7B β peptide |
| --- | --- | --- | --- | --- |
| *L. paragasseri* K7 | ASRG02000001.1, 43641-43880 KDA99706.1 | ASRG02000001.1, 43880-44089 KDB00192.1 | ASRG02000002.1, 112159-112386 KDA99085.1 | ASRG02000002.1, 112396-112593 KDA99086.1 |
| *L. gasseri* 4M13 | CP021427.1, 1010027-1010266 ART98328.1 | CP021427.1, 1009818-1010027 ART98327.1 | CP021427.1, 327800-328027 ART97716.1 | CP021427.1, 327593-327790 ART97715.1 |
| *L. gasseri* JG141 | PQWW01000014.1, 56985-57224 RBQ00943.1 | PQWW01000014.1, 56776-56985 RBQ00942.1 | PQWW01000006.1, 97846-98073 RBQ01516.1 | PQWW01000006.1, 97639-97836 RBQ01515.1 |
| *L. gasseri* 505 | NZ_LZDT01000024.1, 39954-40193 WP_020807648.1 | NZ_LZDT01000024.1, 40193-40402 WP_020807649.1 | NZ_LZDT01000010.1, 751-978 WP_049159833.1 | NZ_LZDT01000010.1, 544-741 WP_003649213.1 |
| *L. paragasseri* JCM5344 | BEXI01000008.1, 43556-43795 GBA92003.1 | BEXI01000008.1, 43795-44004 GBA92006.1 | BEXI01000001.1, 223186-223413 GBA88916.1 | BEXI01000001.1, 222979-223176 GBA88913.1 |
| *L. gasseri* LF221 | AY295874.1, 1-116 AAP55752.1 | AY295874.1, 116-325 AAP55753.1 | AY297947.1, 869-1096 AAP56344.1 | AY297947.1, 1106-1303 AAP56345.1 |
| *L. gasseri* UMB0099 | PKKC01000003.1, 90087-90326 PKZ90469.1 | PKKC01000003.1, 89878-90087 PKZ90468.1 | PKKC01000001.1, 121544-121771 PKZ91008.1 | PKKC01000001.1, 121781-121978 PKZ91009.1 |

TABLE 1-continued

Exemplary bacterial strains that encode homologs to the GasK7 bacteriocin peptides, with corresponding DNA (top line of each entry, coding region) and protein (bottom line of each entry) accession numbers from the GenBank database

|  | GasK7A α peptide | GasK7A β peptide | GasK7B α peptide | GasK7B β peptide |
| --- | --- | --- | --- | --- |
| *L. paragasseri* JCM5343[T] | AP018549.1, 1877502-1877741<br>BBD49415.1 | AP018549.1, 1877741-1877950<br>BBD49416.1 | AP018549.1, 602448-602675<br>BBD48202.1 | AP018549.1, 602685-602882<br>BBD48203.1 |
| *L. paragasseri* JCM1130 | BEXG01000005.1, 42645-42884<br>GBA83318.1 | BEXG01000005.1, 42884-43093<br>GBA83321.1 | BEXG01000001.1, 121438-121665<br>GBA79835.1 | BEXG01000001.1, 121675-121872<br>GBA79838.1 |
| *L. gasseri* 105-1 | MK598475* | MK598475* | MK598476* | MK598476* |
| *L. gasseri* 151-2 | MK598477* | MK598477* | MK598478* | MK598478* |
| *L. gasseri* LA327 | LC389591.1, 162-401<br>BBE52938.1 | LC389591.1, 401-610<br>BBE52939.1 | LC389592.1, 5490-5717<br>BBE52947.1 | LC389592.1, 5727-5924<br>BBE52948.1 |
| *L. gasseri* 497_LGAS | NZ_JVEV01000010.1, 18351-18590<br>WP_049160225.1 | NZ_JVEV01000010.1, 18142-18351<br>WP_049160222.1 | NZ_JVEV01000006.1, 24402-24629<br>WP_049159833.1 | NZ_JVEV01000006.1, 24639-24836<br>WP_003649213.1 |
| *L. gasseri* LGs_Disk7 | NZ_MJET01000034.1, 128524-128763<br>WP_049160225.1 |  | NZ_MJET01000043.1, 98205-98432<br>WP_049159833.1 | NZ_MJET01000043.1, 97998-98195<br>WP_003649213.1 |
| *L. gasseri* G7 |  | KF724910.1, 31-240<br>AHE41136.1 | KF724911.1, 1-105<br>AHE41139.1 | KF724911.1, 115-312<br>AHE41138.1 |
| *L. gasseri* SBT2055 |  |  | AB029612.1, 1977-2204<br>BAA82353.1 | AB029612.1, 2214-2411<br>BAA82354.1 |
| *L. gasseri* LA158 |  |  | AB710328.1, 5490-5717<br>BAM09405.1 | AB710328.1, 5727-5924<br>BAM09406.1 |
| *L. paragasseri* JV-V03 |  |  | ACGO02000001.1, 1018849-1019076<br>EFJ70596.1 | ACGO02000001.1, 1018642-1018839<br>EFJ70595.1 |
| *L. gasseri* EV1461 |  |  | KR080485.1, 5475-5702<br>ALX37947.1 | KR080485.1, 5712-5909<br>ALX37948.1 |
| *L. gasseri* 987_LJOH |  |  | NZ_JUKW01000002.1, 64043-64270<br>WP_048684917.1 | NZ_JUKW01000002.1, 63836-64033<br>WP_003649213.1 |
| *L. gasseri* AL5 |  |  | MUJA01000002.1, 137439-137666<br>OOK86866.1 | MUJA01000002.1, 137676-137873<br>OOK86867.1 |
| *L. acidophilus* NCTC13720 |  |  | LR134325.1, 595510-595737<br>VEF35034.1 | LR134325.1, 595747-595944<br>VEF35035.1 |
| *L. gasseri* 7135 | SRLR01000080.1, 15139-15378<br>TQW12671.1 | SRLR01000080.1, 14930-15139<br>TQW12670.1 |  |  |
| *L. gasseri* UMB0056 | PNGR01000002.1, 42788-43027<br>PMC32163.1 | PNGR01000002.1, 43027-43236<br>PMC32164.1 |  |  |
| *L. gasseri* AL3 | MTZT01000002.1, 48178-48417<br>OOK96447.1 | MTZT01000002.1, 48417-48626<br>OOK96448.1 |  |  |
| *L. crispatus* G4 |  | KF724909.1, 33-242<br>AHE41134.1 |  |  |
| *L. gasseri* G3 |  | KF724908.1, 18-227<br>AHE41132.1 |  |  |
| Rodent Strains |  |  |  |  |
| *L. taiwanensis* 111z | NGOM01000011.1, 206480-206719<br>OYS21308.1 | NGOM01000011.1, 206271-206480<br>OYS21307.1 |  |  |
| *L. taiwanensis* 111w | NGON01000042.1, 206255-206494<br>OYS24304.1 | NGON01000042.1, 206046-206255<br>OYS24303.1 |  |  |
| *L. taiwanensis* 111u | NG0001000043.1, 260085-260324<br>OYS23267.1 | NG0001000043.1, 259876-260085<br>OYS23266.1 |  |  |
| *L. taiwanensis* 111o | NGOP01000022.1, 260145-260384<br>OYS26411.1 | NGOP01000022.1, 259936-260145<br>OYS26410.1 |  |  |
| *L. taiwanensis* 111m | NGOQ01000033.1, 260319-260558<br>OYS28529.1 | NGOQ01000033.1, 260110-260319<br>OYS28528.1 |  |  |
| *L. taiwanensis* 111k | NGOR01000022.1, 35996-36235<br>OYS30469.1 | NGOR01000022.1, 36235-36444<br>OYS30470.1 |  |  |
| *L. taiwanensis* 103q | NGOW01000011.1, 206489-206728<br>OYS39005.1 | NGOW01000011.1, 206280-206489<br>OYS39004.1 |  |  |
| *L. taiwanensis* 103n | NGOX01000022.1, 260031-260270<br>OYS42379.1 | NGOX01000022.1, 259822-260031<br>OYS42378.1 |  |  |

TABLE 1-continued

Exemplary bacterial strains that encode homologs to the GasK7 bacteriocin peptides, with corresponding DNA (top line of each entry, coding region) and protein (bottom line of each entry) accession numbers from the GenBank database

|  | GasK7A α peptide | GasK7A β peptide | GasK7B α peptide | GasK7B β peptide |
|---|---|---|---|---|
| *L. taiwanensis* 103j | NGOY01000043.1, 42754-42993<br>OYS40407.1 | NGOY01000043.1, 42545-42754<br>OYS40406.1 |  |  |
| *L. taiwanensis* 103a | NGOZ01000011.1, 260091-260330<br>OYS44979.1 | NGOZ01000011.1, 259882-260091<br>OYS44978.1 |  |  |
| *L. taiwanensis* 601c | NGOA01000043.1, 23293-23490<br>OYR98712.1 | NGOA01000043.1, 23490-23699<br>OYR98713.1 |  |  |
| *L. taiwanensis* 601a | NGOC01000056.1, 23296-23493<br>OYS02146.1 | NGOC01000056.1, 23493-23702<br>OYS02147.1 |  |  |
| *Bacillus aerius* CH2-D42-30 | RAZC01000031.1, 43664-43843<br>RKJ23393.1 | RAZC01000031.1, 43843-44052<br>RKJ23394.1 |  |  |

*Accession numbers corresponding to DNA sequences of clinical isolates from the Osel, Inc. strain collection Examples of bacteriocins having similar DNA sequences to *L. paragasseri* K7, which are encoded by other bacterial strains listed in Table 1, include: gassericin E from *L. gasseri* EV1461 (GenBank Accession No. KR080485; Protein IDs ALX37947 and ALX3748; See, Maldonado-Barragin, A. et al. (2016) *BMC Microbiology* 16:37); gassericin T from *L. gasseri* LA158 (AB710328, Protein IDs BAM09405 and BAM09406; See, Yasuta, N. et al., (2014) *Milk Science* 63:9-17; strain *L. gasseri* LA158 is publicly available from Japan Collection of Microorganisms under strain name JCM 11046) and *L. gasseri* SBT2055 (AB029612, Protein IDs BAA82353 and BAA82354; See, Kawai, Y. et al. (2000) *Biosci. Biotechnol. Biochem.* 64:2201-2208); and *L. gasseri* LF221, encoding acidocins LF221A (partial sequence) and LF221B (AY295874 and AY297947 for LF221A and LF221B, respectively; See, Majhenic et al, (2004) *Applied Microbiology and Biotechnology*, 63:705-714). *L. gasseri* LA327 (LC389591 and LC389592; Protein IDs BBE52938.1 and BBE52939.1: K7A homologs; Protein IDs BBE52947.1 and BBE52948.1: K7B homologs), and *L. gasseri* strains 105-1 (MK598475 and MK598476, no Protein IDs) and 151-2 (MK598477 and MK598478, no Protein IDs) encode homologs that are similar to bacteriocins GasK7A and GasK7B, while *L. paragasseri* JV-V03 (ACG002000001; Protein ID EFJ70596: K7B α homolog; Protein ID EFJ70595: K7B β homolog) encodes peptide homologs similar to bacteriocin GasK7B.

Suitable bacteriocinogenic strains of *L. paragasseri, L. gasseri*, and other bacterial species (such as, for example, those listed in Table 1) can be detected and isolated from natural sources using appropriate screening techniques that are known in the art. Bacteriocinogenic *L. paragasseri* K7 and *L. gasseri* LF221 were originally isolated from the feces of breast-fed human infants. Both bacteriocinogenic strains of *L. paragasseri* K7 and *L. gasseri* LF221 are deposited at the Microbial Collection of the Institute of Dairy Science, Biotechnical Faculty, University of Ljubljana, Slovenia. The *L. paragasseri* K7 strain is also deposited at the Czech Collection of Microorganisms (CCM) under Registration Number CCM 7710. (See, Matijasid et al., 1998. Isolation and characterization of two bacteriocins of *Lactobacillus acidophilus* LF221. *Appl Environ Microbiol* 49:606-612; Matijasid et al., 1999. Bacteriocinogenic activity of lactobacilli isolated from cheese and baby faeces. *Food Technol. Biotechnol.* 37:93-100; Rogelj et al., 2006. *Lactobacillus gasseri* LF221 and K7—from isolation to application. *Biologia* 61(6):761-769; Peternel et al. 2010. Wide-Inhibitory Spectra Bacteriocins Produced by *Lactobacillus gasseri* K7. *Probiotics & Antimicro. Prot.* 2(4):233-240; Mavrič, et al. 2014. Bacteriocins of *Lactobacillus gasseri* K7—Monitoring of gassericin K7 A and B genes' expression and isolation of active component. *Process Biochemistry* 49:1251-1259).

The bacteriocinogenic strains of *L. paragasseri, L. gasseri*, and other bacterial species useful for the present invention (e.g., *L. paragasseri* K7, *L. gasseri* JG141, *L. gasseri* 505, *L. paragasseri* JCM5344, or others listed in Table 1) can be propagated in liquid or on solid media (e.g., agar). Bacterial media for growing the bacteriocinogenic strains useful for the present invention (e.g., *L. (para)gasseri* strains and others listed in Table 1) are known and commercially available (e.g., from Becton Dickinson (Difco), Franklin Lakes, N.J. or Merck, Darmstadt, Germany) and include, e.g., de Man, Rogosa, and Sharpe (MRS) and Rogosa media. The bacteriocinogenic strains are preferably cultured anaerobically or microaerophilically and the temperature of the culture medium can be any temperature suitable for growth of the bacteriocinogenic strains. For example, bacteriocinogenic strains of *L. (para)gasseri* and other bacterial species useful for the present invention (i.e., *L. paragasseri* K7) can be propagated in microaerophilic conditions and are generally grown at about 37° C. Effective culture conditions for bacteriocinogenic strains useful for the instant invention are well known in the art. Specific culture conditions, culture media, and methods of culturing bacteriocinogenic strains, particularly *L. paragasseri* K7, can be found in, e.g., Matijasid et al., 2000. *Lactobacillus* K7—A New Candidate for a Probiotic Strain. *Food Technol. Biotechnol.* 38(2):113-119; Rogelj et al., 2006. *Lactobacillus gasseri* LF221 and K7—from isolation to application. Biologia 61(6):761-769; Peternel et al. 2010. Wide-Inhibitory Spectra Bacteriocins Produced by *Lactobacillus gasseri* K7. *Probiotics & Antimicro. Prot.* 2(4):233-240; Mavrič, et al. 2014. Bacteriocins of *Lactobacillus gasseri* K7—Monitoring of gassericin K7 A and B genes' expression and isolation of active component. *Process Biochemistry* 49:1251-1259).

The culture medium is inoculated with an actively growing culture of the bacteriocinogenic strain (e.g., a *L. (para) gasseri* strain) in an amount sufficient to produce, after a reasonable growth period, suitable bacteriocin activity that can be detected in the culture supernatant. A non-limiting example of a reasonable growth period of a bacteriocinogenic strain used herein (e.g., a *L. (para)gasseri* strain) is an incubation time of between 6 and 24 hours. The cells are incubated until the bacteriocin activity of the MRS culture broth is in the range of from about $10^2$ BU/mL to about $10^4$ BU/mL. One bacteriocin unit (BU) is the amount of bacteriocin causing 50% growth inhibition of a sensitive indicator strain as compared with a control without bacteriocin. Bacteriocin activity in the supernatant of bacteriocinogenic culture (e.g., the supernatant of bacteriocinogenic *L. (para) gasseri* culture) is measured by critical dilution method in a microtiter plate, using *Lactobacillus iners* strain LactinV 09V1-c, repository ID: BEI HM-702 (Biodefense and Emerging Infections Research Resources Repository, Manassas, Va.) and/or *Lactobacillus* sake NCDO 2714 (National Collection of Dairy Organisms, Reading, England) as indicator strains, and a microtiter plate reader as described in Matijasid et al., 1998. Isolation and characterization of two bacteriocins of *Lactobacillus acidophilus* LF221. *Appl Environ Microbiol* 49:606-612 and Matijasid et al., 2000. *Lactobacillus* K7—A New Candidate for a Probiotic Strain. *Food Technol. Biotechnol.* 38(2):113-119.

Once a suitable bacteriocin activity is established in the supernatant of the bacteriocinogenic culture broth, the cells of the bacteriocinogenic strain are removed from the bacteriocin supernatant via hollow fiber filtration methods (e.g., for larger scale) or centrifugation methods (e.g., for smaller scale). After separation of the supernatant from the bacterial cells, the bacteriocin molecules (e.g., GasK7A/GasK7B or homologs thereof) within the cell-free supernatant can be extracted and concentrated together by suitable means and methods known in the art. For example, the K7 bacteriocin molecules can be extracted together from the cell-free bacterial supernatant by sterile filtering the supernatant, absorbing the filtrate onto a suitable hydrophobic resin (e.g., Amberlite® XAD-16 resin, Sigma-Aldrich, St. Louis, Mo.), washing the resin with a suitable organic solvent or solvent mixture (e.g., ethanol, acetone, or chloroform), and eluting the K7 bacteriocins from the resin using a suitable organic solvent or solvent mixture (e.g., isopropanol, acetonitrile, trifluoroacetic acid). Alternatively, bacteriocins can be precipitated out from the bacterial culture supernatant by using ammonium sulfate "salting out" method, where a desired saturation percentage of salt is reached by adding ammonium sulfate slowly to the cell-free bacteriocin-containing culture supernatant. After incubating the salt suspension under suitable conditions, the salted-out bacteriocins can be collected by centrifugation, dissolved in a small volume of suitable solvent or buffer, and purified further.

Following extraction, the solvent in the bacteriocin-solvent mixture can be evaporated to concentrate the extracted bacteriocin peptides. The extracted and concentrated bacteriocin mixture can be referred to as "semi-purified." In some embodiments, the semi-purified bacteriocins can be incorporated directly into the bacteriocin composition of the invention as a four-peptide mixture (e.g., GasK7A α and GasK7A β peptides of bacteriocin GasK7A; and GasK7B α and GasK7B β peptides of bacteriocin GasK7B). In other embodiments, the semi-purified bacteriocins can be further purified and separated into individual peptide components, in which each peptide (e.g., GasK7A α, GasK7A β, GasK7B α, and GasK7B β is isolated and an individual peptide is incorporated into the bacteriocin composition, or a combination of the peptides is incorporated into the bacteriocin composition. Methods of separating and isolating the bacteriocins and bacteriocin peptides are described below, as well as a detailed description of the bacteriocin compositions of the invention.

Peptides of *L. paragasseri* K7 Bacteriocins and Homologs Thereof

Isolating and purifying the semi-purified bacteriocin mixture into individual peptide components typically involve chromatography-based methods. Based on the knowledge of the target bacteriocin characteristics such as its estimated size, molecule net charge at a definite pH, adsorption affinity, polarity and hydrophobicity, etc., different separation strategies can be used. The strategies include size exclusion, ion exchange, gel filtration, hydrophobic interaction, reverse phase liquid chromatography, etc. For example, a semi-purified bacteriocin extract can be passed through a size exclusion chromatography separation column and the mixture can be separated into fractions of different bacteriocin molecule sizes. Ion exchange chromatography, using either cation or anion exchange columns, can also be used to separate the semi-purified bacteriocin extracts based on their electric charge at a defined pH. In addition to the conventional chromatography columns, centrifuge-based protein separation cartridges are commercially available and can also be used for bacteriocin purification.

In some embodiments, reverse phase column chromatography is used to purify the bacteriocin peptides, using either low-pressure or high-pressure liquid chromatographic techniques. For example, after the GasK7A and GasK7B bacteriocin peptides are absorbed onto/extracted from a hydrophobic resin as described above, the eluent containing the semi-purified bacteriocin peptides (e.g., bacteriocins in isopropanol/trifluoroacetic acid solvent mixture) can be sterile filtered, diluted with a suitable solvent (e.g., 10-fold dilution in trifluoroacetic acid/water mixture), and loaded onto any suitable commercially available monosized polymeric matrix reverse phase column (e.g., GE Healthcare, Chicago, Ill. or Waters Corp., Milford, Mass., etc.). The bacteriocins can be stepwise or gradient eluted with varying solvent ratios of, for example, 2-propanol, water, and trifluoroacetic acid. The fractions containing the most bacteriocin activity can be further purified with low pressure reverse phase chromatography using an optimized solvent gradient. Solvent can be removed from each fraction by evaporation. The dried fractions can then be re-suspended in a suitable buffer (e.g. PBS or low EtOH) and subjected to bacteriocin activity testing via the critical dilution assay, as described above. The fractions obtained by elution with the optimized solvent mixture can then be processed for sodium dodecyl sulfate polyacrylamide gel electrophoresis (SDS-PAGE) and further bacteriocin activity testing, thereby confirming the separation of each bacteriocin peptide.

Following the purification procedures, the molecular weight and amino acid sequence of the bacteriocin peptides can be confirmed with precision using standard chemical analysis methods such as mass spectrometry and/or nuclear magnetic resonance (NMR) spectroscopy. For example, matrix-assisted laser desorption/ionization-time of flight (MALDI-TOF) mass spectrometric analysis can be used to confirm the molecular weight of the purified GasK7A α, GasK7A β, GasK7B α, and GasK7B β peptides. Determining the molecular weight of peptides using MALDI-TOF MS is well known to those skilled in the art. See, for example, Mavrič, et al. 2014. Bacteriocins of *Lactobacillus gasseri* K7—Monitoring of gassericin K7 A and B genes' expression and isolation of active component. *Process Biochemistry* 49:1251-1259. Below are the mature peptide sequences for the isolated GasK7A α, GasK7A β, GasK7B α, and GasK7B β peptides:

SEQ ID NO: 1 = K7B α
RNNWAANIGGAGGATVAGWALGNAVCGPACGFVGAHYVPIAWAGVTAATGG

FGKIRK

SEQ ID NO: 2 = K7B β
NKWGNAVIGAATGATRGVSWCRGFGPWGMTACGLGGAAIGGYLGYKSN

SEQ ID NO: 3 = K7A α
KNWSVAKCGGTIGTNIAIGAWRGARAGSFFGQPVSVGTGALIGASAGAIGG

SVQCVGWLAGGGR

SEQ ID NO: 4 = K7A β
NNVNWGSVAGSCGKGAVMEIYFGNPILGCANGAATSLVLQTASGIYKNYQK
KR

For the purposes of the instant invention, in addition to the above-identified amino acid sequence identities, the bacteriocin GasK7A α, GasK7A β, GasK7B α, and GasK7B β peptides are also defined by sequences having at least 80% sequence identity to one of SEQ ID NOs:1, 2, 3, or 4. As such, peptides suitable for use in a bacteriocin composition of the present invention can be any homolog of SEQ ID NO:1, SEQ ID NO:2, SEQ ID NO:3, or SEQ ID NO:4. In some embodiments, a peptide useful for the instant invention has 80% to 99% sequence identity to one of SEQ ID NOs:1, 2, 3, or 4. In some embodiments, a peptide useful for the instant invention has 85% to 99% sequence identity to one of SEQ ID NOs:1, 2, 3, or 4. In some embodiments, a peptide useful for the instant invention has 85% sequence identity to one of SEQ ID NOs:1, 2, 3, or 4, or 86%, 86.5%, 87%, 87.5%, 88%, 88.5%, 89%, 89.5%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, or 99% sequence identity to one of SEQ ID NOs:1, 2, 3, or 4. In some embodiments, a peptide useful for the instant invention has 88% to 98% sequence identity to one of SEQ ID NOs:1, 2, 3, or 4. In other embodiments, a peptide useful for the instant invention has 90% to 95% sequence identity to one of SEQ ID NOs:1, 2, 3, or 4. In other embodiments, a peptide useful for the instant invention has 90% sequence identity to one of SEQ ID NOs:1, 2, 3, or 4. In other embodiments, a peptide useful for the instant invention has 92.5% sequence identity to one of SEQ ID NOs:1, 2, 3, or 4. In other embodiments, a peptide useful for the instant invention has 95% sequence identity to one of SEQ ID NOs:1, 2, 3, or 4.

Table 2 below includes a list of exemplary bacterial strains of *L. paragasseri*, *L. gasseri*, and other bacterial species (presented previously in Table 1 and discussed above), with the homology that is shared between the peptide sequences encoded by each bacteriocinogenic strain and the GasK7 bacteriocin peptide sequences.

TABLE 2

Exemplary bacterial strains that encode homologs to the GasK7 bacteriocin peptide sequences and corresponding amino acid homology thereof

| | Amino Acid Homology to the K7 Bacteriocin Peptides | | | |
|---|---|---|---|---|
| Bacterial Strain | GasK7A α peptide | GasK7A β peptide | GasK7B α peptide | GasK7B β peptide |
| *L. paragasseri* K7 | 64/64 | 53/53 | 57/57 | 48/48 |
| 1 *L. gasseri* 4M13 | 64/64 | 53/53 | 56/57 | 48/48 |
| 2 *L. gasseri* JG141 | 64/64 | 53/53 | 56/57 | 48/48 |
| 3 *L. gasseri* 505 | 64/64 | 53/53 | 56/57 | 48/48 |
| 4 *L. paragasseri* JCM5344 | 64/64 | 53/53 | 56/57 | 48/48 |
| 5 *L. gasseri* LF221 | 37/37 (partial) | 53/53 | 56/57 | 47/48 |
| 6 *L. gasseri* UMB0099 | 63/64 | 52/53 | 56/57 | 48/48 |
| 7 *L. paragasseri* JCM5343 | 63/64 | 52/53 | 56/57 | 48/48 |
| 8 *L. paragasseri* JCM1130 | 63/64 | 52/53 | 56/57 | 48/48 |
| 9 *L. gasseri* 105-1 | 63/64 | 52/53 | 55/57 | 48/48 |
| 10 *L. gasseri* 151-2 | 63/64 | 52/53 | 55/57 | 48/48 |
| 11 *L. gasseri* LA327 | 63/64 | 51/53 | 56/57 | 48/48 |
| 12 *L. gasseri* 497_LGAS | 63/64 | 51/53 | 56/57 | 48/48 |
| 13 *L. gasseri* LGs_Disk7 | 63/64 | NS | 56/57 | 48/48 |
| 14 *L. gasseri* G7 | NS | 53/53 | 34/34 (partial) | 48/48 |
| 15 *L. gasseri* SBT2055 | NS | NS | 56/57 | 48/48 |
| 16 *L. gasseri* LA158 | NS | NS | 56/57 | 48/48 |
| 17 *L. paragasseri* JV-V03 | NS | NS | 55/57 | 48/48 |
| 18 *L. gasseri* EV1461 | NS | NS | 55/57 | 48/48 |
| 19 *L. gasseri* 987_LJOH | NS | NS | 55/57 | 48/48 |
| 20 *L. gasseri* AL5 | NS | NS | 55/57 | 48/48 |
| 21 *L. acidophilus* NCTC13720 | NS | NS | 55/57 | 48/48 |
| 22 *L. gasseri* 7135 | 63/64 | 52/53 | NS | NS |
| 23 *L. gasseri* UMB0056 | 63/64 | 52/53 | NS | NS |
| 24 *L. gasseri* AL3 | 63/64 | 52/53 | NS | NS |
| 25 *L. crispatus* G4 | NS | 53/53 | NS | NS |
| 26 *L. gasseri* G3 | NS | 52/53 | NS | NS |
| Rodent Strains | | | | |
| 27 *L. taiwanensis* 111z | 63/64 | 52/53 | NS | NS |
| 28 *L. taiwanensis* 111w | 63/64 | 52/53 | NS | NS |
| 29 *L. taiwanensis* 111u | 63/64 | 52/53 | NS | NS |
| 30 *L. taiwanensis* 111o | 63/64 | 52/53 | NS | NS |
| 31 *L. taiwanensis* 111m | 63/64 | 52/53 | NS | NS |
| 32 *L. taiwanensis* 111k | 63/64 | 52/53 | NS | NS |
| 33 *L. taiwanensis* 103q | 63/64 | 52/53 | NS | NS |
| 34 *L. taiwanensis* 103n | 63/64 | 52/53 | NS | NS |

TABLE 2-continued

Exemplary bacterial strains that encode homologs to the GasK7 bacteriocin peptide sequences and corresponding amino acid homology thereof Amino Acid Homology to the K7 Bacteriocin Peptides

| | | GasK7A α peptide | GasK7A β peptide | GasK7B α peptide | GasK7B β peptide |
|---|---|---|---|---|---|
| 35 | *L. taiwanensis* 103j | 63/64 | 52/53 | NS | NS |
| 36 | *L. taiwanensis* 103a | 63/64 | 52/53 | NS | NS |
| 37 | *L. taiwanensis* 601c | 62/64 | 52/53 | NS | NS |
| 38 | *L. taiwanensis* 601a | 62/64 | 52/53 | NS | NS |
| 39 | *Bacillus aerius* CH2-D42-30 | 44/64 (gap) | 52/53 | NS | NS |

NS = no sequence

Table 3 below includes amino acid sequence alignments of the peptide homologs produced from the bacteriocinogenic strains of Table 2 for each of the four GasK7A α (SEQ ID NO:3), GasK7A β (SEQ ID NO:4), GasK7B α (SEQ ID NO:1), and GasK7B β (SEQ ID NO:2) peptides. For the encoded peptide sequence alignments shown below in Table 3, the homolog-producing bacteriocinogenic strains are referred to by their corresponding numbers previously shown in Table 2. For example, bacterial strains 1, 2, 3, and 4 (i.e., 1-4) correspond to *L. gasseri* 4M13, *L. gasseri* JG141, *L. gasseri* 505, and *L. paragasseri* JCM5344, respectively (see, Table 2). These sequence alignments of Table 3 show particular polymorphic sites within the GasK7A and GasK7B peptides.

TABLE 3

Amino acid sequence alignments of the peptide homologs produced from bacterial strains for each of the four GasK7A α, GasK7A β, GasK7B α, and GasK7B β peptides

| SEQ ID | Encoded Peptide Sequence | Strains |
|---|---|---|

GasK7A α peptide homologs:

| SEQ ID NO: 3 | KNWSVAKCGGTIGTNIAIGAWRGARAGSFFGQPVSVGTGALIGASAGAIGGSVQCVGWLAGGGR | K7 1-4 |
| SEQ ID NO: 5 | KNWSVAKCGGTIGTNIAIGAWRGARAGSFFGQPVSVGAGALIGASAGAIGGSVQCVGWLAGGGR | 6-13 22-24 27-36 |
| SEQ ID NO: 6 | ENWSVAKCGGTIGTNIAIGAWRGARAGSFFGQPVSVGAGALIGASAGAIGGSVQCVGWLAGGGR | 37 38 |
| SEQ ID NO: 7 |                             SFFGQPVSVGTGALIGASAGAIGGSVQCVGWLAGGGR | 5 |
| SEQ ID NO: 8 | KNWSVAKCGGTIGTNIAIGAWRGAR--------------------AGAIGGSVQCVGWLAGGGR | 39 |

GasK7A β peptide homologs:

| SEQ ID NO: 4 | NNVNWGSVAGSCGKGAVMEIYFGNPILGCANGAATSLVLQTASGIYKNYQKKR | K7 1-5 14 25 |
| SEQ ID NO: 9 | NNVNWGSVAGSCGKGAVMGIYFGNPILGCANGAATSLVLQTASGIYKNYQKKR | 6-10 22-24 26 27-39 |
| SEQ ID NO: 10 | NNVNWGSVAGSCGKGAVMGIYFGNPILGCANGAATSLVLQTTSGIYKNYQKKR | 11 12 |

GasK7B α peptide homologs:

| SEQ ID NO: 1 | RNNWAANIGGAGGATVAGWALGNAVCGPACGFVGAHYVPIAWAGVTAATGGFGKIRK | K7 1-8 11-13 15-16 |
| SEQ ID NO: 11 | RNNWAANIGGVGGATVAGWALGNAVCGPACGFVGAHYVPIAWAGVTAATGGFGKIRK | |
| SEQ ID NO: 12 | RNNWAANIGGVGGATVAGWALGNAVCGPACGFVGEHYVPIAWAGVTAATGGFGKIRK | 9 10 17 |
| SEQ ID NO: 13 | RNNLAANIGGVGGATVAGWALGNAVCGPACGFVGAHYVPIAWAGVTAATGGFGKIRK | 18-21 |
| SEQ ID NO: 14 |                     AVCGPACGFVGAHYVPIAWAGVTAATGGFGKIRK | 14 |

GasK7B β peptide homologs:

| SEQ ID NO: 2 | NKWGNAVIGAATGATRGVSWCRGFGPWGMTACGLGGAAIGGYLGYKSN | K7 1-4 6-21 |
| SEQ ID NO: 15 | NKWGNAVIGAATGATRGVSWCRGFGPWGMTACALGGAAIGGYLGYKSN | 5 |

The bacteriocin peptides of this invention are further defined by a combination of their bactericidal activity and by their ability to bind to polyclonal or monoclonal antibodies generated against the prototype protein SEQ ID NOs:1-4. Under designated immunoassay conditions, the specified antibodies bind to a particular protein at least two times the background and do not substantially bind in a significant amount to other proteins present in the sample. For example, polyclonal antibodies raised to the K7B α peptide, encoded in SEQ ID NO:1, sequence variants, or portions thereof, can be selected to obtain only those polyclonal antibodies that are specifically immunoreactive with that peptide and not with other proteins, except for polymorphic variants of K7B α. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically, a specific or selective reaction will be at least twice background signal or noise and more typically more than 10 to 100 times background.

In some embodiments, the at least one isolated peptide, or combination of isolated peptides, selected from the group consisting of SEQ ID NO:1, SEQ ID NO:2, SEQ ID NO:3, SEQ ID NO:4, and homologs thereof, can be obtained by extraction and purification from a natural source, as described in detail above, or by any alternative means known in the art, such as, for example, by expression of a recombinant nucleic acid encoding the peptide (for example, in a cell or in a cell-free translation system); or by enzymatically or chemically synthesizing the peptide. In addition, an isolated bacteriocin peptide may be obtained by cleaving full-length peptides. When the peptide is a fragment of a larger naturally occurring peptide, the isolated peptide is shorter than and excludes the full-length, naturally-occurring peptide of which it is a fragment.

For example, the isolated peptides for use in the compositions and methods of the instant invention can be prepared by using any number of chemical polypeptide synthesis techniques well-known to those of ordinary skill in the art. For example, solution phase peptide synthesis can be used to construct peptides of moderate size or, for the chemical construction of peptides, solid phase synthesis can be employed. Atherton et al. (1981) Hoppe Seylers Z. Physiol. Chem. 362:833-839. The isolated bacteriocin peptides can be synthetically produced by linking two or more peptides or polypeptides together by protein chemistry techniques. For example, peptides can be chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). One skilled in the art can readily appreciate that a peptide corresponding to a bacteriocin useful for the present invention, for example, can be synthesized by standard chemical reactions.

For example, enzymatic ligation of cloned or synthetic peptide segments allows relatively short peptide fragments to be joined to produce larger peptide fragments or bacteriocin peptides. See, e.g., Abrahmsen L et al., *Biochemistry*, 30:4151 (1991). Proteolytic enzymes can also be utilized to couple amino acids to produce peptides. See, e.g., Kullmann (1987) Enzymatic Peptide Synthesis, CRC Press, Inc. Alternatively, native chemical ligation of synthetic peptides can be utilized to synthetically construct large peptides or polypeptides from shorter peptide fragments. This method consists of a two-step chemical reaction (Dawson et al. Synthesis of Proteins by Native Chemical Ligation. Science, 266:776-779 (1994)). The first step is the chemoselective reaction of an unprotected synthetic peptide-alpha-thioester with another unprotected peptide segment containing an amino-terminal Cys residue to give a thioester-linked intermediate as the initial covalent product. Without a change in the reaction conditions, this intermediate undergoes spontaneous, rapid intra-molecular reaction to form a native peptide bond at the ligation site. Application of this native chemical ligation method to the total synthesis of a peptide molecule is illustrated by the preparation of human interleukin 8 (IL-8) (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

In some embodiments, the isolated peptide can be obtained by using the biochemical machinery of a cell, or by isolation from a biological source. As such, recombinant DNA techniques can be employed for the production of the peptides. See, e.g., Hames et al. (1987) Transcription and Translation: A Practical Approach, IRL Press. Additional examples of appropriate cloning and sequencing techniques, and instructions sufficient to direct persons of skill through many cloning exercises are found in Sambrook et al. (2001) Molecular Cloning—A Laboratory Manual (3rd ed.) Vol. 1-3, Cold Spring Harbor Laboratory, Cold Spring Harbor Press, NY, (Sambrook). Peptides can also be isolated using standard techniques such as affinity chromatography.

Selective Bactericidal Activity of Bacteriocin Peptides

The bactericidal activity of an isolated peptide, or a combination of isolated peptides, selected from the group consisting of SEQ ID NO:1, SEQ ID NO: 2, SEQ ID NO:3, SEQ ID NO:4, and homologs thereof, is tested by determining the minimum inhibitory concentration (MIC) for each peptide or peptide combination. For the purposes of the instant invention, the bacteriocin peptides are tested for selective bactericidal activity against *L. iners* using in vitro assays to determine the comparative MIC of the bacteriocin peptides, or combinations thereof. The comparative MIC of the bacteriocin peptides, or combinations thereof, can be determined by monitoring the growth of an indicator strain in a multi-well microtiter plate, as described above and in Matijasid et al., 2000. *Lactobacillus* K7—A New Candidate for a Probiotic Strain. *Food Technol. Biotechnol.* 38(2):113-119. Semi-purified bacteriocin mixtures, the purified peptides, or combinations of purified peptides, can be used in the MIC assays.

In some embodiments, the peptides, or combinations thereof, which have selective bactericidal activity against *L. iners* will have a MIC for *L. iners* that is at least 2 times less than the MIC for the protective *Lactobacillus* sp., *L. crispatus* (SJ-3C). That is, the concentration of the isolated peptide, or the combination of isolated peptides, selected from the group consisting of SEQ ID NO:1, SEQ ID NO:2, SEQ ID NO:3, SEQ ID NO:4, and homologs thereof, that prevents the growth of *L. iners* is at least 2 times less than the concentration of the peptides or peptide combination that prevents the growth of *L. crispatus*. In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is at least 2 times less than the MIC for *L. crispatus* (SJ-3C), or at least 3 times less than, or at least 4, 5, 6, 7, 8, 9, or at least 10 times less than the MIC for *L. crispatus* (SJ-3C). In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is about 2 times less than the MIC for *L. crispatus* (SJ-3C), or about 3 times less than, or about 4, 5, 6, 7, 8, 9, or about 10 times less than the MIC for *L. crispatus* (SJ-3C).

In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is at least 5 times less than the MIC for *L. crispatus* (SJ-3C). In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is about 5 times less than the MIC for *L. crispatus* (SJ-3C). In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is at least 10 times less than the MIC for *L. crispatus* (SJ-3C). In some embodiments, the at least one peptide, or combination of peptides, selected from the group consisting of SEQ ID NO:1, SEQ ID NO:2, SEQ ID NO:3, SEQ ID NO:4, and homologs thereof, have a MIC for *L. iners* that is about 10 times less than the MIC for *L. crispatus* (SJ-3C). In some embodiments, the at least one peptide, or combination of peptides, selected from the group consisting of SEQ ID NO: 1, SEQ ID NO:2, SEQ ID NO:3, SEQ ID NO:4, and homologs thereof, have a MIC for *L. iners* that is more than 10 times less than the MIC for *L. crispatus* (SJ-3C).

In some embodiments, the at least one bacteriocin peptide, or combination of peptides, selected from the group consisting of SEQ ID NO:1, SEQ ID NO:2, SEQ ID NO:3, SEQ ID NO:4, and homologs thereof, will have a MIC against *L. iners* of between about 10 ng/mL and 600 ng/mL. In some embodiments, the at least one bacteriocin peptide, or combination of peptides, selected from the group consisting of SEQ ID NO:1, SEQ ID NO:2, SEQ ID NO:3, SEQ ID NO:4, and homologs thereof, will have a MIC against *L. iners* of about 10 ng/mL, or about 15, 20, 25, 30, 60, 75, 100, 150, 200, 250, 300, 350, 400, 450, 500, 550, or 600 ng/mL. In other embodiments, the at least one bacteriocin peptide, or combination of peptides, selected from the group consisting of SEQ ID NO:1, SEQ ID NO:2, SEQ ID NO:3, SEQ ID NO:4, and homologs thereof, will have a MIC against *L. iners* of between about 15 ng/mL and 450 ng/mL, or about 20 ng/mL and about 300 ng/mL, or about 25 ng/mL and about 200 ng/mL. In some embodiments, the at least one bacteriocin peptide, or combination of peptides, selected from the group consisting of SEQ ID NO:1, SEQ ID NO:2, SEQ ID NO:3, SEQ ID NO:4, and homologs thereof, will have a MIC against *L. iners* of between about 25 ng/mL and 150 ng/mL. In other embodiments, the at least one bacteriocin peptide, or combination of peptides, selected from the group consisting of SEQ ID NO: 1, SEQ ID NO:2, SEQ ID NO:3, SEQ ID NO:4, and homologs thereof, will have a MIC against *L. iners* of about 25 ng/mL.

In some embodiments, the bacteriocin peptide that can be incorporated into the bacteriocin composition of the invention is a peptide of SEQ ID NO:1, or a homolog thereof. In some embodiments, the peptide that can be incorporated into the bacteriocin composition is a peptide of SEQ ID NO:2, or a homolog thereof. In other embodiments, the peptide that can be incorporated into the bacteriocin composition is a peptide of SEQ ID NO:3, or a homolog thereof. In some embodiments, the peptide that can be incorporated into the bacteriocin composition is a peptide of SEQ ID NO:4, or a homolog thereof.

In some embodiments, a combination of the peptides SEQ ID NO:1, SEQ ID NO:2, SEQ ID NO:3, or SEQ ID NO:4, or homologs thereof, will exhibit synergistic bactericidal activity, in which the MIC of a suitable peptide combination will be lower than the MIC of individual peptides. In other words, the selective bactericidal activity against *L. iners* of a suitable peptide combination can be greater than the selective bactericidal activity against *L. iners* of an individual peptide. Without wishing to be bound by any theory, incorporating synergistic mixtures of the peptides SEQ ID NO:1, SEQ ID NO:2, SEQ ID NO:3, or SEQ ID NO:4, or homologs thereof, within the bacteriocin compositions of the invention may prevent development of resistance in the target *L. iners* organism.

In some embodiments, a suitable combination of the peptides SEQ ID NO:1, SEQ ID NO:2, SEQ ID NO:3, or SEQ ID NO:4, or homologs thereof, will have a MIC against *L. iners* of between about 0.01 ng/mL and 100 ng/mL. In some embodiments, a suitable combination of the peptides SEQ ID NO:1, SEQ ID NO:2, SEQ ID NO:3, or SEQ ID NO:4, or homologs thereof, will have a MIC against *L. iners* of about 0.01 ng/mL, or about 0.025, 0.05, 0.075, 0.1, 0.25, 0.5, 0.75, 1, 1.5, 2, 2.5, 3, 4, 5, 6, 7, 8, 10, 15, 20, 25, 30, 40, 50, 60, 70, 80, 90 or 100 ng/mL. In other embodiments, a suitable combination of the peptides SEQ ID NO: 1, SEQ ID NO:2, SEQ ID NO:3, or SEQ ID NO:4, or homologs thereof, will have a MIC against *L. iners* of between about 0.025 ng/mL and 80 ng/mL, about 0.05 ng/mL and 75 ng/mL, about 0.075 ng/mL and 60 ng/mL, about 0.1 ng/mL and 50 ng/mL, about 0.25 ng/mL and 30 ng/mL, about 0.5 ng/mL and 25 ng/mL, about 0.75 ng/mL and 20 ng/mL, about 1 ng/mL and 18 ng/mL, or about 1.5 ng/mL and about 15 ng/mL, or about 3 ng/mL and about 10 ng/mL. In some embodiments, a suitable combination of the peptides SEQ ID NO:1, SEQ ID NO:2, SEQ ID NO:3, or SEQ ID NO:4, or homologs thereof, will have a MIC against *L. iners* of between about 0.1 ng/mL and 5 ng/mL. In other embodiments, a suitable combination of the peptides SEQ ID NO:1, SEQ ID NO:2, SEQ ID NO:3, or SEQ ID NO:4, or homologs thereof, will have a MIC against *L. iners* of about 1.5 ng/mL.

In some embodiments, the synergy between two or more peptides of SEQ ID NO:1, SEQ ID NO:2, SEQ ID NO:3, or SEQ ID NO:4, or homologs thereof, can be determined using methods known in the art. For example, synergistic activity could be determined using the Fractional Inhibitory Concentration (FIC) index by a broth microdilution method (See, U.S. Patent Application No. US 2015/0072920 A1; Antimicrobial Susceptibility Testing Protocols. 2007. Kindle Edition Richard Schwalbe (Editor), Lynn Steele-Moore (Editor), Avery C. Goodwin (Editor) CRC Press, NY, USA). According to this method, a combination having a FIC index <0.5 is considered as synergistic, a combination having 0.5<FIC index ≤1 is considered as moderate synergistic, a combination having a 1.0<FIC index ≤4.0 is considered as indifferent and a combination having a FIC index >4 is considered an antagonist. In some embodiments, the peptide combination can have a moderate or a high synergistic effect as determined by the FIC method. In some embodiments, the peptide combination can be combined at lower than their MICs. In some embodiments, the peptide combination having a synergistic effect allows the use of lower concentration of each bacteriocin peptide.

In some embodiments, the combination of bacteriocin peptides that can be incorporated into the bacteriocin composition of the invention includes a peptide of SEQ ID NO:1, or a homolog thereof, and a peptide of SEQ ID NO:2, or a homolog thereof. In some embodiments, the combination of bacteriocin peptides that can be incorporated into the bacteriocin composition of the invention includes a peptide of SEQ ID NO:1, or a homolog thereof, and a peptide of SEQ ID NO:4, or a homolog thereof. In other embodiments, the combination of bacteriocin peptides that can be incorporated into the bacteriocin composition of the invention includes a peptide of SEQ ID NO:2, or a homolog thereof, and a peptide of SEQ ID NO:3, or a homolog thereof. In other embodiments, the combination of bacteriocin peptides that can be incorporated into the bacteriocin composition of the invention includes a peptide of SEQ ID NO:3, or a homolog thereof, and a peptide of SEQ ID NO:4, or a homolog thereof. In other embodiments, the combination of bacteriocin peptides that can be incorporated into the bacteriocin composition of the invention includes a peptide of SEQ ID NO:1, a peptide of SEQ ID NO:2, a peptide of SEQ ID NO:3, and a peptide of SEQ ID NO:4, or homologs thereof.

Intravaginal Formulations of Bacteriocin Compositions

The amount of the at least one isolated bacteriocin peptide, or a combination of isolated peptides, of SEQ ID NO: 1, SEQ ID NO:2, SEQ ID NO:3, SEQ ID NO:4, or homologs thereof, or peptide mixture (e.g., SEQ ID NO: 1, SEQ ID NO:2, SEQ ID NO: 3, and/or SEQ ID NO:4) present in the bacteriocin compositions of the instant invention will be in an amount sufficient for the composition as a whole to exhibit bactericidal properties. The amount of the at least one peptide or combination of peptides to include in the bacteriocin compositions will be a MIC or percentage (w/w %) that is large enough to account for potential interactions between the pharmaceutically acceptable excipients, in vivo protein binding, and potential in vivo metabolic breakdown, while still exhibiting selective bactericidal activity against *L. iners*. As such, in vitro MIC of the peptides and peptide combinations having selective bactericidal activity against *L. iners* described above will not be the same for in vivo applications. For in vivo applications, the amount of the bacteriocin or peptide mixture within the bacteriocin composition will be a minimum inhibitory concentration that is between about 10-fold to about 10,000-fold higher concentration than the in vitro MIC. In some embodiments, the amount of the bacteriocin or peptide mixture within the bacteriocin composition for in vivo applications will be a MIC that is about 10-fold higher concentration than the in vitro MIC, or about 50-fold, 75-fold, 100-fold, 200-fold, 500-fold, 1000-fold, 2000-fold, 3000-fold, 4000-fold, 5000-fold, 6000-fold, 7000-fold, 8000-fold, 9000-fold or about 10,000-fold higher concentration than the in vitro MIC. In some embodiments, the amount of the bacteriocin or peptide mixture within the bacteriocin composition for in vivo applications will be a MIC that is between about 15-fold higher to 9000-fold higher concentration than the in vitro MIC, or about 30-fold to about 8000-fold higher, or about 60-fold to about 6000-fold higher, or about 100-fold to about 5000-fold higher, or about 200-fold to about 1000-fold higher, or about 250-fold higher to about 500-fold higher concentration than the in vitro MIC.

In some embodiments, the amount of the at least one bacteriocin peptide, or combination of peptides, selected from the group consisting of SEQ ID NO: 1, SEQ ID NO:2, SEQ ID NO:3, SEQ ID NO:4, and homologs thereof, present in the bacteriocin composition is a MIC, or dosage unit, of between about 1 µg/mL and 50 mg/mL. In some embodiments, the bacteriocin composition of the present invention comprises about 1 µg/mL of at least one bacteriocin peptide, or combination of peptides, selected from the group consisting of SEQ ID NO: 1, SEQ ID NO:2, SEQ ID NO:3, SEQ ID NO:4, and homologs thereof, or about 5 µg/mL, 6 µg/mL, 7 µg/mL, 8 µg/mL, 9 µg/mL, 10 µg/mL, 15 µg/mL, 20 µg/mL, 30 µg/mL, 40 µg/mL, 50 µg/mL, 75 µg/mL, 0.1 mg/mL, 0.5 mg/ml, 1 mg/mL, 5 mg/mL, 10 mg/mL, 20 mg/mL, 30 mg/mL, 40 mg/mL, or about 50 mg/mL of the at least one bacteriocin peptide or peptide mixture. In other embodiments, the bacteriocin composition of the present invention comprises about 1 µg/mL to about 45 mg/mL of at least one bacteriocin peptide, or combination of peptides, selected from the group consisting of SEQ ID NO:1, SEQ ID NO:2, SEQ ID NO:3, SEQ ID NO:4, and homologs thereof, or about 3 µg/mL to about 35 mg/mL of the at least one bacteriocin peptide or peptide mixture, or 5 µg/mL to about 25 mg/mL of the at least one bacteriocin peptide or peptide mixture, or 10 µg/mL to about 20 mg/mL, or 50 µg/mL to about 15 mg/mL, or 75 µg/mL to about 10 mg/mL, or 0.1 mg/mL to about 5 mg/mL, or 1 mg/mL to about 3 mg/mL of the at least one bacteriocin peptide or peptide mixture. In other embodiments, the bacteriocin composition of the present invention comprises about 30 mg/mL of at least one bacteriocin peptide, or combination of peptides, selected from the group consisting of SEQ ID NO:1, SEQ ID NO:2, SEQ ID NO:3, SEQ ID NO:4, and homologs thereof. In other embodiments, the bacteriocin composition of the present invention comprises about 10 mg/mL of at least one bacteriocin peptide, or combination of peptides, selected from the group consisting of SEQ ID NO:1, SEQ ID NO:2, SEQ ID NO:3, SEQ ID NO:4, and homologs thereof. In other embodiments, the bacteriocin composition of the present invention comprises about 1 mg/mL of at least one bacteriocin peptide, or combination of peptides, selected from the group consisting of SEQ ID NO:1, SEQ ID NO:2, SEQ ID NO:3, SEQ ID NO:4, and homologs thereof.

In some embodiments, the bacteriocin composition of the present invention comprises from about 0.0001% to about 5% of at least one bacteriocin peptide, or combination of peptides, selected from the group consisting of SEQ ID NO:1, SEQ ID NO:2, SEQ ID NO:3, SEQ ID NO:4, and homologs thereof. In some embodiments, the bacteriocin composition of the present invention comprises about 0.0001% of at least one bacteriocin peptide, or combination of peptides, selected from the group consisting of SEQ ID NO:1, SEQ ID NO:2, SEQ ID NO:3, SEQ ID NO:4, and homologs thereof, or about 0.0005, 0.0006, 0.0007, 0.0008, 0.0009, 0.001, 0.0015, 0.0025, 0.003, 0.004, 0.005, 0.0075, 0.01, 0.05, 0.1, 0.5, 1, 2, 3, 4, or 5% of the at least one bacteriocin peptide or peptide mixture. In other embodiments, the bacteriocin composition of the present invention comprises about 0.00010% to about 4.5% of at least one bacteriocin peptide, or combination of peptides, selected from the group consisting of SEQ ID NO:1, SEQ ID NO:2, SEQ ID NO:3, SEQ ID NO:4, and homologs thereof, or about 0.0003% to about 3.5% of the at least one bacteriocin peptide or peptide mixture, or 0.0005% to about 2.5% of the at least one bacteriocin peptide or peptide mixture, or 0.001% to about 2% of the at least one bacteriocin peptide or peptide mixture, or 0.005% to about 1.5% of the at least one bacteriocin peptide or peptide mixture, or 0.0075% to about 1.0% of the at least one bacteriocin peptide or peptide mixture, or 0.01% to about 0.5% of the at least one bacteriocin peptide or peptide mixture, or 0.1% to about 0.3% of the at least one bacteriocin peptide or peptide mixture. In other embodiments, the bacteriocin composition of the present invention comprises about 3% of at least one bacteriocin peptide, or combination of peptides, selected from the group consisting of SEQ ID NO:1, SEQ ID NO:2, SEQ ID NO:3, SEQ ID NO:4, and homologs thereof. In other embodiments, the bacteriocin composition of the present invention comprises about 1% of at least one bacteriocin peptide, or combination of peptides, selected from the group consisting of SEQ ID NO: 1, SEQ ID NO:2, SEQ ID NO:3, SEQ ID NO:4, and homologs thereof. In other embodiments, the bacteriocin composition of the present invention comprises about 0.1% of at least one bacteriocin peptide, or combination of peptides, selected from the group consisting of SEQ ID NO: 1, SEQ ID NO:2, SEQ ID NO:3, SEQ ID NO:4, and homologs thereof.

In order for bacteriocin composition of the invention to achieve desirable bactericidal activity in vivo, that is, to act either directly on the non-mucosal surfaces of the vulva or the mucosal surfaces of the vaginal cavity, the bacteriocin peptide unit dose, or mixture of peptides unit dose, is incorporated with at least one pharmaceutically acceptable excipient. As used herein, the term "unit dose" or "unit dosage" or "unit" refers to a physically discrete unit that contains a predetermined quantity of active ingredient (i.e., the MIC or amount of bacteriocin peptide, or mixture of peptides) calculated to produce a desired therapeutic effect. The unit dose or unit dosage or unit may be in the form of gels, creams, ointments, capsules, suppositories, etc. referred to herein as a "unit dosage form." Any excipient used in formulations having a bacteriocin peptide unit dose of this invention, or peptide mixture unit dose, needs to be approved for human use and acceptable for use in the vagina. Excipients approved for oral use may not be approved and/or be suitable for intravaginal applications. Suitable nontoxic pharmaceutically acceptable excipients for use in the bacteriocin compositions of the present invention will be apparent to those skilled in the art of pharmaceutical formulations and examples are described in *REMINGTON'S Pharmaceutical Sciences,* 19th Edition, A. R. Gennaro, ed., (1995).

The choice of suitable pharmaceutically acceptable excipients will depend on the exact nature of the topical intravaginal formulation and dosage form desired, e.g., whether the bacteriocin composition is to be formulated into such as, for example, gels, creams, ointments, capsules, or suppositories. In some embodiments, the bacteriocin composition of the instant invention is a sterile or almost sterile semi-solid preparation formulation suitable for topical intravaginal applications to the vaginal tract, such as, a cream, ointment, gel or emulsion. Various classes of suitable pharmaceutically acceptable excipients can be used in the intravaginal formulations and are known to those in the art. See, for example, Garg et al. (2001), Compendium of Pharmaceutical Excipients for Vaginal Formulations, *Pharm. Tech.* 25:14-24. For example, suitable pharmaceutically acceptable excipients include, but are not limited to, hydrocarbon bases or oleaginous bases, absorption bases, water-removable bases and water-soluble bases (*Remington: The Science and Practice of Pharmacy,* $20^{th}$ ed. (2000)). In some embodiments, the pharmaceutically acceptable excipient is non-irritating, non-staining, stable, non-pH dependent, and compatible with the bacteriocin/peptide mixture. In some embodiments, the pharmaceutically acceptable excipient can be, but is not limited to, a stiffening agent, an oil, a solvent, an emulsifier, a humectant, a buffering agent, a filler, an emollient, a stabilizer, or combinations thereof.

The term "stiffening agent" refers to a substance, or mixture of substances, added to make a vaginal cream composition more viscous at room temperature. In some embodiments, a stiffening agent is any substance that promotes formation of a formulation having a semi-solid consistency. The stiffening agent can be hydrophilic (e.g., Carbopol®, carboxymethylcellulose, hydroxypropylmethylcellulose, alginate, polyethylene glycol). In some embodiments, the stiffening agent has low hydrophilic-lipophilic balance (HLB). In some embodiments, the HLB value is less than 7. In some embodiments, the HLB value is less than 5. In some embodiments, the HLB value is about 4. Examples of suitable stiffening agents include, but are not limited to, hydrogenated vegetable oil, cetyl alcohol, cetyl esters wax, microcrystalline wax, paraffin, stearyl alcohol, lauryl alcohol, myristal alcohol, cetostearyl alcohol, white wax, yellow wax, beeswax, candelilla wax, cotton wax, carnauba wax, bayberry wax, rice-bran wax, and combinations thereof. In some embodiments, the stiffening agent is a mixture of cetyl esters wax, cetyl alcohol, and beeswax.

The term "oil" refers to any pharmaceutically acceptable hydrophobic liquid. In some embodiments, an oil is an ester of glycerol (1,2,3-propanetriol) and fatty acids. Generally, the fatty acid hydrocarbon chains each contain greater than 8 carbons. In some embodiments, each hydrocarbon chain contains from about 12 to about 36 carbon atoms. In some embodiments, the hydrocarbon chains can contain a variety of functional groups. In some embodiments, the hydrocarbon chain is branched. In some embodiments, the hydrocarbon chains are unsaturated or polyunsaturated. In some embodiments, the hydrocarbon chains are saturated. The degree of saturation can affect the physical state, for example viscosity, of the oil. In some embodiments, the oil can be, but is not limited to, vegetable, nut, and seed oils (e.g., almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower-seed oil, *crambe* oil, wheat germ oil, and cocoa butter), hydrocarbon and petroleum oils (e.g., petrolatum, mineral oil, and liquid paraffin). In some embodiments, the term "oil" refers to higher fatty acids (e.g., lauric acid, myristic acid, palmitic acid, stearic acid, behenic acid, oleic acid, 12-hydroxystearic acid, undecylenic acid, tall acid, lanolin fatty acid, isostearic acid, linoleic acid, and linolenic acid) and combinations thereof. In some embodiments, the oil is not an ester of glycerol, e.g., mineral oil and silicone oil.

The term "solvent" refers to a type of pharmaceutically acceptable excipient that is capable of dissolving or dispersing one or more of the bacteriocin peptides and/or additional excipients of the bacteriocin composition. The solvent can be aqueous or non-aqueous. In some embodiments, the solvent is hydrophilic, and is 10% to 75% by weight, or 20% to 60% by weight, of the total composition. In some embodiments, the solvent is lipophilic, and is 20% to 60% by weight, or 25% to 50% by weight, of the total composition. In some embodiments, the solvent is water, a polyol (e.g., glycerol) or combinations thereof. In some embodiments, the solvent is an oil as described above.

The term "emulsifier" refers to a type of pharmaceutically acceptable excipient that promotes formation and stabilization of an emulsion or suspension. In some embodiments, the emulsifier includes, but is not limited to, sodium lauryl sulfate, propylene glycol monostearate, methyl stearate, glyceryl monostearate, and combinations thereof.

The term "humectant" refers to a type of pharmaceutically acceptable excipient that promotes retention of moisture in the bacteriocin composition of the present invention. In some embodiments, the humectant includes, but is not limited to, polyethylene glycol, propylene glycol, glycerin, polyol, polyol derivatives, and combinations thereof.

The term "buffering agent" refers to a type of pharmaceutically acceptable excipient capable of neutralizing both acids and bases and thereby maintaining the desired pH of the bacteriocin composition of the present invention. In some embodiments, the buffering agent affects the emulsifying properties. For example, different buffering agents can be provided to increase or decrease the emulsification of the one or more of the bacteriocin peptides and/or additional excipients of the bacteriocin composition. In some embodiments, the buffer can be, but is not limited to, Tris buffers (Tris EDTA (TE), Tris acetate (TAE), Tris phosphate (TPE), Tris glycine), phosphate buffers (e.g., sodium phosphate, potassium phosphate), bicarbonate buffers, acetate buffers (e.g., sodium acetate), ammonium buffers, citrate buffers, and derivatives and combinations thereof. In some embodiments, an organic acid buffer is used. In some embodiments, an acetate buffer, a phosphate buffer, or a citrate buffer can be used. In some embodiments, a zwitterionic buffer can be used. In some embodiments, the buffering agent is a phosphate buffer (e.g., sodium phosphate dibasic).

The pH of the bacteriocin composition of the invention can be physiologically compatible and/or sufficient to maintain stability of the composition. In some embodiments, the composition of the present invention can have a pH of about 4.0 to about 9.0. In some embodiments, the composition of the present invention can have a pH of about 4.0, 4.5, 5.0, 5.5, 6.0, 6.5, 7.0, 7.5, 8.0, 8.5, or 9.0. In some embodiments, the composition of the present invention can have a pH of about 5.0 to about 9.0, about 5.5 to about 8.5, about 6.0 to about 8.0, or about 6.5 to about 7.5. In some embodiments, the composition of the present invention can have a pH of about 5.0 to about 6.0.

As defined herein, an "emollient" is a type of pharmaceutically acceptable excipient that moisturizes and increases the pliability of the vaginal surface to which the intravaginal formulation of the bacteriocin composition is applied. In some embodiments, the emollient can be, but is not limited to, lanolin, isopropyl myristate, palmitate, oleyl alcohol, beeswax, mineral oil, silicone oil, or combinations thereof.

As defined herein, a "filler" is a type of pharmaceutically acceptable excipient used to give bulk to the intravaginal formulation without chemically reacting with the bacteriocin peptides and/or additional excipients of the bacteriocin composition of the present invention. Fillers are known to those in the art, see e.g., *Remington: The Science and Practice of Pharmacy*, 20th ed. (2000).

Co-Compounded Bacteriocin Compositions

The bacteriocin compositions of the invention can also contain an antibiotic to form a co-compounded bacteriocin composition, in which the peptide, or combination of peptides, selectively inhibit *L. iners* and the antibiotic of the bacteriocin composition inhibits diverse non-*Lactobacillus* spp. (i.e., BV-associated organisms). In some embodiments, the bacteriocin composition of the invention can include any suitable antibiotic such as, for example, clindamycin, metronidazole, secnidazole, tinidazol, or VivaGel® (SPL-7013, or astodrimer sodium), in addition to the peptide, or combination of peptides, and pharmaceutically acceptable excipient. In some embodiments, the bacteriocin composition of the invention can include an antibiotic selected from clindamycin, metronidazole, secnidazole, and astodrimer sodium, in addition to the bacteriocin peptide, or combination of peptides, and pharmaceutically acceptable excipient. In some embodiments, the bacteriocin composition of the invention can include clindamycin or astodrimer sodium as the antibitric, in addition to the bacteriocin peptide, or combination of peptides, and pharmaceutically acceptable excipient. In other embodiments, the bacteriocin composition of the invention can include clindamycin as the antibiotic, in addition to the bacteriocin peptide, or combination of peptides, and pharmaceutically acceptable excipient.

In some embodiments, the bacteriocin composition of the present invention optionally comprises from about 0.01% to about 5% of a suitable antibiotic. In some embodiments, the bacteriocin composition of the present invention optionally comprises about 0.01% of a suitable antibiotic, or about 0.025, 0.05, 0.075, 0.1, 0.25, 0.5, 0.75, 1, 1.5, 2, 2.5, 3, 3.5, 4, 4.5, or 5% antibiotic. In other embodiments, the bacteriocin composition of the present invention optionally comprises about 0.05% to about 4% of a suitable antibiotic, or about 0.1% to about 3% of a suitable antibiotic, or 0.5% to about 3% of a suitable antibiotic, or 1% to about 2% of a suitable antibiotic. In other embodiments, the bacteriocin composition of the present invention optionally comprises about 2% of a suitable antibiotic.

IV. Methods of Treatment

Diagnosing Patients with Diverse Microbiota Associated with BV

Diverse microbiota associated with BV can be detected and diagnosed using any suitable means known in the art. Diverse microbiota associated with BV can be symptomatic or asymptomatic. Symptoms can include abnormal vaginal odor, increase in vaginal discharge, and vaginal discomfort from itching and/or pain. In some cases, symptomatic diverse microbiota associated with BV can depend on the dominating bacterial communities of the patient's vaginal microbiota. For example, abnormal vaginal odor attributed to BV can be associated with a diverse microbiota dominated by the following non-*Lactobacillus* spp.: *Gardnerella vaginalis, Leptotrichia amnionii, Eggerthella, Dialister micaerophilus, Parvimonas micra, Prevotella buccalis, Prevotella bivia, Prevotella disiens, Porphyromonas asaccharolytica*, and BVAB1. In other cases, an increase in vaginal discharge and/or discolored vaginal discharge attributed to BV may be associated with a diverse microbiota dominated by the following non-*Lactobacillus* spp.: *Atopobium vaginae, Leptotrichia amnionii, Eggerthella, Parvimonas micra, and Prevotella timonensis*. (See, Srinivasan et al., 2012. Bacterial Communities in Women with Bacterial Vaginosis: High Resolution Phylogenetic Analyses Reveal Relationships of Microbiota to Clinical Criteria PLoS *One* 7(6), Article No.: e37818).

Medical practitioners can detect and diagnose the diverse microbiota associated with BV, whether it is symptomatic or asymptomatic. A diverse microbiota associated with BV is detected clinically in the female patient using the Amsel criteria (Amsel, R. et al. 1983. Nonspecific vaginitis. Diagnostic criteria and microbial and epidemiologic associations. *Am. J. Med.* 74:14-22), or microbiologically using the Nugent scoring system (Nugent, R. et al. 1991. Reliability of diagnosing bacterial vaginosis is improved by a standardized method of gram stain interpretation. *J. Clin. Microbiol.* 29(2):297-301). The Amsel clinical diagnosis of BV must satisfy at least 3 of the 4 Amsel criteria: thin grey homogeneous vaginal discharge, odor (positive whiff test upon addition of KOH to genital fluid), >20% clue cells (vaginal epithelial cells studded with adherent coccobacilli observed microscopically), and pH >4.5.

The diverse microbiota associated with BV can be detected microbiologically by examining Gram-stained vaginal smears (Nugent scoring system) to determine the relative concentration of lactobacilli (Gram-positive bacteria), and Gram-negative and Gram-variable rods and cocci (i.e., *Gardnerella vaginalis, Atopobium vaginae, Prevotella, Porphyromonas,* and Peptostreptococci), and curved Gram-negative rods (i.e., Mobiluncus) characteristic of diverse microbiota associated with BV. The Nugent score can range from 0 to 10. A score of 0 to 3 is considered to be the normal range and is indicative of vaginal mucosa having a preponderance of *Lactobacillus* spp. and relatively low numbers of the bacteria that are typically associated with BV. A score of 4-6 is considered to be an "intermediate Nugent score," and is associated with a more diverse microbiota and vaginal mucosa, often containing significant numbers of *L. iners*. BV is defined as a Nugent score of 7 to 10 with a diverse microbiota and few, if any, protective *Lactobacillus. Lactobacillus iners* is generally the only *Lactobacillus* found in BV. As such, a Nugent score of at least 4 (i.e., a Nugent score of greater than or equal to 4, or a Nugent score of 4 to 10) is associated with a diverse microbiota that is not dominated by protective *Lactobacillus* spp. Detection and diagnostic methods for symptomatic diverse microbiota associated with BV are well known in the art and are described in U.S. Pat. No. 8,329,447. See also, Srinivasan et al., 2012. Bacterial Communities in Women with Bacterial Vaginosis: High Resolution Phylogenetic Analyses Reveal Relationships of Microbiota to Clinical Criteria *PLoS One* 7(6), Article No.: e37818; Haahr, T. et al. *Hum. Reprod.* 2016 April, 31(4):795-803; Datcu, R. et al. *BMC Infectious Diseases* 2013, 13:480; https://www.cdc.gov/std/tg2015/bv.htm.

In some cases, Quantitative Polymerase Chain Reaction (qPCR) methods can be used to diagnose a woman with diverse microbiota associated with BV by measuring several indicator organisms with high BV prevalence and predictive of BV (i.e., *Gardnerella vaginalis, Atopobium vaginae*). For example, a woman can be tested for diverse microbiota associated with BV by a medical practitioner using qPCR to identify and quantify specific bacteria of the vaginal microbiome. The medical practitioner can extract the bacterial DNA from vaginal swabs obtained during speculum examination. Bacterial DNA is extracted using a spin column, such as, for example, the FastDNA™ SPIN kit for Soil (MP Biomedicals, Santa Ana, Calif., USA) with about 200 µL of ESwab™ transport medium, followed by elution of the DNA in approximately 100 µL DNase free water. qPCR is then performed in about 50 µL total reaction volume with about 5 µL of template DNA or about 50 ng of genomic DNA (gDNA). An abnormal vaginal microbiota is defined when *G. vaginalis* and/or *A. vaginae* are present at concentrations above threshold concentrations defined by ROC curve analysis using the Nugent BV score of 7-10 as the gold standard. The threshold levels for *G. vaginalis* and *A. vaginae* were established as $5.7 \times 10^7$ and $5.7 \times 10^6$ 16S rRNA gene copies/mL, respectively. The samples collected from a woman with a bacterial load that are above the cut-off points (i.e., as defined by the ROC) are considered positive for BV-associated organisms and the samples with a bacterial load below the cut-off points are considered negative for BV-associated organisms. See, Haahr, T. et al. *Hum. Reprod.* 2016 April, 31(4):795-803 and Datcu, R. et al. *BMC Infectious Diseases* 2013, 13:480.

The vaginal mucosa of a woman diagnosed with having a diverse microbiota associated with BV, by definition, lacks a sufficient amount of protective *Lactobacillus* spp. (i.e., $H_2O_2$-producing vaginal *Lactobacillus*). Because the less protective *L. iners* is the only vaginal *Lactobacillus* spp. that can co-exist with BV-associated organisms, a vaginal mucosal microbiota (i.e., vaginal niche) populated with BV-associated organisms may also contain *L. iners*. Thus, for the purposes of the instant invention, it can be understood that a vaginal mucosa populated with low levels of $H_2O_2$-producing vaginal *Lactobacillus* may be colonized by significant numbers of *L. iners*, or significant numbers of BV-associated organisms, or, in some cases, significant numbers of BV-associated organisms and observable numbers of *L. iners*.

The levels of vaginal *Lactobacillus* that commonly produce $H_2O_2$ in a patient (e.g., *L. crispatus, L. jensenii,* and *L. gasseri*) can be determined by qPCR. The medical practitioner can obtain swabs from the posterior fornix during speculum examination to identify and quantify specific *Lactobacillus* spp. of the vaginal microbiome that are associated with $H_2O_2$ production. As such, the above-described qPCR methods can be used to measure *L. crispatus, L. jensenii,* and *L. gasseri* to estimate the levels of $H_2O_2$-producing vaginal *Lactobacillus* in a patient.

Alternatively, the level of $H_2O_2$-producing vaginal *Lactobacillus* in a patient can be determined using the culture method or the direct detection method. The culture method involves measuring $H_2O_2$ production by semi-quantifying the intensity of a blue pigment formed when *Lactobacillus* is inoculated onto tetramethylbenzidine medium (TMB) and incubated under anaerobic conditions. For example, a patient's swabbed sample is processed and incubated on a TMB agar plate for about 48 hours under anaerobic conditions at 37° C. The agar plate is then exposed to ambient air. Exposure to the ambient air causes the $H_2O_2$ produced by the *Lactobacillus* to react with horseradish peroxidase in the agar to oxidize the TMB, causing any *Lactobacillus* colonies to turn blue over time. See, Antonio et al. *The Journal of Infectious Diseases* 1999; 180:1950-1956.

Readings of the agar plate are performed 30 min after exposure to ambient air. See, Rabe and Hillier, Optimization of media for detection of $H_2O_2$ production by *Lactobacillus* species. *J. Clin. Microbiol.* 2003, 41(7): 3260-3264. The level of $H_2O_2$ produced is determined by identifying the intensity of blue coloration according to the following semi-quantitative scale: (−)=lack of colony coloration; (+/−)=minimal blue coloration of the colonies; (+)=small and limited blue coloration of the colonies; (++)=large but incomplete blue coloration of the colonies; and (++++)=clearly visible and complete blue coloration of the colonies. See, Strus, M. et al. The in vitro activity of vaginal *Lactobacillus* with probiotic properties against *Candida. Infect Dis Obstet Gynecol.* 2005 June; 13(2):69-75. A plate reading of (−), (+/−), or (+) after 24 hours of air exposure is associated with vaginal mucosa colonized by low levels of $H_2O_2$-producing vaginal *Lactobacillus*. A plate reading of (++) or (+++) after 24 hours of air exposure is associated with vaginal mucosa colonized by a sufficient amount of protective *Lactobacillus* spp.

The direct detection method can be used to detect $H_2O_2$-producing vaginal *Lactobacillus* in the patient using commercially available peroxide test strips for $H_2O_2$ production (e.g., available from EM Sciences or Merck). A patient's swabbed sample is processed, plated on MRS agar, and cultured for up to 48 hours under anaerobic conditions at 37° C. The culture plate is then exposed to air and the test strip is placed directly on top of a bacterial colony. The test strip is observed for a color change. If the test strip turns blue, $H_2O_2$-producing vaginal *Lactobacillus* is present; if the test strip does not change color, $H_2O_2$-producing vaginal *Lactobacillus* is not present.

A woman diagnosed with having low levels of $H_2O_2$-producing vaginal *Lactobacillus* and a diverse microbiota associated with BV (i.e., the vaginal mucosa is colonized by *L. iners* and diverse non-*Lactobacillus* spp. and underpopulated by protective $H_2O_2$-producing *Lactobacillus*) using any of the above described diagnostic methods will be administered bacteriocin compositions, and/or antibiotics, and/or live bacterial compositions as described below.

Administration of Bacteriocin Compositions

A woman diagnosed with having low levels of $H_2O_2$-producing vaginal *Lactobacillus* and a Nugent score of at least 4 (i.e., a Nugent score of greater than or equal to 4) can be intravaginally administered a bacteriocin composition of the instant invention in an amount sufficient to decrease levels of *L. iners* and to promote growth of endogenous $H_2O_2$-producing vaginal *Lactobacillus*. In some embodiments, decreasing the levels of *L. iners* of the vaginal mucosa allows for the growth of endogenous $H_2O_2$-producing vaginal *Lactobacillus*. The bacteriocin composition can be administered in any suitable amount and for any suitable duration to decrease levels of *L. iners* and to promote growth of endogenous $H_2O_2$-producing vaginal *Lactobacillus*.

As described previously, women with low levels of $H_2O_2$-producing vaginal *Lactobacillus* and significant numbers of *L. iners* and/or significant numbers of BV-associated organisms (i.e., Nugent score of at least 4) have BV, or have a higher susceptibility to BV compared to women with relatively high population levels of *Lactobacillus* spp. that produce $H_2O_2$. In addition to being more susceptible to BV, women having low levels of $H_2O_2$-producing vaginal *Lactobacillus* and significant numbers of *L. iners* and/or significant numbers of BV-associated organisms (i.e., Nugent score of at least 4) have a higher susceptibility to BV-associated gynecologic and obstetric complications, such as PID, pathogen transmission, higher miscarriage rates, preterm birth (PTB), and lower success rates when undergoing in vitro fertilization treatment. Accordingly, treating a patient having low levels of $H_2O_2$-producing vaginal *Lactobacillus* and a Nugent score of at least 4 with the bacteriocin compositions described herein leads to decreased levels of *L. iners* and promotes the growth of endogenous $H_2O_2$-producing vaginal *Lactobacillus*, thereby treating or preventing BV and associated gynecologic and obstetric complications.

Therefore, the bacteriocin compositions of the present invention are useful for the prevention or treatment of BV and associated gynecologic and obstetric complications, such as PID, pathogen transmission, miscarriage, PTB, and IVF failures. As such, provided herein are methods for treating or preventing a gynecologic or obstetric disorder in a patient having low levels of $H_2O_2$-producing vaginal *Lactobacillus* and a Nugent score of at least 4 (i.e., a Nugent score of greater than or equal to 4), the method comprising intravaginally administering to the patient a bacteriocin composition of least one pharmaceutically acceptable excipient; and at least one isolated peptide, or a combination of isolated peptides, wherein: the at least one isolated peptide, or combination of isolated peptides, has selective bactericidal activity against *L. iners*; and the at least one isolated peptide is selected from the group consisting of SEQ ID NO:1, SEQ ID NO:2, SEQ ID NO:3, SEQ ID NO:4, and an isolated peptide having 90% sequence identity to one of SEQ ID NOs:1, 2, 3, or 4, and wherein the at least one isolated peptide, or combination of isolated peptides, is administered in an amount sufficient to decrease levels of *L. iners* and to promote growth of endogenous $H_2O_2$-producing vaginal *Lactobacillus*, thereby treating or preventing the gynecologic or obstetric disorder. In some embodiments, the disorder is BV. In some embodiments, the disorder is PTB. In some embodiments, the disorder is IVF failure.

In some embodiments, the bacteriocin compositions of the present invention are used to treat or prevent BV in a patient having low levels of $H_2O_2$-producing vaginal *Lactobacillus* and a Nugent score of at least 4 wherein the composition is administered in an amount sufficient to decrease levels of *L. iners* and promote growth of endogenous $H_2O_2$-producing vaginal *Lactobacillus*, thereby treating or preventing BV in the patient. In some embodiments, the bacteriocin compositions of the present invention are used to prevent PTB in a patient having low levels of $H_2O_2$-producing vaginal *Lactobacillus* and a Nugent score of at least 4 wherein the composition is administered in an amount sufficient to decrease levels of *L. iners* and promote growth of endogenous $H_2O_2$-producing vaginal *Lactobacillus*, thereby preventing PTB in the patient. In some embodiments, the bacteriocin compositions of the present invention are used to prevent IVF failure in a patient having low levels of $H_2O_2$-producing vaginal *Lactobacillus* and a Nugent score of at least 4 wherein the composition is administered in an amount sufficient to decrease levels of *L. iners* and promote growth of endogenous $H_2O_2$-producing vaginal *Lactobacillus*, thereby preventing IVF failure in the patient.

As described in detail above, bacteriocin compositions suitable for intravaginal administration comprise at least one isolated bacteriocin peptide, or combination of peptides, selected from the group consisting of SEQ ID NO:1, SEQ ID NO:2, SEQ ID NO:3, SEQ ID NO:4, and homologs thereof, in an amount sufficient for the composition as a whole to exhibit bactericidal properties in vivo. Such bacteriocin compositions can be administered intravaginally to decrease levels of *L. iners* and to promote growth of endogenous $H_2O_2$-producing vaginal *Lactobacillus*. In some embodiments, the bacteriocin compositions are administered intravaginally in a unit dose to decrease levels of *L. iners* and to promote growth of endogenous $H_2O_2$-producing vaginal *Lactobacillus*.

The bacteriocin composition can be in any suitable formulation for intravaginal administration, and more specifically, topical intravaginal administration. For example, the bacteriocin composition having at least one pharmaceutically acceptable excipient and at least one-unit dose of the peptide or combination of peptides, as described herein, can be delivered as a gel, cream, or as a vaginal ovule suppository. In some embodiments, the bacteriocin composition can be administered 1 or 2 times per day. In some embodiments of the invention, the bacteriocin composition can be administered for between 2 and 7 days. In other embodiments, the bacteriocin composition can be administered for 2, 3, 4, 5, 6, and 7 days. In some other embodiments, the bacteriocin composition can be administered for between 2 and 7 days, or 3 and 6 days, or 4 and 5 days, or 4 and 7 days. In particular embodiments, the bacteriocin composition can be administered for between 2 and 7 days. In another embodiment, the bacteriocin composition can be administered for 7 days. In another embodiment, the bacteriocin composition can be administered for 5 days.

Administration of Antibiotics

A woman diagnosed with having low levels of $H_2O_2$-producing vaginal *Lactobacillus* and a Nugent score of at least 4 (i.e., a Nugent score of greater than or equal to 4) can be administered at least one antibiotic active against BV-associated organisms in an amount sufficient to decrease levels of BV-associated organisms (i.e., diverse non-*Lactobacillus* spp.) in addition to intravaginally administering the bacteriocin composition as described above. In some embodiments, decreasing the levels of *L. iners* and the levels of diverse non-*Lactobacillus* spp. of the vaginal mucosa allows for the growth of endogenous $H_2O_2$-producing vaginal *Lactobacillus*. The antibiotic can be administered in any suitable amount and for any suitable duration to reduce the quantity of BV-associated organisms. Suitable antibiotics for decreasing levels of BV-associated organisms (i.e., *Gardnerella vaginalis, Atopobium vaginae, Leptotrichia amnionii*, Eggerthella, and organisms within the Clostridiales Order) are well known in the art. Such antibiotics include, but are not limited to, Clindamycin, metronidazole, secnidazole, tinidazol, and VivaGel® (SPL-7013, or astodrimer sodium). Antibiotics can be administered individually or as a combination therapy. In some embodiments, the administration of VivaGel® (SPL-7013, or astodrimer sodium), can reduce both the quantity of BV-associated organisms and the quantity of *L. iners*.

The antibiotic can be administered prior to, concurrently with, or after intravaginally administering the bacteriocin composition. In some embodiments, the antibiotic is administered prior to intravaginally administering the bacteriocin composition (i.e., the antibiotic treatment regimen is completed fully before intravaginally administering the bacteriocin composition). In such embodiments, the diverse non-*Lactobacillus* spp. (i.e., BV-associated organisms) populating the vagina will be inhibited first by the administered antibiotic, followed by the inhibition of the less protective *Lactobacillus* species, *L. iners*, due to intravaginal administration of the bacteriocin composition. In other embodiments, the antibiotic is administered after intravaginally administering the bacteriocin composition (i.e., the intravaginal bacteriocin composition treatment regimen is completed fully before administering the antibiotic). In such embodiments, the *L. iners* species populating the vaginal mucosa are inhibited by intravaginally administering the bacteriocin composition, followed by inhibiting diverse non-*Lactobacillus* spp. (i.e., BV-associated organisms) populating the vagina by administering the antibiotic.

In some embodiments, the antibiotic can be administered concurrently with the bacteriocin composition. Concurrent administration of two agents (i.e., an antibiotic and a bacteriocin composition) refers to administration wherein the time period over which the first agent is administered either overlaps with, or is coincident with, the time period over which the second agent is administered. Furthermore, for the purposes of the instant invention, two agents that are concurrently administered relates to concurrent administration of two separate formulations. For example, a first and a second agent are concurrently administered if the first agent is administered once per week for four weeks, and the second agent is administered twice per w % eek for the first three of those four weeks. Likewise, for example, a first and second agent are concurrently administered if the first and second agent are each administered on the same day once per week for four weeks. For additional clarity, co-compounded bacteriocin compositions of the invention (i.e., bacteriocin compositions containing a peptide, or combination of peptides, that selectively inhibit *L. iners* and an antibiotic that inhibits diverse non-*Lactobacillus* spp.) is not the same as concurrent administration of an antibiotic and a bacteriocin composition.

The antibiotic treatment regimen will vary depending upon the particular antibiotic that is being administered. The antibiotic for decreasing levels of BV-associated organisms in a woman can be in any suitable form for administration. For example, the antibiotic can be delivered topically (as a gel or cream), or as an oral or vaginal tablet, capsule or suppository. In some embodiments, the antibiotic is administered as an oral tablet or a topical gel. In some embodiments, the antibiotic is administered as an oral tablet. In some embodiments, the antibiotic is administered as a topical gel.

In some embodiments, the antibiotic can be administered 1 or 2 times per day. In some embodiments of the invention, the antibiotic can be administered for between 2 and 7 days. In other embodiments, the antibiotic can be administered for 2, 3, 4, 5, 6, and 7 days. In some other embodiments, the antibiotic can be administered for between 2 and 7 days, or 3 and 6 days, or 4 and 5 days, or 4 and 7 days. In particular embodiments, the antibiotic can be administered for between 2 and 7 days. In another embodiment, the antibiotic can be administered for 7 days. In another embodiment, the antibiotic can be administered for 5 days.

The antibiotic can be administered in any suitable dosage effective to decrease levels of BV-associated organisms in a woman. In some embodiments, the antibiotic treatment is administered as an oral tablet or as an intravaginal ovule suppository. The dosage of the oral tablet or ovule antibiotic can be about 0.1 mg to about 10,000 mg, or about 1 mg to about 2000 mg, or about 10 mg to about 1000 mg, or about 25 mg to about 750 mg, or about 50 mg to about 500 mg. In some embodiments, the dosage of the antibiotic oral tablet or ovule can be about 1 mg, 5, 10, 20, 30, 40, 50, 60, 70, 80, 90, 100, 200, 300, 400, 500, 600, 700, 800, 900 or 1200 mg. In some embodiments, the dosage of the oral tablet or ovule antibiotic can be between about 50 mg and 300 mg.

In some embodiments, the antibiotic dosage of the oral tablet or ovule can be about 0.1 mg/kg of body weight per patient, or 0.5, 1, 5, 10, 25, 50, 100, 250, 500, 750, or 1000 mg/kg of body weight per patient. In other embodiments, the antibiotic dosage of the oral tablet or ovule can be from about 0.1 to 1000 mg/kg of body weight per patient, or from about 0.5 to 750, or from about 1 to 500, or from about 5 to 250, or from about 10 to 100, or from about 25 to 50 mg/kg of body weight per patient. In still another embodiment, the antibiotic dosage of the oral tablet or ovule can be between about 0.5 to about 25 mg/kg of body weight per patient, or between about 5 to 15 mg/kg of body weight per patient, or between about 8 to about 12 mg/kg of body weight per patient, or about 10 mg/kg of body weight per patient.

In some embodiments, the antibiotic treatment is administered as a topical gel in a dosage from about 0.10% to about 2% of the total gel formulation, or about 0.3% to about 1.75%, or about 0.5% to about 1.25%, or about 0.75% to about 1%. Suitable dosages for the antibiotic topical gel include about 0.1%, 0.2, 0.3, 0.4, 0.5, 0.6, 0.7, 0.8, 1.0, 1.1, 1.2, 1.3, 1.4, 1.5, 1.6, 1.7, 1.8, 1.9 or 2%. In some embodiments, the dose of the antibiotic topical gel is about 0.75%. In other embodiments, the dose of the antibiotic topical gel is about 1.0%.

Administration of $H_2O_2$-Producing Lactobacilli

In some cases, patients having received treatment for a diverse microbiota associated with BV (i.e., intravaginal administration of bacteriocin compositions with or without the administration of antibiotics) may still have low levels of $H_2O_2$-producing vaginal *Lactobacillus*. In such cases, the patient lacks a sufficient amount of viable endogenous $H_2O_2$-producing vaginal *Lactobacillus* to recolonize the vaginal mucosa, even though the populations of *L. iners* of the vaginal mucosa have been decreased via administration of the bacteriocin composition, or both the populations of *L. iners* and diverse non-*Lactobacillus* spp. of the vaginal mucosa have been decreased via administration of the bacteriocin composition and administration of an antibiotic. Therefore, a live bacterial composition can be administered as an additional treatment regimen to increase the levels of $H_2O_2$-producing vaginal *Lactobacillus* in a woman.

In some embodiments, a woman diagnosed with having low levels of $H_2O_2$-producing vaginal *Lactobacillus* and a Nugent score of at least 4 (i.e., a Nugent score of greater than or equal to 4) can be administered a live bacterial composition comprising $H_2O_2$-producing vaginal *Lactobacillus* in an amount sufficient to promote growth of administered $H_2O_2$-producing vaginal *Lactobacillus* in addition to intravaginally administering the bacteriocin composition as described above. In some embodiments, a live bacterial composition comprising $H_2O_2$-producing vaginal *Lactobacillus* can be administered in addition to administering an antibiotic and intravaginally administering the bacteriocin composition as described above.

The live bacterial composition can be administered in any suitable amount and for any suitable duration to promote growth of administered $H_2O_2$-producing vaginal *Lactobacillus*. Live bacterial compositions suitable for administration contain at least one strain of live $H_2O_2$-producing vaginal *Lactobacillus* such as, for example, *L. crispatus, L. gasseri, L. jensenii*, or a species of *Lactobacillus* having 95% sequence homology to the 16S rRNA gene sequence of any of the identified species. Particularly preferred strains of lactobacilli are strains having all the identifying characteristics of the *Lactobacillus* crispatus CTV-05 strain or the *Lactobacillus* crispatus SJ-3C strain. Methods of obtaining and preparing live bacterial compositions comprising live $H_2O_2$-producing vaginal *Lactobacillus* strains are described in detail in U.S. Patent Application Nos. 62/529,733 and 62/529,756 and are incorporated herein by reference.

The live bacterial composition can be administered prior to, concurrently with, or after intravaginally administering the bacteriocin composition described above. In some embodiments, the live bacterial composition is administered after intravaginally administering the bacteriocin composition (i.e., the intravaginal bacteriocin composition treatment regimen is completed fully before administering the live bacterial composition). In such embodiments, the *L. iners* species populating the vaginal mucosa are inhibited by intravaginally administering the bacteriocin composition, followed by promoting growth of administered $H_2O_2$-producing vaginal *Lactobacillus* by administering the live bacterial composition. In some embodiments, the live bacterial composition is administered concurrently with intravaginally administering the bacteriocin composition.

In some embodiments, the live bacterial composition can be administered prior to, concurrently with, or after administering an antibiotic and intravaginally administering the bacteriocin composition, as described in detail above. In some embodiments, the live bacterial composition is administered after intravaginally administering the bacteriocin composition and after administering the antibiotic (i.e., the intravaginal bacteriocin composition treatment regimen and the antibiotic treatment regimen is completed fully before administering the live bacterial composition). In such embodiments, the *L. iners* species and diverse non-*Lactobacillus* spp. populating the vaginal mucosa are inhibited by intravaginally administering the bacteriocin composition and antibiotic, respectively, followed by promoting growth of administered $H_2O_2$-producing vaginal *Lactobacillus* by administering the live bacterial composition. In some embodiments, the live bacterial composition is administered concurrently with intravaginally administering the bacteriocin composition. In some embodiments, the live bacterial composition is administered concurrently with the antibiotic, and after intravaginally administering the bacteriocin composition.

The live bacterial composition can be administered 1 or 2 times per day. In some embodiments, the administration of the live bacterial composition is during the final few days of the intravaginal administration regimen of the bacteriocin composition (i.e., 2 to 4 days before the completion of the intravaginal administration regimen of the bacteriocin composition). In some embodiments, the administration of the live bacterial composition is during the final few days of the administration regimen of an antibiotic (i.e., 2 to 4 days before the completion of the administration regimen of an antibiotic). In some embodiments, the live bacterial composition is administered after the bacteriocin composition has been intravaginally administered for 2, 3, 4, 5, 6, or 7 days. In some embodiments, the live bacterial composition is administered after an antibiotic has been administered for 2, 3, 4, 5, 6, or 7 days. In some embodiments, the live bacterial composition is administered after the bacteriocin composition has been intravaginally administered for about 7 days. In some embodiments, the live bacterial composition is administered after an antibiotic has been administered for about 7 days. In some embodiments, the live bacterial composition is administered after the bacteriocin composition has been intravaginally administered for at least 5 days. In some embodiments, the live bacterial composition is administered after an antibiotic has been administered for at least 5 days.

The live bacterial composition is administered at between 108 CFU and $10^{11}$ CFU per dose, or between 108 CFU and $10^{11}$ CFU per dose. In other embodiments, the live bacterial composition is administered at a dose of at least $10^9$ CFU per day. The live bacterial composition is administered in dosages of between about 100 mg and 600 mg, or of about 150, 200, 250, 300, 350, 400, 450, 500, or 550 mg. In other embodiments, the live bacterial composition can be administered in dosages of between about 150 mg and 450 mg, or about 150 mg and about 400 mg, or about 150 mg and about 350 mg. In some embodiments, the live bacterial composition can be administered in dosages of between about 150 mg and 250 mg. In a particular embodiment, the live bacterial composition can be administered in a dosage of about 200 mg. In some embodiments, the live bacterial composition can be administered as a dry powder composition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of V. Examples The following examples are provided by way of illustration only and not by way of limitation. Those of skill will readily recognize a variety of noncritical parameters that could be changed or modified to yield essentially similar results.

Example 1. Identification and Characterization of Bacteriocins

This example details the general strategy for obtaining and characterizing the bacteriocins useful in the bacteriocin compositions of the invention, involving bacterial cultivation, bacteriocin extraction and purification, bacteriocin activity assays, and bacteriocin identity and characterization. The procedure described here, for the culture of *L. paragasseri* K7 and the purification of its bacteriocins (GasK7A and GasK7B), is applicable for any microorganism suitable for use with the present invention.

(i) Bacterial Strains, Growth Media, and Growth Conditions.

*Lactobacillus* paragasseri strain K7 was obtained from the University of Ljubljana upon request. Additional *Lactobacillus* strains, which were screened for antimicrobial activity, were isolated from healthy female volunteers and deposited in an internal strain collection. Species tested for activity included *L. crispatus, L. jensenii* and *L. (para)gasseri*. The indicator strain, *L. sakei* subsp. *sakei* ATCC 15521, and bacteria commonly associated with vaginal dysbiosis (or BV) were obtained from public strain collections (e.g., ATCC, CCUG and BEI/NIH) and from an internal strain collection. All *Lactobacillus* strains, except *L. iners*, and *Enterococcus faecalis* were grown in Man Rogosa Sharp (MRS) media (broth or agar, Difco) at 37° C. under 5% $CO_2$. *L. iners* was grown on Columbia agar plates (Hardy diagnostics) or in NYC III broth (ATCC 1685) at 37° C. under anaerobic atmosphere (Gas pack). *Gardnerella vaginalis, Atopobium vaginae, Finegoldia,* and *Prevotella* were grown anaerobically at 37° C. on Chocolate agar plates (Hardy diagnostics) or in NYC III broth. *Streptococcus agalactiae* (group B) ATCC 13813, *Listeria monocytogenes,* and *Staphylococcus* were grown under microaerophilic conditions in brain heart infusion (BHI) media (broth and agar) at 37° C. *Lactobacillus sakei* subsp. *sakei* ATCC 15521 was grown in MRS at 30° C. All strains were maintained as frozen stocks at −80° C. in their respective culture medium with 15-20% (v/v) glycerol.

(ii) Bacteriocin Assays.

Bacteriocin activity in cell-free culture supernatants (CFCSs) from overnight cultures (16 h at 37° C.) of the different *Lactobacillus* strains were assayed using a critical dilution assay, as described previously (Holo et al 1991; Matijasid et al., 1998) using *L. sakei* subsp. *sakei* ATCC 15521 and/or *L. iners* HM-702 as the indicator strains. In general, each well in a 96-well plate contained 200 µL growth medium, bacteriocin at two-fold dilutions and the indicator organism ($10^3$ fold dilution of an overnight culture). The 96-well plate cultures were incubated overnight (16-24 hours) at appropriate temperatures and atmosphere, followed by measuring the inhibition of the indicator strain spectrophotometrically at 600 nm using a Cytation plate reader (BioTek). The bacteriocin activity for the *L. paragasseri* K7 cell-free culture supernatants (CFCSs), using *L. iners* HM-702 as the indicator strain, ranged from about 512 to 1024 BU/mL. One bacteriocin unit (BU) was defined as the amount of bacteriocin that inhibited the growth of the indicator strain by 50%, compared to the optical density of the control (growth medium only). Minimal inhibitory concentrations (MICs) for purified bacteriocins were determined using the same critical dilution assay.

(iii) Screening of *Lactobacillus* Strains for Antimicrobial Activity.

The *Lactobacillus* strains of human origin (vaginal and fecal) belonging to the species *L. crispatus, L. jensenii* and *L. (para)gasseri* were screened for antibacterial activity that antagonize bacterial species commonly associated with a dysbiotic vaginal microbiome. The indicator strains initially tested belong to the species *Gardnerella vaginalis* (CCUG 44006, clade 1), *Atopobium vaginae* (CCUG 44116) and *Lactobacillus iners* HM-702. *Lactobacillus sakei* subsp. *sakei* ATCC 15521 was included in the screen due to its sensitivity to bacteriocins from different classes. Three of the *L. crispatus* strains showed activity against *L. sakei* subsp. *sakei* in the critical dilution assay. None of the *L. jensenii* strains showed activity against *L. sakei* subsp. *sakei* in the critical dilution assay. Of the three *L. crispatus* strains showing activity against *L. sakei* subsp. *sakei,* none of these showed inhibitions of the BV-associated strains.

After the CFCSs of 78 *Lactobacillus* strains were screened against *L. iners,* including 29 *L. crispatus,* 27 *L. (para)gasseri,* and 22 *L. jensenii* strains, only three isolates (4%) were discovered with detectable activity against *L. iners* HM-702. These included two vaginal strains, *L. gasseri* 105-1 and *L. paragasseri* JV-V03, and *L. paragasseri* K7 of intestinal (fecal) origin. The activity of *L. paragasseri* K7 (5120 bacteriocin units/ml, BU/ml) against *L. iners* was significantly higher than that produced by *L. gasseri* 105-1 (160 BU/ml) or *L. paragasseri* JV-V03 (40 BU/ml) even though the supernatants were derived from cultures of comparable cell density and pH. Inhibitory spectra were determined for *L. paragasseri* K7 supernatant against a larger panel of important vaginal pathogens (Table 4). The K7 supernatant inhibited 100% of the *L. iners* strains tested (N=11) and showed weak inhibition of 17% of the *Gardnerella vaginalis* strains (N=12). In addition, the K7 culture supernatant inhibited *Streptococcus agalactiae* ATCC 13813, 100% of *Enterococcus faecalis* (N=11), 2 out of 3 *Staphylococcus aureus* and *Finegoldia* spp. No inhibition was observed for *Listeria monocytogenes* (N=6) or *Staphylococcus saprophyticus* ATCC 15305.

Concentrated *L. paragasseri* K7 supernatant (Amberlite XAD-16 fraction) was also tested against a panel of the 3 most important vaginal *Lactobacillus* species (Table 5). While the *L. paragasseri* K7 CFCS inhibited all 11 *L. iners* strains tested (see above), it did not inhibit most of the strains from protective vaginal *Lactobacillus* species (FIG. 1). Of the 26 *L. (para)gasseri* strains tested, five strains (19%) were inhibited by the K7 CFCS in the critical dilution assay, while five of 22 *L. jensenii* strains (23%) and three of 29 *L. crispatus* strains (10%) were sensitive. These results indicated that the antimicrobial activity produced by *L. paragasseri* K7 selectively inhibited *L. iners,* while sparing the majority of the beneficial vaginal *Lactobacillus* strains.

TABLE 4

Inhibitory spectrum of L. paragasseri K7 cell free culture supernatant against different pathogens in MIC assay

| Bacterial Species | Strain | Source[a] | Sensitivity[b] |
|---|---|---|---|
| Lactobacillus sakei subsp. sakei | 15521 | ATCC | +++ |
| Lactobacillus iners | HM-126 | BEI | + |
| Lactobacillus iners | HM-131 | BEI | ++ |
| Lactobacillus iners | HM-701 | BEI | + |
| Lactobacillus iners | HM-702 | BEI | +++ |
| Lactobacillus iners | HM-703 | BEI | ++ |
| Lactobacillus iners | HM-704 | BEI | ++ |
| Lactobacillus iners | HM-705 | BEI | ++ |
| Lactobacillus iners | HM-706 | BEI | ++ |
| Lactobacillus iners | HM-707 | BEI | ++ |
| Lactobacillus iners | HM-708 | BEI | ++ |
| Lactobacillus iners | 55195 | ATCC | + |
| Staphylococcus saprophyticus | 15305 | ATCC | − |
| Staphylococcus aureus | 25923 | ATCC | − |
| Staphylococcus aureus | 51651 | ATCC | + |
| Staphylococcus aureus | 6538 | ATCC | + |
| Staphylococcus agalactiae | 13813 | ATCC | + |
| Listeria monocytogenes | 19155 | ATCC | − |
| Listeria monocytogenes | NR-13234 | BEI | − |
| Listeria monocytogenes | NR-13237 | BEI | − |
| Listeria monocytogenes | HM-1048 | BEI | − |
| Listeria monocytogenes | NR-4098 | BEI | − |
| Listeria monocytogenes | NR-110 | BEI | − |
| Enterococcus faecalis | 101-1 | Osel | ++ |
| Enterococcus faecalis | NR-31884 | BEI | + |
| Enterococcus faecalis | NR-31970 | BEI | + |
| Enterococcus faecalis | NR-31971 | BEI | + |
| Enterococcus faecalis | NR-31972 | BEI | + |
| Enterococcus faecalis | NR-31973 | BEI | ++ |
| Enterococcus faecalis | NR-31975 | BEI | + |
| Enterococcus faecalis | NR-31979 | BEI | + |
| Enterococcus faecalis | NR-31990 | BEI | + |
| Enterococcus faecalis | HM-200 | BEI | + |
| Enterococcus faecalis | HM-201 | BEI | + |
| Gardnerella vaginalis | # 9 (clade 3)[c] | Osel | + |
| Gardnerella vaginalis | # 2 (clade 4) | Osel | + |
| Gardnerella vaginalis | 44005 (clade 4) | CCUG | − |
| Gardnerella vaginalis | 44006 (clade 1) | CCUG | − |
| Gardnerella vaginalis | HM-1108 (clade 1) | BEI | − |
| Gardnerella vaginalis | HM-1109 (clade 1) | BEI | − |
| Gardnerella vaginalis | HM-1115 (clade 2) | BEI | − |
| Gardnerella vaginalis | HM-1112 (clade 2) | BEI | − |
| Gardnerella vaginalis | HM-133 (clade 1) | BEI | − |
| Gardnerella vaginalis | HM-1110 (clade 2) | BEI | − |
| Gardnerella vaginalis | HM-1105 (clade 4) | BEI | − |
| Gardnerella vaginalis | 14018 | ATCC | − |
| Atopobium vaginae | 44116 | CCUG | − |
| Finegoldia spp. | | Osel | + |
| Prevotella spp. | | Osel | − |

[a]ATCC: American Type Culture Collection; BEI: Biodefense and Emerging Infections Research Resources Repository (NIH); CCUG: Culture Collection University of Gothenburg; Osel: clinical isolates from Osel's strain collection.
[b]−: <20 BU/mL; +: 20-100 BU/mL; ++: 101-500 BU/mL; +++: >500 BU/mL.
[c]Gardnerella vaginalis clades were determined as described in Balashov, S. et al. J Med Microbiol. 2014, 63, 162-75.

TABLE 5

Inhibitory spectrum of partially purified bacteriocins from L. paragasseri K7 against beneficial vaginal lactobacilli in MIC assay

| Bacterial Species | Strain | Source | Sensitivity[a] |
|---|---|---|---|
| Lactobacillus crispatus | CTV-05 | Osel | − |
| Lactobacillus crispatus | MV-1A | Osel | − |
| Lactobacillus crispatus | MV-4A | Osel | − |
| Lactobacillus crispatus | MV-7A | Osel | − |
| Lactobacillus crispatus | MV-9B | Osel | − |
| Lactobacillus crispatus | MV-12A | Osel | − |
| Lactobacillus crispatus | 178-1 | Osel | − |
| Lactobacillus crispatus | 125-2 | Osel | ++ |
| Lactobacillus crispatus | SJ-3C | Osel | − |
| Lactobacillus crispatus | SJ-2B | Osel | − |
| Lactobacillus crispatus | SJ-12D | Osel | − |
| Lactobacillus crispatus | SJ-10F | Osel | − |
| Lactobacillus crispatus | SJ-1G | Osel | − |
| Lactobacillus crispatus | SJ-6F | Osel | − |
| Lactobacillus crispatus | 228-1 | Osel | − |
| Lactobacillus crispatus | 231 | Osel | − |
| Lactobacillus crispatus | 182-1A | Osel | − |
| Lactobacillus crispatus | 187-3B | Osel | − |
| Lactobacillus crispatus | 210-4 | Osel | − |
| Lactobacillus crispatus | 219-1 | Osel | ++ |
| Lactobacillus crispatus | HM-103 | BEI | − |
| Lactobacillus crispatus | HM-370 | BEI | − |
| Lactobacillus crispatus | HM-419 | BEI | − |
| Lactobacillus crispatus | HM-420 | BEI | − |
| Lactobacillus crispatus | HM-421 | BEI | − |
| Lactobacillus crispatus | HM-423 | BEI | − |
| Lactobacillus crispatus | HM-375 | BEI | − |
| Lactobacillus crispatus | HM-373 | BEI | − |
| Lactobacillus crispatus | 60 | ATCC | ++ |
| Lactobacillus jensenii | 1153 | Osel | ++ |
| Lactobacillus jensenii | MV-9A | Osel | − |
| Lactobacillus jensenii | MV-6A | Osel | − |
| Lactobacillus jensenii | MV-5A | Osel | − |
| Lactobacillus jensenii | SV-13B | Osel | − |
| Lactobacillus jensenii | SV-12B | Osel | − |
| Lactobacillus jensenii | SV-10C | Osel | − |
| Lactobacillus jensenii | SV-15A | Osel | +++ |
| Lactobacillus jensenii | SV-6C | Osel | − |
| Lactobacillus jensenii | SJ-16D | Osel | − |
| Lactobacillus jensenii | SJ-5D | Osel | − |
| Lactobacillus jensenii | 7A | Osel | − |
| Lactobacillus jensenii | SJ-19A | Osel | − |
| Lactobacillus jensenii | MV-27C | Osel | − |
| Lactobacillus jensenii | 236-1 | Osel | − |
| Lactobacillus jensenii | 237-1A | Osel | ++ |
| Lactobacillus jensenii | SJ-11A | Osel | − |
| Lactobacillus jensenii | SJ-15A | Osel | − |
| Lactobacillus jensenii | 211-2 | Osel | ++ |
| Lactobacillus jensenii | 221-2B | Osel | ++ |
| Lactobacillus jensenii | 232-1B | Osel | − |
| Lactobacillus jensenii | 235 | Osel | − |
| Lactobacillus gasseri | 105-1 | Osel | − |
| Lactobacillus gasseri | 151-2 | Osel | − |
| Lactobacillus gasseri | MV-10B | Osel | − |
| Lactobacillus gasseri | MV-10A | Osel | − |
| Lactobacillus gasseri | SV-16A | Osel | − |
| Lactobacillus gasseri | SV-16B | Osel | − |
| Lactobacillus gasseri | 31-3 | Osel | − |
| Lactobacillus gasseri | 175-1 | Osel | − |
| Lactobacillus gasseri | 182-1B | Osel | − |
| Lactobacillus gasseri | 9-1 | Osel | + |
| Lactobacillus gasseri | 167-1A | Osel | − |
| Lactobacillus gasseri | 144-1 | Osel | + |
| Lactobacillus gasseri | 167-1B | Osel | − |
| Lactobacillus gasseri | 37-4 | Osel | + |
| Lactobacillus gasseri | SJ-9E | Osel | − |
| Lactobacillus gasseri | SV-19B | Osel | − |
| Lactobacillus gasseri | SV-8A | Osel | − |
| Lactobacillus gasseri | 1151 | Osel | − |
| Lactobacillus gasseri | HM-398 | BEI | − |
| Lactobacillus gasseri | HM-1278 | BEI | − |
| Lactobacillus gasseri | HM-404 | BEI | ++ |
| Lactobacillus gasseri | HM-409 | BEI | − |
| Lactobacillus gasseri | HM-407 | BEI | − |
| Lactobacillus gasseri | HM-410 | BEI | − |
| Lactobacillus paragasseri | HM-104 (JV-V03) | BEI | + |
| Lactobacillus iners | HM-702 | BEI | +++ |

[a]−: <40 BU/mL; +: 40-100 BU/mL; ++: 101-500 BU/mL; +++: >500 BU/mL (iv) Co-Culture Experiments with *L. iners* and *L. paragasseri* K7.

Figure 2:
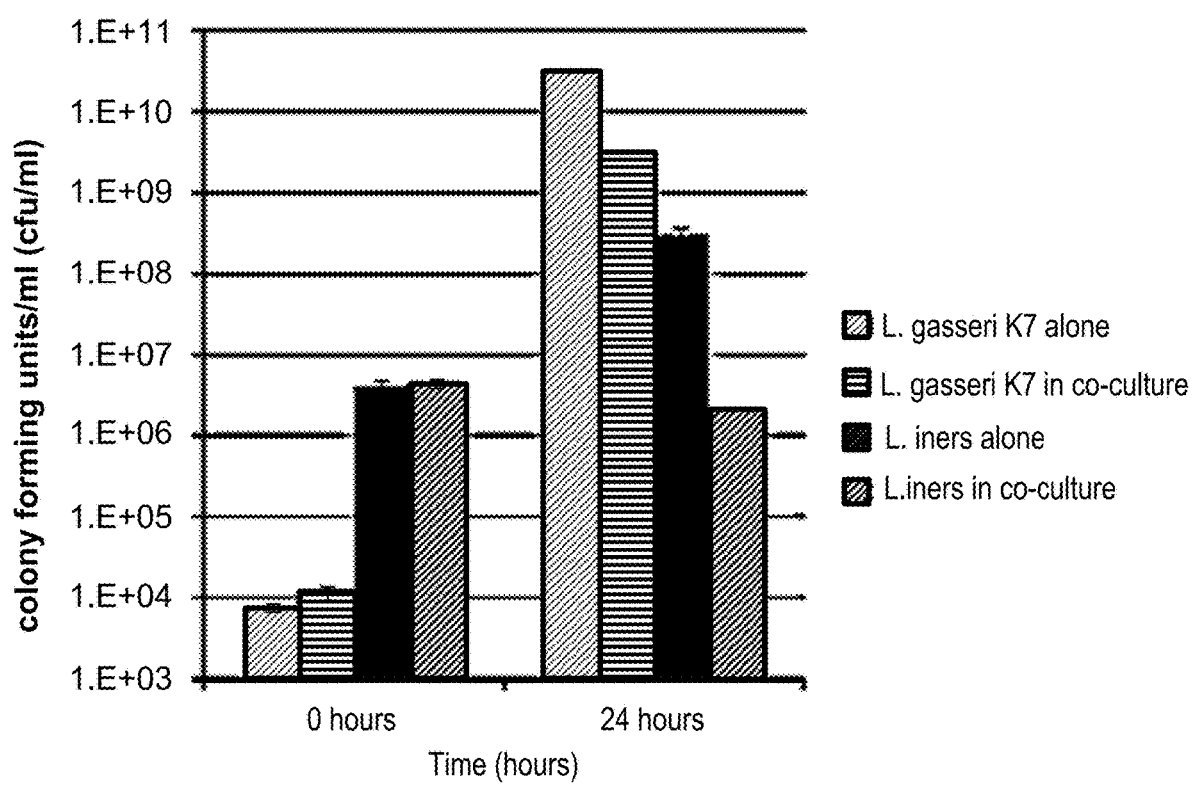
FIG. 2 illustrates the growth of *L. iners* HM-702 and *L. paragasseri* K7, cultured individually and co-cultured together in MRS:NYC III media. The growth of *L. iners* HM-702 and *L. paragasseri* K7 for each culture experiment was measured in (CFU/mL), at zero hours and after 24 hours. Initial concentration of *L. iners* HM-702 was >2 logs higher than *L. paragasseri* K7. The limit of detection for co-cultured *L. iners* was $10^6$ CFU/mL.

Because *L. paragasseri* K7 was the *Lactobacillus* strain that showed the most inhibitory activity against *L. iners* HM-702, as determined from the antimicrobial activity screening tests described above, *L. paragasseri* K7 was co-cultured with *L. iners* for further activity tests. *L. paragasseri* K7 (~5×10$^3$ CFU/mL) was co-inoculated with *L. iners* HM-702 (~1×10$^6$ CFU/mL) in 5 mL broth (1:1 (v/v) of MRS and NYC III ATCC 1685). As controls, *L. iners* HM-702 and *L. paragasseri* K7 were grown alone with conditioned media (pH 3.8, same volume as inoculum). The inoculated cultures were incubated at 37° C. in an anaerobic jar for 24 hours, and serial dilutions of the cultures were plated in triplicate on agar plates (MRS for *L. paragasseri* K7, Columbia agar for *L. iners* HM-702). Both *L. paragasseri* K7 and *L. iners* HM-702 grew on Columbia agar, but the species were easily distinguished due to size and morphology of the colonies formed. Growth of *L. iners* HM-702 and *L. paragasseri* K7 was measured by plate counting on MRS and blood agar. As shown in FIG. 2, the growth of *L. iners* was inhibited when co-cultured with *L. paragasseri* K7. The amount of *L. iners* HM-702 in the co-culture experiment could not be accurately quantified at the 24-hour time point due to overgrowth of *L. paragasseri* K7 on the blood agar plates but was determined to be below 2×10$^6$ CFU/mL (FIG. 2).

(v) Mode of Action of Antimicrobial Activity.

Figure 3:
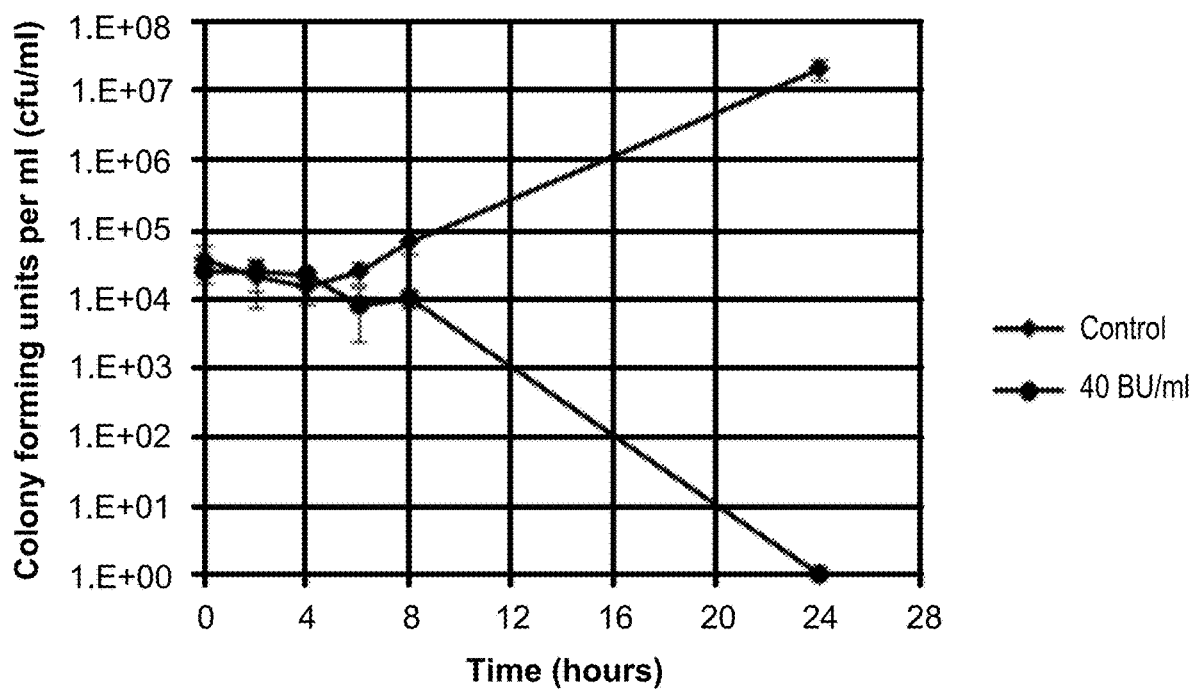
FIG. 3 illustrates the killing of *L. iners* HM-702 in the presence of 40 BU/mL semi-purified GasK7 bacteriocins over 24 hours, measured in CFU/mL of *L. iners* HM-702.
Figure 4:
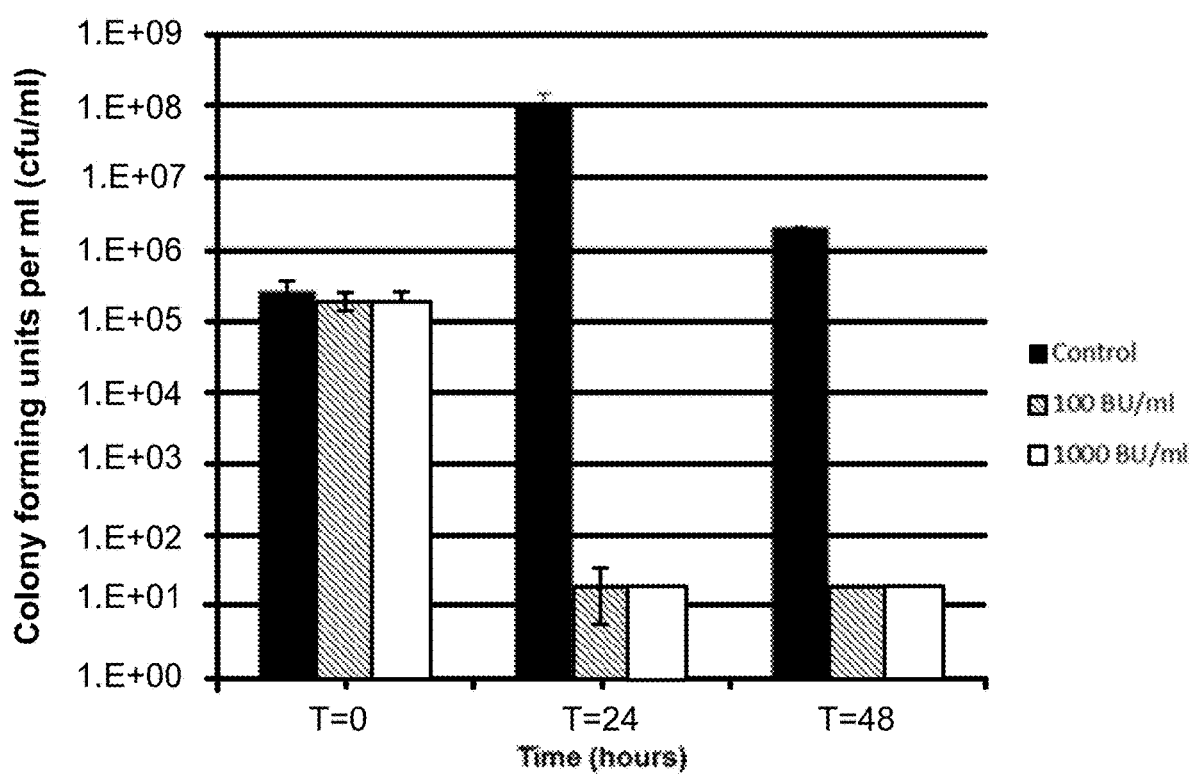
FIG. 4 illustrates the inhibition of *L. iners* HM-702 in the presence of 100 BU/mL semi-purified GasK7 bacteriocins and 1000 BU/mL GasK7 bacteriocins at zero hours, after 24 hours, and at 48 hours, measured in CFU/mL of *L. iners* HM-702.

Since an inhibitor of *L. iners* had never been described before, the activity was further characterized as follows. Overnight cultures of *L. iners* HM-702 were diluted in fresh NYC III growth media to a concentration of approximately 10$^4$-10$^5$ CFU/mL. A semi-purified bacteriocin fraction was added (eluate from Amberlite XAD-16 in 2-propanol and 0.1% (v/v) trifluoroacetic acid (TFA) and the culture was incubated anaerobically at 37° C. A control was included with 2-propanol and TFA without bacteriocin. Three different bacteriocin concentrations (40, 100, and 1000 BU/mL) were tested and the number of viable bacteria were determined by dilution and plating at appropriate time intervals on Columbia blood plates (Hardy). Each dilution was plated in triplicate. FIGS. 3 and 4 show results of the *L. iners* inhibition activity.

The anti-*L. iners* activity was recovered in both the filtrate and retentate fractions of spin columns with molecular weight cut-offs of 100, 30, 10, and 3 kDa, indicating that the inhibitor was a small protein or peptide that binds to other larger molecules in the conditioned medium. The activity could be concentrated by ammonium sulfate precipitation or by absorption to Amberlite XAD, and the activity could be eluted from the Amberlite resin with isopropanol, suggesting that the inhibitor was a hydrophobic protein/peptide. As shown in FIG. 3, the semi-purified K7 bacteriocins killed *L. iners* HM-702 at 40 BU/mL within 24 hours, indicating that the activity of the inhibitor was bactericidal, rather than bacteriostatic. The semi-purified K7 bacteriocins also killed *L. iners* HM-702 at 100 BU/mL and 1000 BU/mL within 24 hours, and further inhibited growth of *L. iners* for an additional 24 hours, as shown in FIG. 4.

Results from the antimicrobial activity tests also indicated that the inhibitory factor present in cell-conditioned medium (pH 3.8) was not lost upon neutralization of the medium (pH 7, NaOH). A growth media control (MRS) was adjusted to pH 3.8 using lactic acid and its inhibition of *L. iners* HM-702 (1×10$^5$ CFU/mL initial concentration) was compared to that of *L. paragasseri* K7 culture supernatant in the critical dilution assay. After 24 hours anaerobic incubation at 37° C., optical density readings of the K7 supernatant samples showed 128-fold higher inhibition of the indicator then the control growth media with low pH. Furthermore, the inhibitor (GasK7 bacteriocins) was sensitive to trypsin and proteinase K, which was another indication that the inhibitor was a protein or peptide. However, because the activity was not heat sensitive, it was determined that the inhibitor was not a large protein. These characteristics are consistent with that of a bacteriocin: small hydrophobic peptides that, in most cases, form pores in the membranes of target cells.

(vi) Bacteriocin Purification.

Figure 5A:
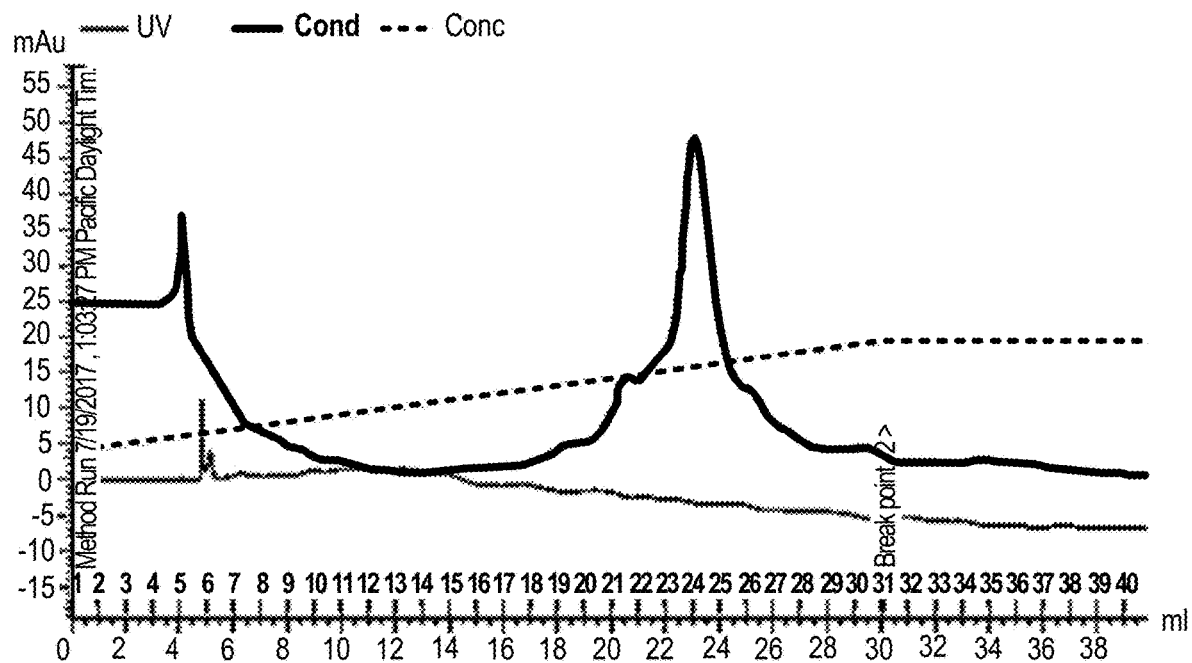
FIG. 5A presents a reverse phase chromatogram of the K7B α peptide fractions.
Figure 5B:
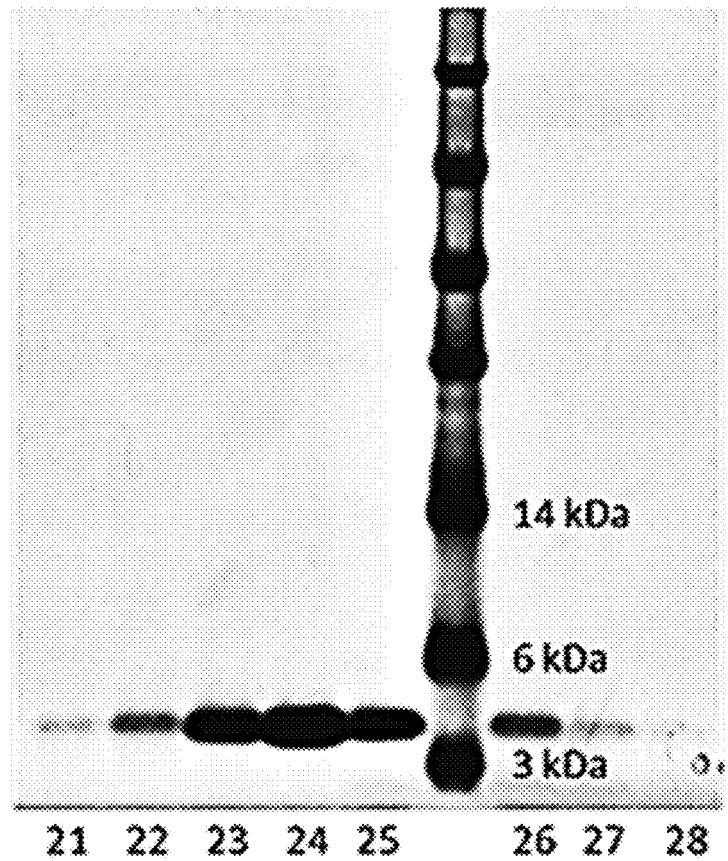
FIG. 5B presents the SDS-PAGE of the K7B α peptide fractions from the reverse phase chromatography run.

Once the bacteriocin activity against *L. iners* was confirmed and characterized, the *L. paragasseri* K7 bacteriocins were purified for further analysis and characterization. Bacteriocins were purified from 500 ml of cell free culture supernatant of *L. paragasseri* K7 grown in MRS broth (Difco) for 18 hours at 37° C. The cells were removed by centrifugation (8,000×g, 30 minutes at 4° C.), sterile filtered (0.2 um filter) and added to 30 g of Amberlite XAD-16 (Sigma). The slurry was shaken for 2 hours at room temperature (100 rpm, shaking platform), decanted to separate the supernatant from the resin and washed with 40% ethanol (500 ml, 1 hour at room temperature). The antimicrobial activity was eluted by adding 150 ml of 2-propanol with 0.1% (v/v) of TFA after shaking for 1 hour at room temperature. The Amberlite XAD-16 eluate was sterile filtered (0.2 µm filter), diluted 10-fold in H$_2$O with 0.1% (v/v) of TFA, and loaded onto a Reverse Phase Column (Resource RPC, 1 ml, GE Healthcare) connected to an Äkta protein purification system (GE Healthcare). The bacteriocins were eluted from the column with a linear gradient of 2-propanol in water (40-60%, with 0.1% TFA). Fractions with antimicrobial activity were re-run on RPC with adjusted 2-propanol gradients until pure proteins were obtained as judged by SDS-PAGE. The molecular weights of the purified bacteriocins were determined using a Bruker Autoflex (TOF) mass spectrometer. This 2-step purification procedure resulted in >90% purity of a small protein population with >90% recovery of activity. As shown in FIGS. 5A and 5B, fractions 24 and 25 from the RPC chromatogram corresponded to the purified GasK7B α, as indicated by the corresponding SDS-PAGE.

Figure 6:
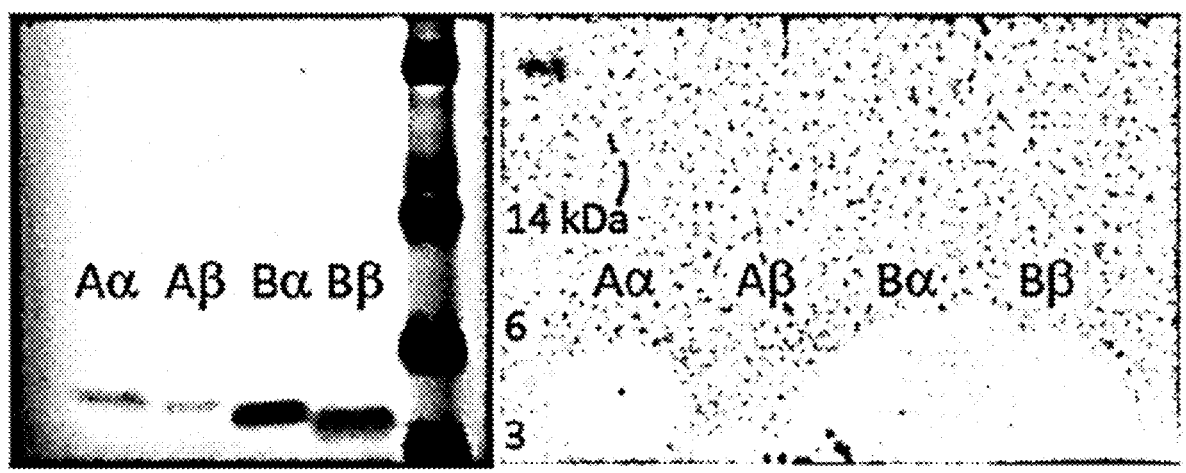
FIG. 6 presents the SDS-PAGE of the purified bacteriocins from *L. paragasseri* K7 (GasK7A α, GasK7B α, and GasK7B β) and from *E. coli* Shuffle (GasK7A β). Left gel: Bacteriocins visualized with SafeEx protein dye migrating between 3 and 6 kDa. Right gel: Zones of growth inhibition of *L. sakei* subsp. *sakei* ATCC 15521 in overlaid MRS soft agar to detect the purified bacteriocins directly in the gel (incubated for 20 hours at 30° C.).

Concentrations of the purified GasK7 bacteriocins were determined from SDS-PAGE gels, comparing the intensity of the protein bands with the bands of a standard of known concentrations (determined at 280 nm, Nanodrop). Azure c300 digital gel analyzer was used for capturing the SDS-PAGE gel pictures and Azure Spot software was used for the quantification (Azure Biosystems, CA). Bacteriocin activity of the purified GasK7 bacteriocins was tested directly in the SDS-PAGE gels (NuPage, 4-12% bis-Tris, Life Technologies). A non-stained gel with purified bacteriocin was washed in sterile water (100 ml) for 2 hours before being transferred to a BHI agar plate. An indicator lawn of 5 ml of NYC III soft agar (0.7% agar) containing ~ 1×10$^6$ cfu/ml of *L. iners* HM-702 or *L. sakei* subsp. *sakei* ATCC 15521 was poured over the gel. The agar plate was incubated anaerobically at 37° C. for 24 hours and examined for zones of growth inhibition. FIG. 6 shows the size, purity and activity of the three purified peptides from *L. paragasseri* K7 (K7A α, K7B α, and K7B β) run on reducing SDS-PAGE gel. The three peptides were analyzed by MALDI-TOF mass spectrometry and the molecular masses were determined.

Figure 7:
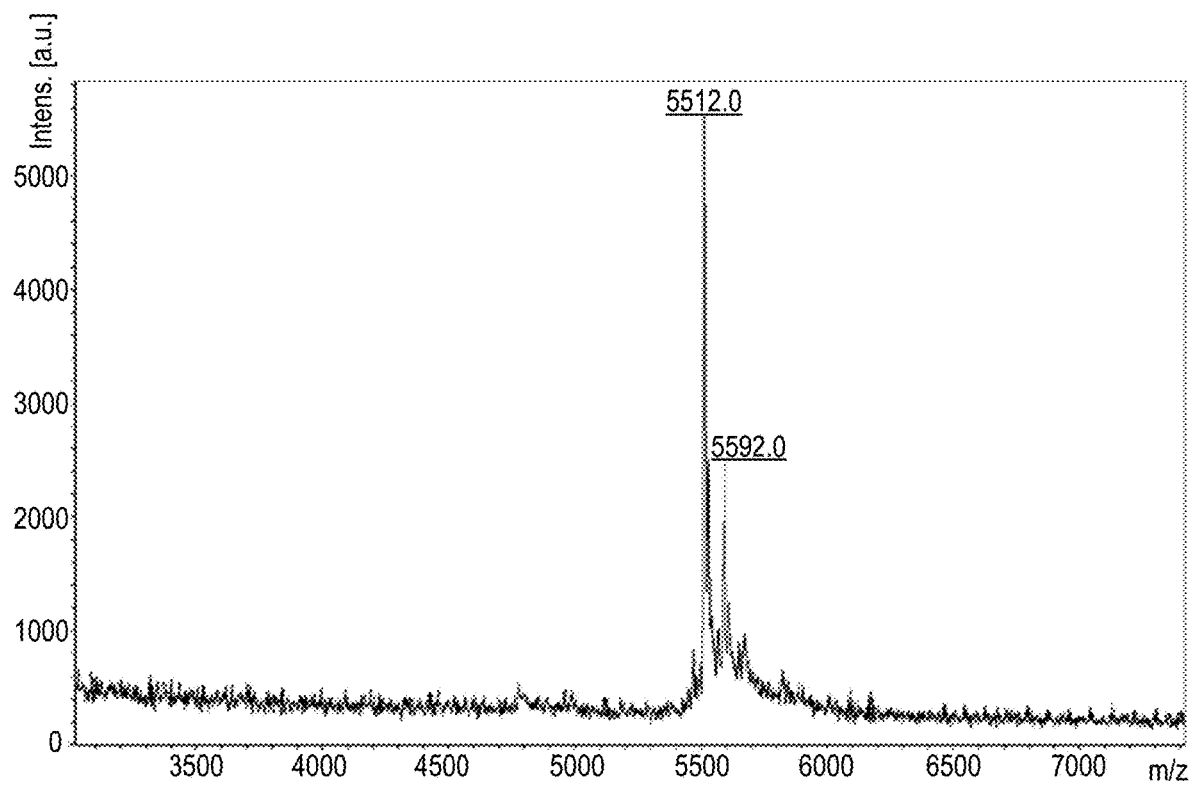
FIG. 7 presents the MALDI-TOF MS spectrum of bacteriocin peptide K7B α with m/z of 5512.0.
Figure 8:
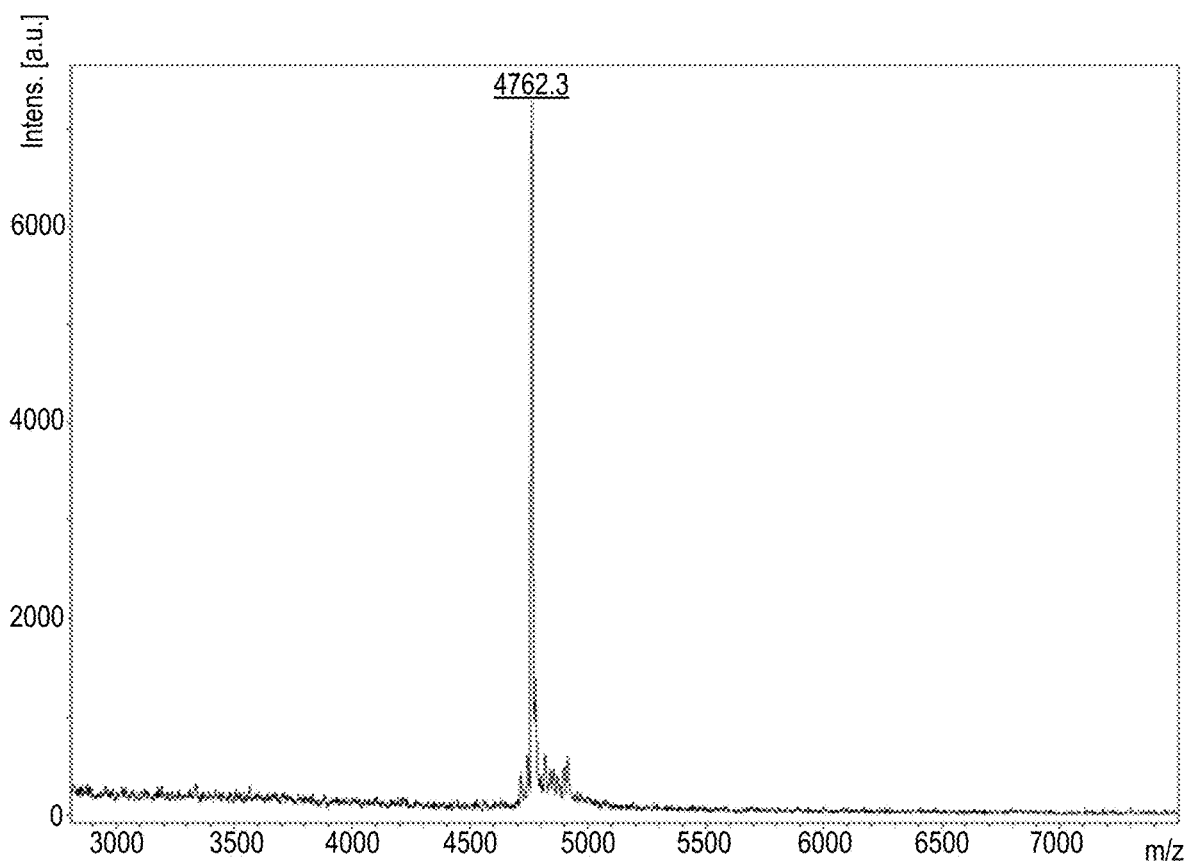
FIG. 8 presents the MALDI-TOF MS spectrum of bacteriocin peptide K7B β with m/z of 4762.3.
Figure 9:
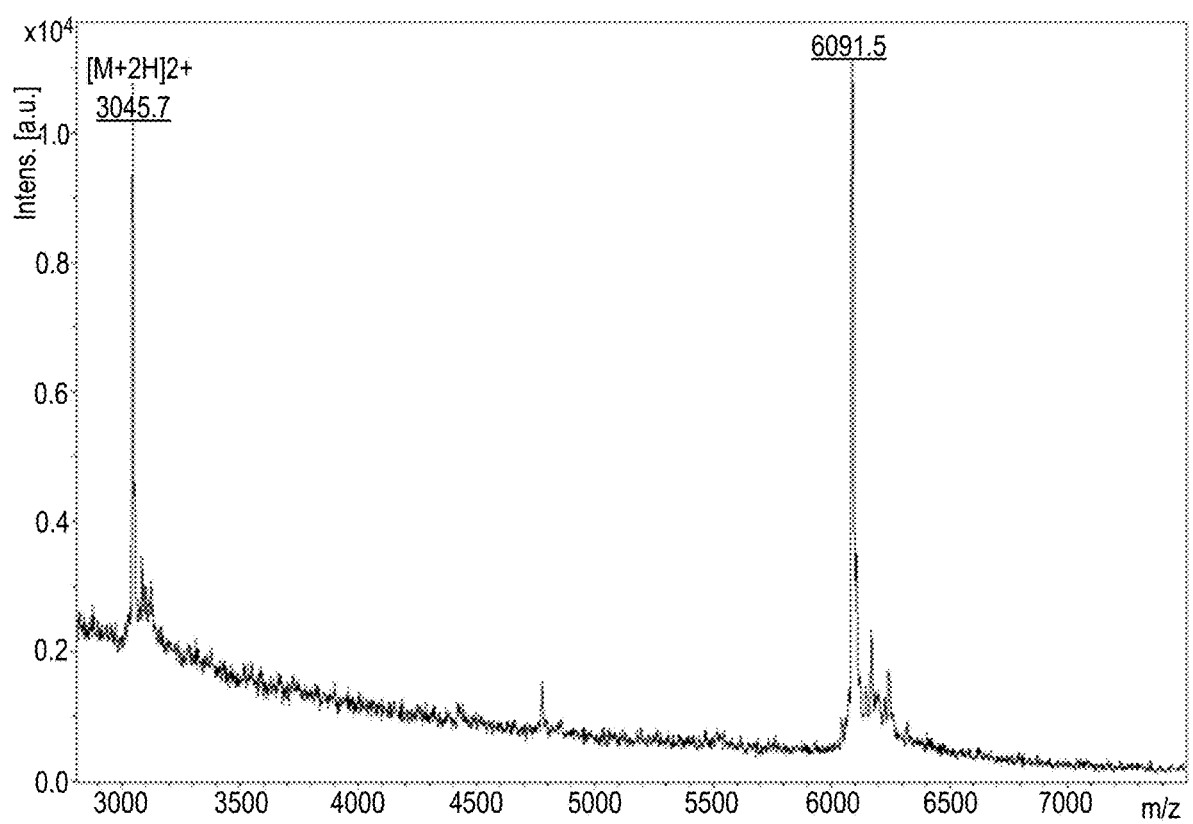
FIG. 9 presents the MALDI-TOF MS spectrum of bacteriocin peptide K7A α with m/z of 6091.5.

Peak inhibitory activity coincided with several small protein bands of ~5 kDa that were identified by MALDI-TOF mass spectrometry, as shown in FIG. 6. The greatest anti-*L. iners* activity resided in a protein with a mass of 5512, corresponding to the *L. paragasseri* K7B α component (FIG. 7). A minor peak of activity corresponded to the K7B β component with a mass of 4762 (FIG. 8). The K7B13 component appeared to be the complementary peptide of the K7B bacteriocin, while the K7B α component was the active peptide of the bacteriocin. A protein corresponding to the K7A α component of the K7A bacteriocin with a mass of 6091 (FIG. 9) was also identified. The K7A component, with an expected molecular mass of 5523 Da, was not identified or purified from the K7 supernatant in this study.

Each of the three purified peptides from *L. paragasseri* K7 supernatant was active against *L. iners* HM-702 and *L. sakei* subsp. *sakei* ATCC 15521. In general, *L. iners* was about 10-fold less sensitive to the peptides than *L. sakei* subsp. *sakei*. The minimum inhibitory concentrations (MICs) were determined for the three peptides, individually and in different combinations, against the two indicator strains as shown in Table 6. GasK7B α was the most potent peptide and killed *L. iners* with a MIC of 25 ng/ml (5 nM). The GasK7B β peptide was considerably less active than GasK7B α against both strains, with a MIC >100 ng/ml for *L. iners*. Combining the GasK7B α and GasK7B β peptides together in a ratio of about 1:1 (w/w) increased the activity >10-fold against *L. iners*, reducing the MIC to less than 2 ng/mL (~400 μM for each peptide), thus showing the synergistic activity embodied by the two peptides of the K7B bacteriocin (Table 6). The GasK7A α peptide also showed activity against *L. iners* (MIC 75 ng/mL, 12 nM), albeit less potent than the activity of K7B α. A modest increase in activity was observed when GasK7A α was combined with GasK7B β (MIC 50 ng/mL), whereas the combination of GasK7A α and GasK7B α peptides resulted in an activity similar to GasK7B α alone (MIC 25 ng/mL).

TABLE 6

MICs of purified bacteriocins, alone and in combination, against *L. iners* HM-702 and *L. sakei* subsp. *sakei* ATCC 15521 determined in the critical dilution assay. The ratio of peptides was about 1:1 (w/w), unless otherwise noted.

| Bacteriocin peptide(s) | *L. iners* HM-702 MIC (ng/mL) | *L. sakei* subsp. *sakei* ATCC 15521 MIC (ng/mL) |
| --- | --- | --- |
| GasK7A α | 75 | 9.4 |
| GasK7A β* | >4000 | >4000 |
| GasK7A α + GasK7A β* | ND$^a$ | 2.3$^b$ |
| GasK7B α | 25 | 1.6 |
| GasK7B β | >100 | 25 |
| GasK7B α + GasK7B β | 1.6 | 0.3 |
| GasK7A α + GasK7B β | 50 | 3.1 |
| GasK7A α + GasK7B α | 25 | 3.1 |
| GasK7A α + GasK7B α + GasK7B β | 2.1 | 0.1 |

*Expressed and isolated from *E. coli* Shuffle.
$^a$Not determined.
$^b$GasK7A β from *E. coli* used at 135 ng/mL.

To recapitulate, among vaginal *Lactobacillus* strains, it was found that the K7 bacteriocins were selective for *L. iners* strains. All *L. iners* strains tested (N=11) were sensitive to *L. paragasseri* K7 conditioned medium and the semi-purified bacteriocins. Results from the critical dilution assays showed that when compared to *L. iners*, the vaginal strains of *L. (para)gasseri* (N=26), *L. crispatus* (N=29), and *L. jensenii* (N=22) were less sensitive to the GasK7 bacteriocins. Of the *L. jensenii* strains, 78% were insensitive to the bacteriocin, compared to 90% of the *L. crispatus* strains and 81% of the *L. (para)gasseri* strains. *L. crispatus* CTV-05 used in LACTIN-V was insensitive to the K7 bacteriocins in cell-free culture supernatant.

(vii) Heterologous Expression of the GasK7B α and K7A β Peptides in *E. coli*.

The genome sequence of *L. paragasseri* K7 is publicly available at the Joint Genome Institute (IMG genome #2561511119) and GenBank (ASRG02000000). The DNA sequences for the bacteriocin genes of the GasK7A β peptide (ASRG02000001, region 43880-44089) and the GasK7B α peptide (ASRG02000002, region 112159-112386), without the double glycine secretion signal peptides, were cloned downstream of and in frame with maltose binding protein (MBP) using expression vectorpMAL-c5X for cytoplasmic expression (New England Biolabs). Primers used for amplification of the bacteriocin genes are K7B alpha_MAL_F: K7B alpha_F 5'-agaaataattgggctgctaatata-3' (SEQ ID NO: 16) and K7B alpha_MAL_SbfI_R 5'-tttttaaagcctgcagattccc-tacttttct-3' (SEQ ID NO: 17), K7A_beta_F: 5'-aacaacgtaaat-tggggtag-3' (SEQ ID NO: 18) and K7A_beta_SbfI_R: 5'ttac-tatccatattccctgcaggtactatctcttt-3' (SEQ ID NO: 19).

PCR was carried out in 50 ul volume reactions using 10× Accuprime Pfx reaction mix, primers at 500 nM, 1% (v/v) of Pfx DNA polymerase (Thermo Fisher), and 50 ng genomic DNA (gDNA) from *L. paragasseri* K7. Annealing temperature was 53° C. for 20 seconds followed by elongation at 68° C. for 30 seconds. The plasmids were constructed as recommended by the manufacturer, verified by DNA sequencing (MCLAB, Ca, USA), and transformed into protease deficient strains *E. coli* ER2523 and *E. coli* Shuffle for expression (New England Biolabs, MA). In short, *E. coli* cells with the correct plasmids were grown in Luria Bertani (LB) broth+100 μg/ml ampicillin+0.2% (w/v) glucose until optical density reached 0.5 (600 nm). Fusion proteins were induced with 0.3 mM IPTG for 2 hours at 37° C. and 250 rpm and recovered from the cytoplasmic or periplasmic fractions as described by the manufacturer.

The fusion proteins were then purified on an amylose column (MBP Hi-Trap, GE Healthcare) using an Äkta Prime Plus protein purification system (GE Healthcare). The column was equilibrated with 20 mM Tris, pH 7.4, 200 mM NaCl and 1 mM EDTA (buffer A), the protein sample was diluted in the same buffer and loaded on the column. MBP-bacteriocin fusion proteins were eluted in 10 mM maltose in buffer A (buffer B). The purified fusion proteins were cleaved overnight at room temperature in buffer B with Factor Xa (1% w/w) and the bacteriocins were purified by reverse phase chromatography as described above. The activity of the *E. coli*-expressed bacteriocins was tested in the critical dilution assay against *L. iners* HM-702 and *L. sakei* subsp. *sakei* ATCC 15521. The sizes of the bacteriocins were verified by SDS-PAGE.

The bacteriocin peptide GasK7A β was not purified from the *L. paragasseri* K7 culture supernatant using the methods described here or published by Bogovič Matijašić for acidocin LF221A (similar to GasK7A β). In order to determine if the GasK7A β peptide potentially could contribute to the overall inhibition of *L. iners* by K7, the peptide was expressed as a fusion protein in *E. coli* Shuffle, a strain designed to promote disulfide bridge formation in the cytoplasm. The mature bacteriocin, without its predicted double-glycine leader peptide, was cloned downstream of and in frame with the maltose binding protein in the pMAL-c5x vector for cytoplasmic expression and a fusion protein of expected size (48 kDa) was produced after induction with IPTG (not shown). The fusion protein was purified and the GasK7A β peptide was obtained by cleavage of the fusion protein with Factor Xa. The recombinant GasK7A β peptide was not active against the sensitive *L. sakei* subsp. *sakei* indicator strain by itself (MIC >4000 ng/ml). However, when the GasK7A β peptide was tested in combination with the GasK7A α peptide purified from *L. paragasseri* K7 CFCS, it increased the inhibitory activity against *L. sakei* subsp. *sakei* by >300% compared to GasK7A α alone, clearly showing that GasK7A β was biologically active and acted synergistically with GasK7A α. The GasK7B α peptide was also successfully expressed as a MBP fusion in *E. coli* with an activity comparable to the peptide isolated from K7 (not shown).

Example 2. Combined Use of the K7 Bacteriocins and Antibiotic

The effectiveness of the combined use of the K7 bacteriocins and metronidazole was tested against *L. iners* and *G. vaginalis* in vitro. Cultures of *L. iners* HM-702 and *G. vaginalis* HM-133, *L. iners*+*G. vaginalis* co-cultures, and *L. crispatus* SJ-3C were obtained as described previously in Example 1. Overnight cultures of *L. iners*, *G. vaginalis*, and *L. crispatus* were diluted in fresh growth media to concentrations of approximately $10^5$ CFU/mL to be tested against K7 bacteriocin (from Example 1), metronidazole (Sigma-Aldrich, USA), and K7 bacteriocin+metronidazole (combined). To each culture of *L. iners*, *G. vaginalis*, the *L. iners*+*G. vaginalis* co-culture, and *L. crispatus* was added semi-purified K7 bacteriocin (80 BU/mL, quantified using *L. iners* as indicator), metronidazole (42 µg/mL), or the K7 bacteriocin+metronidazole combination, and incubated anaerobically at 37° C. for 48 hours. As controls, *L. iners*, *G. vaginalis*, the *L. iners*+*G. vaginalis*, and *L. crispatus* were incubated alone with conditioned media for 48 hours as well. The inhibition of *L. iners*, *G. vaginalis*, the *L. iners*+*G. vaginalis* co-culture, and *L. crispatus* was measured spectrophotometrically at 600 nm using a Cytation 3 plate reader (BioTek) after 24 hours and after 48 hours.

Figure 10:
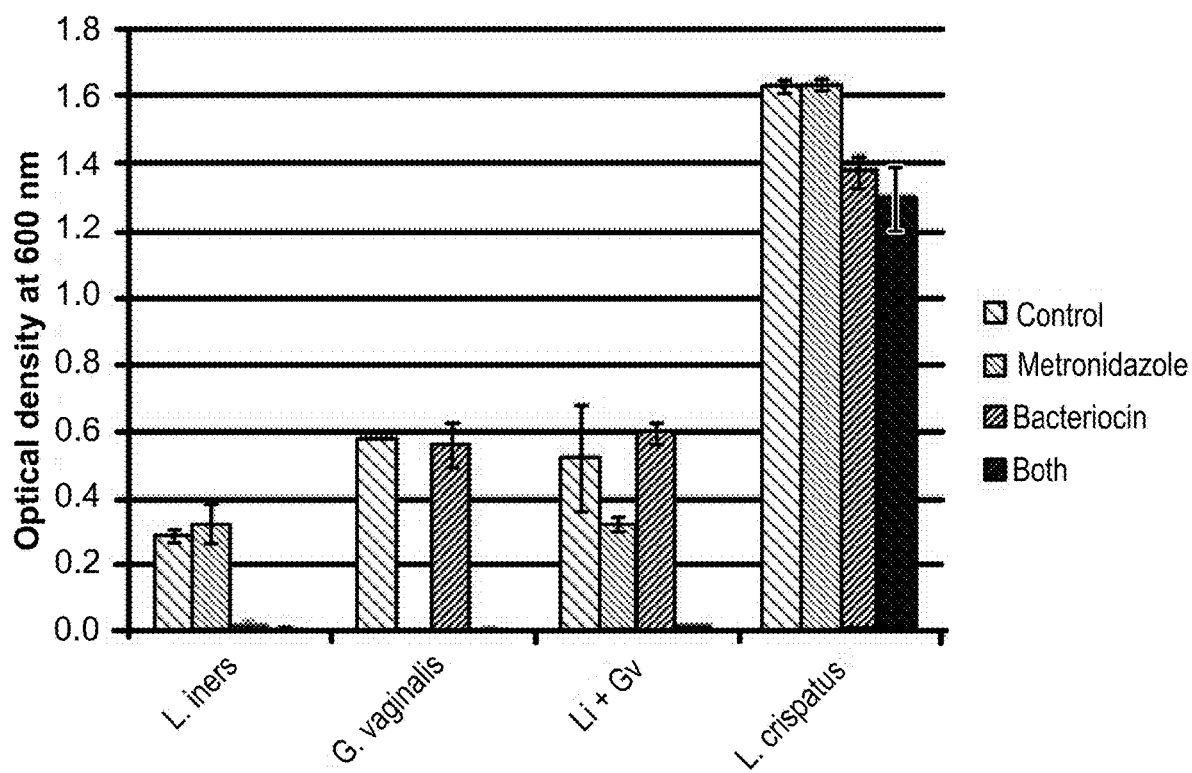
FIG. 10 illustrates the inhibition of *L. iners* HM-702, *G. vaginalis* HM-133, *L. iners*+*G. vaginalis* ("Li+Gv," co-culture, grown in NYC III medium), and *L. crispatus* SJ-3C (grown in MRS) in the presence of 100 BU/mL semi-purified GasK7 bacteriocins, 20 µg/mL metronidazole, or the 100 BU/mL K7 bacteriocin+20 µg/mL metronidazole combination after 48 hours, as measured by optical density (OD) at 600 nm.

As shown in FIG. 10, *L. iners* is sensitive to K7 bacteriocin alone and to the K7 bacteriocin+metronidazole combination but is not sensitive to metronidazole alone. Conversely, *G. vaginalis*, is sensitive to metronidazole alone and to the K7 bacteriocin+metronidazole combination but is not sensitive to the K7 bacteriocin (FIG. 10). The *L. iners*+*G. vaginalis* co-culture is inhibited by the K7 bacteriocin+metronidazole combination only. The results illustrated by FIG. 10 indicate that *L. crispatus* SJ-3C is a suitable live $H_2O_2$-producing vaginal *Lactobacillus* strain for replacement therapy due to the fact that *L. crispatus* SJ-3C was not significantly inhibited by the K7 bacteriocin, metronidazole, or the K7 bacteriocin+metronidazole combination.

Example 3. Preparing the Bacteriocin Composition

This example details the general strategy for preparing the bacteriocin composition in gel form as a medical product for intravaginal applications. While the following example describes the preparation of the bacteriocin composition on a relatively large scale, it can be understood that the methods described below are applicable for any sized production scale. Furthermore, the procedure described here is applicable for any microorganism and any pharmaceutically acceptable excipient suitable for intravaginal application.

The combination of purified GasK7B α, GasK7B β, GasK7A α, and GasK7A β peptides (peptides of SEQ ID NO:1, SEQ ID NO:2, SEQ ID NO:3, and SEQ ID NO:4, or homologs thereof) is incorporated into a formulation suitable for intravaginal applications in the appropriate amount so as to render the composition as a whole bactericidally active in vivo.

A gel based formulation for intravaginal applications with 0.1% GasK7 peptides (i.e., having an in vivo MIC for *L. iners* of 1.0 mg/mL) will be prepared by first adding a sufficient amount of methylparaben (about 40-50 g) to a 100 L stainless steel jacketed tank equipped with dual counter-rotating blades with side-scrapers and a high-shear mixer containing preheated purified water (about 40-50 kg at 70-80° C.) while mixing (blades/side scrapers about 12 RPM, high-shear mixer on high) and at a maintained temperature (70-80° C.). Mixing will continue until the methylparaben is dissolved.

Next, with maintained temperature and continuous and uninterrupted mixing, a sufficient amount of propylparaben (about 7.0-17 g) will be added and completely dissolved before adding ededate disodium in a sufficient amount (about 25-35 g). Once the ededate disodium is completely dissolved, hydroxypropylmethylcellulose (or Carbopol® 974P, or a combination of hydroxypropylmethylcellulose and Carbopol® 947P) in a sufficient amount (about 1.0-3.0 kg) will be added to the tank and continuously mixed until completely dispersed. A sufficient amount of propylene glycol (about 1.0-2.5 kg) will be added and mixing continued until completely dissolved. While mixing, a sufficient amount of the GasK7 peptides (about 0.2-1.0 kg) will then be added and mixing will be continued until the GasK7 peptides are completely dissolved. The pH will be measured to be about 5.0 (bottom) to about 6.0 (top).

While mixing, a sufficient amount of purified water (about 0.1-1.0 kg) will be added and mixed for about 15 minutes. The high shear mixer will be turned off and the mixture will be cooled to about 24° C. over about 4.5 h. The resulting bacteriocin gel containing 0.1% GasK7 peptides will then be stored in a 50-gallon tank, followed by packaging in 7.0 g tubes. Samples from various tubes throughout the batch will have a pH of about 5.3.

Example 4. Use of the Bacteriocin Composition to Treat Patients Having Diverse Microbiota Associated with BV This example details an in vivo treatment regimen for a patient having been diagnosed with low levels of $H_2O_2$-producing vaginal *Lactobacillus* and a diverse microbiota associated with BV. The treatment procedure described here demonstrates that the bacteriocin composition of the present invention, delivered to the patient as cream/gel/ovule, can inhibit *L. iners*, creating an ecological niche in the patient for recolonization of protective $H_2O_2$-producing *Lactobacillus*.

A 25-year old female patient is suffering from symptoms associated with BV, such as abnormal vaginal "fishy" odor and discharge, and discomfort from itching, burning, and pain. A diverse microbiota associated with BV is detected in the female patient by the Clinical Amsel criteria (thin grey homogeneous vaginal discharge, odor (positive whiff test), >20% clue cells, and pH >4.5), by satisfying ≥3 criteria satisfied, and confirmed microbiologically by the Nugent scoring system (Nugent Score of 7-10). The medical practitioner also confirms that the patient's vaginal mucosa is colonized by low levels of $H_2O_2$-producing vaginal *Lactobacillus* using the TMB-plus agar plate culture method, with a negative plate reading after 30 min of air exposure (minimal blue coloration of colonies).

Because the patient is diagnosed with a BV-positive Nugent score, the patient will receive concurrent treatment for *L. iners* and an antibiotic treatment for the BV-associated organisms. First, the patient is intravaginally treated with 5 grams of the 0.1% bacteriocin gel composition of Example 2 once per day for 5 days to inhibit and/or kill the *L. iners*. Along with the bacteriocin composition treatment, the female patient will also receive treatment using 0.75% topical metronidazole (MetroGel®) once a day for 5 days.

After completing the bacteriocin composition and antibiotic treatment regimens, the patient will be examined by the medical practitioner to confirm that the patient's vaginal mucosa has been recolonized with endogenous $H_2O_2$-producing vaginal *Lactobacillus*. The medical practitioner employs the TMB-plus agar plate culture method, again resulting in a negative plate reading after 30 min of air exposure, indicating low levels of $H_2O_2$-producing vaginal *Lactobacillus* in the patient's vaginal mucosa. The female patient begins treatment using a *Lactobacillus crispatus* CTV-05 dry powder drug formulation (i.e., LACTIN-V). The LACTIN-V powder is administered vaginally with a pre-filled applicator. Each pre-filled applicator contains a 200 mg dose of LACTIN-V at $2 \times 10^9$ CFU/applicator. The female patient receives one dose of LACTIN-V daily for 5 consecutive days.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A bacteriocin composition comprising at least one pharmaceutically acceptable excipient; and at least one isolated peptide, or a combination of isolated peptides, wherein:
   i) the at least one isolated peptide, or combination of isolated peptides, has selective bactericidal activity against *L. iners*;
   ii) the at least one isolated peptide is selected from the group consisting of SEQ ID NO:1, SEQ ID NO:2, SEQ ID NO:3, SEQ ID NO:4, and an isolated peptide having 90% or more sequence identity to SEQ ID NO:3 or 4; and
   iii) the bacteriocin composition is a formulation suitable for intravaginal applications, and wherein the at least one isolated peptide, or combination of isolated peptides, is present in an amount sufficient to exhibit bactericidal properties of the bacteriocin composition.

2. The bacteriocin composition of claim 1, wherein the isolated peptide is SEQ ID NO:1, SEQ ID NO:2, SEQ ID NO:3, or SEQ ID NO:4.

3. The bacteriocin composition of claim 1, wherein the combination of peptides comprises isolated peptides SEQ ID NO:1 and SEQ ID NO:2; SEQ ID NO:3 and SEQ ID NO:4; or SEQ ID NO:1, SEQ ID NO:2, SEQ ID NO:3, and SEQ ID NO:4.

4. The bacteriocin composition of claim 1, wherein the formulation is a gel, cream, ointment, foam, film, powder, pessary, insert, or suppository suitable for topical intravaginal applications.

5. The bacteriocin composition of claim 1, wherein the amount of peptide, or combination of peptides, is between 0.001% (w/w) and 3% (w/w).

6. The bacteriocin composition of claim 1, further comprising at least one antibiotic active against bacterial vaginosis (BV)-associated organisms.

7. The bacteriocin composition of claim 6, wherein the at least one antibiotic is selected from the group consisting of clindamycin, metronidazole, secnidazole, tinidazole, and astodrimer sodium.

8. A method of treating a patient having low levels of $H_2O_2$-producing vaginal *Lactobacillus* and a Nugent score of at least 4, the method comprising:
   intravaginally administering to the patient the bacteriocin composition of claim 1 in an amount sufficient to decrease levels of *L. iners* and to promote growth of endogenous $H_2O_2$-producing vaginal *Lactobacillus*.

9. The method of claim 8, further comprising administering to the patient at least one antibiotic active against BV-associated organisms, wherein the antibiotic is administered in an amount sufficient to decrease levels of BV-associated organisms.

10. The method of claim 8, further comprising administering to the patient a live bacterial composition comprising $H_2O_2$-producing vaginal *Lactobacillus*, wherein the live bacterial composition is administered in an amount sufficient to promote growth of administered $H_2O_2$-producing vaginal *Lactobacillus*.

11. The method of claim 8, wherein the isolated peptide is SEQ ID NO:1, SEQ ID NO:2, SEQ ID NO:3, or SEQ ID NO:4.

12. The method of claim 8, wherein the combination of peptides comprises isolated peptides SEQ ID NO:1 and SEQ ID NO:2; SEQ ID NO:3 and SEQ ID NO:4; or SEQ ID NO:1, SEQ ID NO:2, SEQ ID NO:3, and SEQ ID NO:4.

13. The method of claim 8, wherein the amount of the at least one peptide, or combination of isolated peptides, is between 0.001% (w/w) and 3% (w/w).

14. The method of claim 9, wherein the at least one antibiotic is selected from the group consisting of clindamycin, metronidazole, secnidazole, tinidazole, and astodrimer sodium.

15. The method of claim 9, wherein the amount of antibiotic is between about 30 mg to about 2000 mg per daily dose.

16. The method of claim 9, wherein the antibiotic is administered to the patient once daily for up to 7 days.

17. The method of claim 9, wherein the amount of antibiotic is administered concurrently with the amount of the at least one isolated peptide, or combination of isolated peptides.

18. The method of claim 10, wherein the $H_2O_2$-producing vaginal *Lactobacillus* is selected from the group consisting of L·crispatus, L·jensenii, L·gasseri, and combinations thereof.

19. The method of claim 18, wherein the $H_2O_2$-producing vaginal *Lactobacillus* is L·crispatus CTV-05.

20. The method of claim 8, wherein the amount of the at least one isolated peptide, or combination of isolated peptides, is an amount sufficient to treat BV in the patient.

\* \* \* \* \*